United States Patent
Dower et al.

(10) Patent No.: US 6,777,239 B2
(45) Date of Patent: Aug. 17, 2004

(54) EPITOPE-CAPTURED ANTIBODY DISPLAY

(75) Inventors: William J. Dower, Menlo Park, CA (US); Steven E. Cwirla, Menlo Park, CA (US)

(73) Assignee: XenoPort, Inc., Santa Clara, CA (US)

(*) Notice: Subject to any disclaimer, the term of this patent is extended or adjusted under 35 U.S.C. 154(b) by 0 days.

(21) Appl. No.: 10/125,062

(22) Filed: Apr. 17, 2002

(65) Prior Publication Data

US 2002/0192690 A1 Dec. 19, 2002

Related U.S. Application Data

(60) Provisional application No. 60/284,305, filed on Apr. 17, 2001.

(51) Int. Cl.[7] .......................... G01N 33/53; C12Q 1/68
(52) U.S. Cl. ...................... 436/6; 435/7.1; 435/7.8; 435/91.4; 435/471; 435/489; 536/23.1; 536/23.4; 536/23.5
(58) Field of Search ................. 435/6, 7.1, 7.8, 435/91.4, 471, 489; 536/23.1, 23.4, 23.5

(56) References Cited

U.S. PATENT DOCUMENTS

| | | |
|---|---|---|
| 4,591,570 A | 5/1986 | Chang |
| 4,829,010 A | 5/1989 | Chang |
| 4,880,750 A | 11/1989 | Francoeur |
| 5,212,050 A | 5/1993 | Mier et al. |
| 5,270,167 A | 12/1993 | Francoeur |
| 5,514,548 A | 5/1996 | Krebber et al. |
| 5,571,698 A | 11/1996 | Ladner et al. |
| 5,741,462 A | 4/1998 | Nova et al. |
| 5,837,454 A | 11/1998 | Cozzette et al. |
| 6,057,098 A | 5/2000 | Buechler et al. |
| 6,084,062 A | 7/2000 | Maclennan et al. |
| 6,225,047 B1 | 5/2001 | Hutchens et al. |

FOREIGN PATENT DOCUMENTS

| | | |
|---|---|---|
| EP | 0 436 597 B1 | 4/1997 |
| WO | WO 01/98366 A2 | 12/2001 |

OTHER PUBLICATIONS copy of International Search Report for PCT/US02/12145.
Cwirla, Steven E., et al; Peptides on phage: A vast library of peptides for identifying ligands; *Proc. Natl. Acad. Sci. USA*; Aug. 1990; pp. 6378–6382; vol. 87.
Devlin, James J., et al.; Random Peptide Libraries: A Source of Specific Protein Binding Molecules; *Science*; Jul., 27, 1990; pp. 404–406; vol. 249.
Scott, Jamie K., et al.; Searching for Peptide Ligands with an Epitope Library; *Science*; Jul. 27, 1990; pp. 386–390; vol. 249.

*Primary Examiner*—Long V. Le
*Assistant Examiner*—Jacob Cheu
(74) *Attorney, Agent, or Firm*—Townsend and Townsend and Crew LLP

(57) ABSTRACT

Reagents and methods for detecting target proteins in a sample are provided. The reagents include a replicable genetic package, a protein displayed on an exterior surface of the package that is expressed from a heterologous nucleic acid borne by the package, and one or more antibodies complexed with the expressed protein and which have an open binding site for a target protein. Thus, a segment of the nucleic acid encodes for an epitope that is shared by the expressed polypeptide and the target protein. The reagents can be utilized individually or as part of a library or an array to bind target proteins within protein samples to form one or more complexes. By determining the sequence of the segment of the heterologous nucleic acid of a package within a complex, one can identify the target protein since the segment encodes for an epitope that is shared by the expressed and target proteins.

36 Claims, 19 Drawing Sheets

| | | | | | |
|---|---|---|---|---|---|
| TNFR_EC_domain | MGLSTVPDLL | LPLVLLELLV | GIYPSGVIGL | VPHLGDREKR | DSVCPQGKYI |
| BAF225-1_insert | .......... | .......... | ...PSGVIGL | VPHLGDREKR | DSVCPQGKYI |
| BAF225-2_insert | .......... | .......... | .......... | VPHLGDREKR | DSVCPQGKYI |
| BAF225-3_insert | .......... | .......... | .......... | .......... | .......... |
| BAF225-4_insert | .......... | .......... | .......... | .......... | .......... |
| BAF225-5_insert | .......... | .......... | .......... | .......... | .......... |
| BAF225-6_insert | .......... | .......... | .......... | .......... | .......... |

| | | | | | |
|---|---|---|---|---|---|
| TNFR_EC_domain | HPQNNSICCT | KCHKGTYLYN | DCPGPGQDTD | CRECESGSFT | ASENHLRHCL |
| BAF225-1_insert | HPQNNSIC.. | .......... | .......... | .......... | .......... |
| BAF225-2_insert | HPQNNSICCT | KCHKGTYLYN | DCPGPGQDTD | CRECESGSFT | ASENHLRHC. |
| BAF225-3_insert | .......... | .......... | .......... | .......... | .......... |
| BAF225-4_insert | .......... | .......... | .......... | .......... | .......... |
| BAF225-5_insert | .......... | .......... | .......... | .......... | .......... |
| BAF225-6_insert | .......... | .......... | .......... | .......... | .......... |

| | | | | | |
|---|---|---|---|---|---|
| TNFR_EC_domain | SCSKCRKEMG | QVEISSCTVD | RDTVCGCRKN | QYRHYWSENL | FQCFNCSLCL |
| BAF225-1_insert | .......... | .......... | .......... | .......... | .......... |
| BAF225-2_insert | .......... | .......... | .......... | .......... | .......... |
| BAF225-3_insert | .......... | .......... | .......... | .......... | ....NCSLCL |
| BAF225-4_insert | .......... | .......... | .......... | .......... | .......... |
| BAF225-5_insert | .......... | .......... | .......... | .......... | .......... |
| BAF225-6_insert | .......... | .......... | .......... | .......... | .......... |

| | | | | | |
|---|---|---|---|---|---|
| TNFR_EC_domain | NGTVHLSCQE | KQNTVCTCHA | GFFLRENECV | SCSNCKKSLE | CTKLCLPQIE |
| BAF225-1_insert | .......... | .......... | .......... | .......... | .......... |
| BAF225-2_insert | .......... | .......... | .......... | .......... | .......... |
| BAF225-3_insert | NGTVHLSCQE | KQNTVCTCHA | GFFLRENECV | SCSNCKKSLE | CTKLCLPQI. |
| BAF225-4_insert | .........E | KQNTVCTCHA | GFFLRENECV | SCSNCKKSLE | CTKLCLPQIE |
| BAF225-5_insert | .......... | .......... | GFFLRENECV | SCSNCKKSLE | CTKLCLPQIE |
| BAF225-6_insert | NGTVHLSCQE | KQNTVCTCHA | GFFLRENECV | SCSNCKKSLE | CTKLCLPQIE |

| | | |
|---|---|---|
| TNFR_EC_domain | NVKGTEDSGT | TKL |
| BAF225-1_insert | .......... | ... |
| BAF225-2_insert | .......... | ... |
| BAF225-3_insert | .......... | ... |
| BAF225-4_insert | NVKGTEDSGT | TKL |
| BAF225-5_insert | NVKGTEDSGT | TKL |
| BAF225-6_insert | NVKGTEDSGT | TKL |

FIG. 3

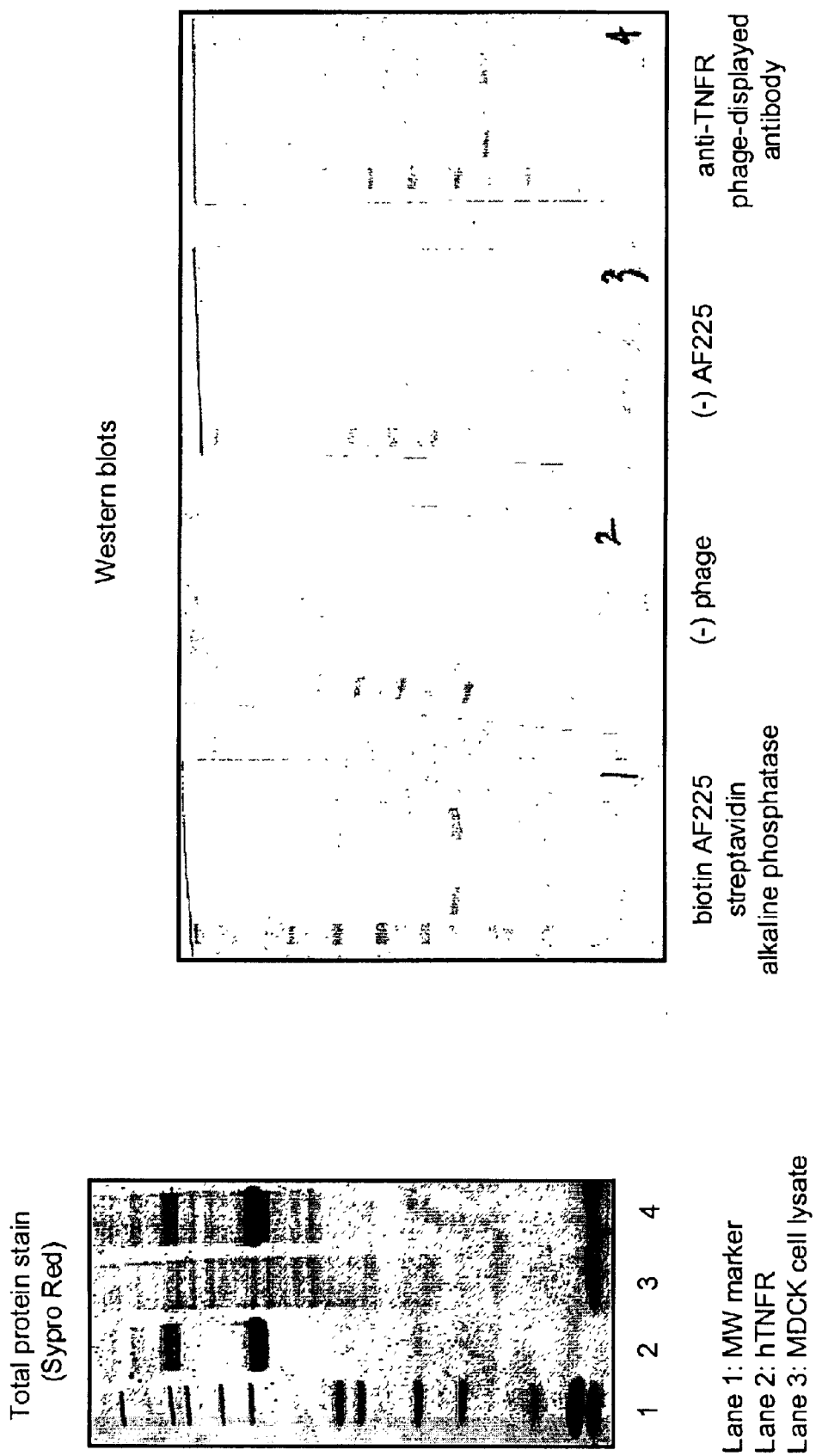

```
TNFR_EC_domain   MGLSTVPDLL LPLVLLELLV GIYPSGVIGL VPHLGDREKR DSVCPQGKYI
 BAF225-1_insert  .......... .......... .......... ..HLGDREKR DSVCPQGKYI
BAF225-12_insert  .......... .......... .......... ...LGDREKR DSVCPQGKYI
 BAF225-3_insert  .......... .......... .......... .......... ..........
 BAF225-5_insert  .......... .......... .......... .......... ..........
 BAF225-6_insert  .......... .......... .......... .......... ..........
 BAF225-7_insert  .......... .......... .......... .......... ..........
BAF225-10_insert  .......... .......... .......... .......... ..........
BAF225-11_insert  .......... .......... .......... .......... ..........
BAF225-14_insert  .......... .......... .......... .......... ..........
BAF225-16_insert  .......... .......... .......... .......... ..........

TNFR_EC_domain   HPQNNSICCT KCHKGTYLYN DCPGPGQDTD CRECESGSFT ASENHLRHCL
 BAF225-1_insert  HPQNNSICCT KCHKGTYLYN DCPGPGQDTD C......... ..........
BAF225-12_insert  HPQNNSICCT KCHKGTYLYN DCPGPGQDTD CR........ ..........
 BAF225-3_insert  .......... .......... .......... .......... ..........
 BAF225-5_insert  .......... .......... .......... .......... ..........
 BAF225-6_insert  .......... .......... .......... .......... ..........
 BAF225-7_insert  .......... .......... .......... .......... ..........
BAF225-10_insert  .......... .......... .......... .......... ..........
BAF225-11_insert  .......... .......... .......... .......... ..........
BAF225-14_insert  .......... .......... .......... .......... ..........
BAF225-16_insert  .......... .......... .......... .......... ..........

TNFR_EC_domain   SCSKCRKEMG QVEISSCTVD RDTVCGCRKN QYRHYWSENL FQCFNCSLCL
 BAF225-1_insert  .......... .......... .......... .......... ..........
BAF225-12_insert  .......... .......... .......... .......... ..........
 BAF225-3_insert  .......... .......... .......... .......... ..........
 BAF225-5_insert  .......... .......... .......... .......... ..........
 BAF225-6_insert  .......... .......... .......... .......... ..........
 BAF225-7_insert  .......... .......... .......... .......... ..........
BAF225-10_insert  .......... .......... .......... .......... ..........
BAF225-11_insert  .......... .......... .......... .......... ..........
BAF225-14_insert  .......... .......... .......... .......... ..........
BAF225-16_insert  .......... .......... .......... .......... ..........
```

FIG. 9

| TNFR_EC_domain | NGTVHLSCQE | KQNTVCTCHA | GFFLRENECV | SCSNCKKSLE | CTKLCLPQIE |
|---|---|---|---|---|---|
| BAF225-1_insert | .......... | .......... | .......... | .......... | .......... |
| BAF225-12_insert | .......... | .......... | .......... | .......... | .......... |
| BAF225-3_insert | .......... | .......... | .......... | SCSNCKKSLE | CTKLCLPQIE |
| BAF225-5_insert | .......... | .......CHA | GFFLRENECV | SCSNCKKSLE | CTKLCLPQI. |
| BAF225-6_insert | .......... | .......CHA | GFFLRENECV | SCSNCKKSLE | CTKLCLPQIE |
| BAF225-7_insert | .......... | .......... | .......... | SCSNCKKSLE | CTKLCLPQIE |
| BAF225-10_insert | .......... | .......CHA | GFFLRENECV | SCSNCKKSLE | CTKLCLPQIE |
| BAF225-11_insert | ....HLSCQE | KQNTVCTCHA | GFFLRENECV | SCSNCKKSLE | CTKLCLPQI. |
| BAF225-14_insert | .......... | ....VCTCHA | GFFLRENECV | SCSNCKKSLE | CTKLCLPQIE |
| BAF225-16_insert | .......... | .......... | .......... | SCSNCKKSLE | CTKLCLPQIE |

| TNFR_EC_domain | NVKGTEDSGT | TKL |
|---|---|---|
| BAF225-1_insert | .......... | ... |
| BAF225-12_insert | .......... | ... |
| BAF225-3_insert | .......... | ... |
| BAF225-5_insert | .......... | ... |
| BAF225-6_insert | NVKGT..... | ... |
| BAF225-7_insert | NVKGTE.... | ... |
| BAF225-10_insert | NV........ | ... |
| BAF225-11_insert | .......... | ... |
| BAF225-14_insert | NVK....... | ... |
| BAF225-16_insert | NVKGTEDS.. | ... |

FIG. 9
(Continued)

SEQUENCE LISTING

<160> NUMBER OF SEQ ID NOS: 18

<210> SEQ ID NO 1
<211> LENGTH: 213
<212> TYPE: PRT
<213> ORGANISM: Homo sapiens
<220> FEATURE:
<223> OTHER INFORMATION: human type I tumor necrosis factor (TNF)
      receptor (hTNFR-1) extracellular domain

<400> SEQUENCE: 1

```
Met Gly Leu Ser Thr Val Pro Asp Leu Leu Leu Pro Leu Val Leu Leu
 1               5                  10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Lys Leu
    210
```

<210> SEQ ID NO 2
<211> LENGTH: 35
<212> TYPE: PRT
<213> ORGANISM: Artificial Sequence
<220> FEATURE:
<223> OTHER INFORMATION: Description of Artificial Sequence:sequence
      displayed by T7 hTNFR-1 cDNA fragment phage clone
      selected for binding to the goat anti-hTNFR
      polyclonal antibody

<400> SEQUENCE: 2

```
Pro Ser Gly Val Ile Gly Leu Val Pro His Leu Gly Asp Arg Glu Lys
 1               5                  10                  15

Arg Asp Ser Val Cys Pro Gln Gly Lys Tyr Ile His Pro Gln Asn Asn
                20                  25                  30

Ser Ile Cys
        35
```

```
<210> SEQ ID NO 3
<211> LENGTH: 69
<212> TYPE: PRT
<213> ORGANISM: Artificial Sequence
<220> FEATURE:
<223> OTHER INFORMATION: Description of Artificial Sequence:sequence
      displayed by T7 hTNFR-1 cDNA fragment phage clone
      selected for binding to the goat anti-hTNFR
      polyclonal antibody

<400> SEQUENCE: 3

Val Pro His Leu Gly Asp Arg Glu Lys Arg Asp Ser Val Cys Pro Gln
 1               5                  10                  15

Gly Lys Tyr Ile His Pro Gln Asn Asn Ser Ile Cys Cys Thr Lys Cys
            20                  25                  30

His Lys Gly Thr Tyr Leu Tyr Asn Asp Cys Pro Gly Pro Gly Gln Asp
        35                  40                  45

Thr Asp Cys Arg Glu Cys Glu Ser Gly Ser Phe Thr Ala Ser Glu Asn
    50                  55                  60

His Leu Arg His Cys
 65

<210> SEQ ID NO 4
<211> LENGTH: 55
<212> TYPE: PRT
<213> ORGANISM: Artificial Sequence
<220> FEATURE:
<223> OTHER INFORMATION: Description of Artificial Sequence:sequence
      displayed by T7 hTNFR-1 cDNA fragment phage clone
      selected for binding to the goat anti-hTNFR
      polyclonal antibody

<400> SEQUENCE: 4

Asn Cys Ser Leu Cys Leu Asn Gly Thr Val His Leu Ser Cys Gln Glu
 1               5                  10                  15

Lys Gln Asn Thr Val Cys Thr Cys His Ala Gly Phe Phe Leu Arg Glu
            20                  25                  30

Asn Glu Cys Val Ser Cys Ser Asn Cys Lys Lys Ser Leu Glu Cys Thr
        35                  40                  45

Lys Leu Cys Leu Pro Gln Ile
    50                  55

<210> SEQ ID NO 5
<211> LENGTH: 54
<212> TYPE: PRT
<213> ORGANISM: Artificial Sequence
<220> FEATURE:
<223> OTHER INFORMATION: Description of Artificial Sequence:sequence
      displayed by T7 hTNFR-1 cDNA fragment phage clone
      selected for binding to the goat anti-hTNFR
      polyclonal antibody

<400> SEQUENCE: 5

Glu Lys Gln Asn Thr Val Cys Thr Cys His Ala Gly Phe Phe Leu Arg
 1               5                  10                  15

Glu Asn Glu Cys Val Ser Cys Ser Asn Cys Lys Lys Ser Leu Glu Cys
            20                  25                  30

Thr Lys Leu Cys Leu Pro Gln Ile Glu Asn Val Lys Gly Thr Glu Asp
        35                  40                  45

Ser Gly Thr Thr Lys Leu
    50
```

-continued

```
<210> SEQ ID NO 6
<211> LENGTH: 43
<212> TYPE: PRT
<213> ORGANISM: Artificial Sequence
<220> FEATURE:
<223> OTHER INFORMATION: Description of Artificial Sequence:sequence
      displayed by T7 hTNFR-1 cDNA fragment phage clone
      selected for binding to the goat anti-hTNFR
      polyclonal antibody

<400> SEQUENCE: 6

Gly Phe Phe Leu Arg Glu Asn Glu Cys Val Ser Cys Ser Asn Cys Lys
  1               5                  10                  15

Lys Ser Leu Glu Cys Thr Lys Leu Cys Leu Pro Gln Ile Glu Asn Val
             20                  25                  30

Lys Gly Thr Glu Asp Ser Gly Thr Thr Lys Leu
         35                  40

<210> SEQ ID NO 7
<211> LENGTH: 63
<212> TYPE: PRT
<213> ORGANISM: Artificial Sequence
<220> FEATURE:
<223> OTHER INFORMATION: Description of Artificial Sequence:sequence
      displayed by T7 hTNFR-1 cDNA fragment phage clone
      selected for binding to the goat anti-hTNFR
      polyclonal antibody

<400> SEQUENCE: 7

Asn Gly Thr Val His Leu Ser Cys Gln Glu Lys Gln Asn Thr Val Cys
  1               5                  10                  15

Thr Cys His Ala Gly Phe Phe Leu Arg Glu Asn Glu Cys Val Ser Cys
             20                  25                  30

Ser Asn Cys Lys Lys Ser Leu Glu Cys Thr Lys Leu Cys Leu Pro Gln
         35                  40                  45

Ile Glu Asn Val Lys Gly Thr Glu Asp Ser Gly Thr Thr Lys Leu
     50                  55                  60

<210> SEQ ID NO 8
<211> LENGTH: 49
<212> TYPE: PRT
<213> ORGANISM: Artificial Sequence
<220> FEATURE:
<223> OTHER INFORMATION: Description of Artificial Sequence:sequence
      displayed by fd hTNFR-1 cDNA fragment phage clone
      selected for binding to goat anti-hTNFR polyclonal
      antibody

<400> SEQUENCE: 8

His Leu Gly Asp Arg Glu Lys Arg Asp Ser Val Cys Pro Gln Gly Lys
  1               5                  10                  15

Tyr Ile His Pro Gln Asn Asn Ser Ile Cys Cys Thr Lys Cys His Lys
             20                  25                  30

Gly Thr Tyr Leu Tyr Asn Asp Cys Pro Gly Pro Gly Gln Asp Thr Asp
         35                  40                  45

Cys

<210> SEQ ID NO 9
<211> LENGTH: 49
<212> TYPE: PRT
<213> ORGANISM: Artificial Sequence
<220> FEATURE:
<223> OTHER INFORMATION: Description of Artificial Sequence:sequence
      displayed by fd hTNFR-1 cDNA fragment phage clone
      selected for binding to goat anti-hTNFR polyclonal
``` antibody

<400> SEQUENCE: 9

Leu Gly Asp Arg Glu Lys Arg Asp Ser Val Cys Pro Gln Gly Lys Tyr
1               5                   10                  15

Ile His Pro Gln Asn Asn Ser Ile Cys Cys Thr Lys Cys His Lys Gly
            20                  25                  30

Thr Tyr Leu Tyr Asn Asp Cys Pro Gly Pro Gln Asp Thr Asp Cys
        35                  40                  45

Arg

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence:sequence
      displayed by fd hTNFR-1 cDNA fragment phage clone
      selected for binding to goat anti-hTNFR polyclonal
      antibody

<400> SEQUENCE: 10

Ser Cys Ser Asn Cys Lys Lys Ser Leu Glu Cys Thr Lys Leu Cys Leu
1               5                   10                  15

Pro Gln Ile Glu
            20

<210> SEQ ID NO 11
<211> LENGTH: 32
<212> TYPE: PRT
<213> ORGANISM: Artificial Sequence
<220> FEATURE:
<223> OTHER INFORMATION: Description of Artificial Sequence:sequence
      displayed by fd hTNFR-1 cDNA fragment phage clone
      selected for binding to goat anti-hTNFR polyclonal
      antibody

<400> SEQUENCE: 11

Cys His Ala Gly Phe Phe Leu Arg Glu Asn Glu Cys Val Ser Cys Ser
1               5                   10                  15

Asn Cys Lys Lys Ser Leu Glu Cys Thr Lys Leu Cys Leu Pro Gln Ile
            20                  25                  30

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence:sequence
      displayed by fd hTNFR-1 cDNA fragment phage clone
      selected for binding to goat anti-hTNFR polyclonal
      antibody

<400> SEQUENCE: 12

Cys His Ala Gly Phe Phe Leu Arg Glu Asn Glu Cys Val Ser Cys Ser
1               5                   10                  15

Asn Cys Lys Lys Ser Leu Glu Cys Thr Lys Leu Cys Leu Pro Gln Ile
            20                  25                  30

Glu Asn Val Lys Gly Thr
        35

<210> SEQ ID NO 13
<211> LENGTH: 26
<212> TYPE: PRT

```
<213> ORGANISM: Artificial Sequence
<220> FEATURE:
<223> OTHER INFORMATION: Description of Artificial Sequence:sequence
      displayed by fd hTNFR-1 cDNA fragment phage clone
      selected for binding to goat anti-hTNFR polyclonal
      antibody

<400> SEQUENCE: 13

Ser Cys Ser Asn Cys Lys Lys Ser Leu Glu Cys Thr Lys Leu Cys Leu
 1               5                  10                  15

Pro Gln Ile Glu Asn Val Lys Gly Thr Glu
            20                  25

<210> SEQ ID NO 14
<211> LENGTH: 35
<212> TYPE: PRT
<213> ORGANISM: Artificial Sequence
<220> FEATURE:
<223> OTHER INFORMATION: Description of Artificial Sequence:sequence
      displayed by fd hTNFR-1 cDNA fragment phage clone
      selected for binding to goat anti-hTNFR polyclonal
      antibody

<400> SEQUENCE: 14

Cys His Ala Gly Phe Phe Leu Arg Glu Asn Glu Cys Val Ser Cys Ser
 1               5                  10                  15

Asn Cys Lys Lys Ser Leu Glu Cys Thr Lys Leu Cys Leu Pro Gln Ile
            20                  25                  30

Glu Asn Val
        35

<210> SEQ ID NO 15
<211> LENGTH: 45
<212> TYPE: PRT
<213> ORGANISM: Artificial Sequence
<220> FEATURE:
<223> OTHER INFORMATION: Description of Artificial Sequence:sequence
      displayed by fd hTNFR-1 cDNA fragment phage clone
      selected for binding to goat anti-hTNFR polyclonal
      antibody

<400> SEQUENCE: 15

His Leu Ser Cys Gln Glu Lys Gln Asn Thr Val Cys Thr Cys His Ala
 1               5                  10                  15

Gly Phe Phe Leu Arg Glu Asn Glu Cys Val Ser Cys Ser Asn Cys Lys
            20                  25                  30

Lys Ser Leu Glu Cys Thr Lys Leu Cys Leu Pro Gln Ile
            35                  40                  45

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence:sequence
      displayed by fd hTNFR-1 cDNA fragment phage clone
      selected for binding to goat anti-hTNFR polyclonal
      antibody

<400> SEQUENCE: 16

Val Cys Thr Cys His Ala Gly Phe Phe Leu Arg Glu Asn Glu Cys Val
 1               5                  10                  15

Ser Cys Ser Asn Cys Lys Lys Ser Leu Glu Cys Thr Lys Leu Cys Leu
            20                  25                  30

Pro Gln Ile Glu Asn Val Lys
```

-continued

```
<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence:sequence
      displayed by fd hTNFR-1 cDNA fragment phage clone
      selected for binding to goat anti-hTNFR polyclonal
      antibody

<400> SEQUENCE: 17

Ser Cys Ser Asn Cys Lys Lys Ser Leu Glu Cys Thr Lys Leu Cys Leu
 1               5                  10                  15

Pro Gln Ile Glu Asn Val Lys Gly Thr Glu Asp Ser
            20                  25

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence:
      EcoRI/HindIII directional linker

<400> SEQUENCE: 18
gcttgaattc aagc                                                        14
```

EPITOPE-CAPTURED ANTIBODY DISPLAY

CROSS-REFERENCE TO RELATED APPLICATIONS

This application claims the benefit of U.S. Provisional Application No. 60/284,305, filed Apr. 17, 2001, which is incorporated herein by reference in its entirety for all purposes.

BACKGROUND

One of the major goals of current functional genomics research is to establish correlations between gene expression levels and particular cellular states of interest (e.g., disease states, certain developmental stages, states associated with exposure to particular environmental stimuli and states resulting from administration of particular therapeutic treatments). The establishment of such correlations has the potential to provide significant insight into the mechanism of disease, cellular development and differentiation, as well as being of value in the identification of new therapeutics, drug targets and/or disease markers.

Historically, functional genomic studies have focused on mRNA levels in making such correlations. This focus is due in large part because of the generic nature of the methodology for detecting different mRNAs, namely the detection of hybridization between nucleic acid probes and target mRNA molecules. Recent research, however, indicates that often mRNA expression does not correlate well with protein expression, and even less well with protein accumulation or content. Such results are not particularly surprising since many factors affect protein levels independent of transcriptional control, including for example, differences in translational efficiency, turnover rates, whether the protein is compartmentalized or expressed extracellularly, and post-translational modifications. Thus, profiling proteins rather than mRNA is often the preferred approach for conducting functional genomic studies. This is particularly true since proteins are the cellular agents responsible for the catalytic activity of a cell or tissue; hence, by monitoring protein expression, one is able to more directly monitor the actual agents responsible for the biological processes that occur within the cell or tissue.

Various techniques have been utilized in analyzing the protein content of a cell or tissue. Two-dimensional (2-D) gel electrophoresis is one of the more widely utilized techniques for performing such analyses. As the name implies, the method involves separating proteins within a cell or tissue into two dimensions on an electrophoretic separation matrix. The separated proteins are then typically detected by various staining protocols thus yielding a multitude of spots on the gel. If the separation is done under appropriate conditions, the location of the proteins can be used to identify particular proteins, or at least to provide a "fingerprint" of the proteins present in particular cells. There has been a proliferation of protein gel image databases to assist in the identification and comparison of protein levels in different cells and tissues. An example of such a database is the Protein-Disease Database maintained by the National Institutes of Health (NIH). A significant limitation of such methods, however, is the difficulty in identifying the proteins present at each of the spots on a gel.

Phage-display technology is a technology that has been widely utilized in protein analysis. However, this technology has been utilized primarily to produce and screen large libraries of polypeptides to identify polypeptides capable of specifically binding to, particular targets (see, e.g., Cwirla et al., Proc. Natl. Acad. Sci. USA 87:6378–6382 (1990); Devlin et al., Science 249:404–406 (1990); Scott and Smith, Science 249:386–388 (1990); and Ladner et al., U.S. Pat. No. 5,571,698). Phage display methods typically involve the insertion of random oligonucleotides into a phage genome such that they direct a bacterial host to express peptide libraries fused to phage coat proteins (e.g., filamentous phage pIII, pVI or pVIII). Libraries of up to $10^{10}$ individual members can be routinely prepared in this way. Incorporation of the fusion proteins into the mature phage coat results in the peptide encoded by the heterologous sequence being displayed on the exterior surface of the phage, while the heterologous sequence encoding the peptide resides within the phage particle.

The utility of this technology lies in the physical association between the displayed peptide and the genetic material encoding it; this association permits the simultaneous mass screening of very large numbers of phage bearing different peptides. Phage displaying peptides having binding specificity for a particular target can be enriched by affinity screening against the target. The identity of such peptides can be determined from the heterologous sequence contained in the phage displaying the peptide.

Display technology can be utilized to prepare recombinant antibody display libraries for use in the analysis of protein samples. Often such libraries are produced as phage display libraries. Conducting analyses with such libraries is complicated by the fact that in such libraries it is the displayed antibody, rather than the target protein specifically bound by the antibody, that is encoded by the heterologous nucleic acid sequence within the display package (typically a bacteriophage).

Hence, although various methods for conducting certain types of protein analysis have been developed, a significant impediment to analyzing protein expression as a means to gain insight into biological processes is the lack of a generic detection reagent and methodology that is comparable to the ability to use nucleic acid probes in hybridization reactions as detection reagents to detect the presence of complementary nucleic acids.

SUMMARY

A variety of reagents, arrays of polypeptides and methods are provided for analyzing and detecting proteins and for studying protein/protein interactions. In general, the reagents comprise a replicable genetic package that displays a polypeptide encoded by a heterologous segment of a nucleic acid of the package, and a captured multivalent antibody having specific affinity for the displayed polypeptide which is complexed thereto. Because the captured antibody is multivalent, in addition to binding to the displayed polypeptide, the antibody has one or more additional binding sites that are available to bind to a target polypeptide that shares an epitope with the displayed polypeptide. A population of such reagents constitutes a library of antibodies displayed on replicable genetic packages.

These reagents disclosed herein are distinctly different from conventional antibody display libraries. The reagents provided herein have a heterologous nucleic acid segment that encodes the target protein that becomes complexed with a reagent. With conventional polypeptide display libraries, in contrast, a heterologous nucleic acid segment encodes the displayed protein rather than the target protein that forms a complex with the displayed protein (antibody). Consequently, the reagents provided herein, utilized either individually or as collections, can be utilized in a wide variety of methods to detect and identify polypeptides in samples of a variety of different types (e.g., solutions, gel matrices such as one- and two-dimensional electrophoretic gels; and tissue samples). The reagents can also be immobilized on arrays to facilitate certain types of analyses.

Certain methods utilizing such reagents generally involve providing a population of replicable genetic package/antibody reagents such as just described, wherein members of the population comprise a replicable genetic package that displays a first polypeptide encoded by a heterologous segment of a nucleic acid of the package, and the first polypeptide is complexed with a captured antibody having specific affinity for the polypeptide; the first polypeptide and the captured antibody complexed with it varying between at least some of the package/antibody reagents. This population of package/antibody reagents is contacted with a second polypeptide, whereby package/antibody reagents bearing captured antibodies having specific affinity for the second polypeptide bind to the second polypeptide. At least one package/antibody reagent that binds to the second polypeptide is identified. The sequence of the segment of the nucleic acid of the at least one package/antibody reagent and its corresponding amino acid sequence is determined to obtain an indication of an epitope shared by the first and second polypeptides.

With some methods, a population of immunogens is prepared to generate a population of antibodies that are then reacted with a population of replicable genetic packages to form the package/antibody reagents. In some instances, the population of immunogens is a display library, wherein members of the display library include a replicable genetic package that displays one of the polypeptides displayed by the package/antibody reagents. When display libraries are utilized as the immunogen, generally the replicable genetic package of the display library is chosen to be of a different type than the replicable genetic package of the package/antibody reagents.

The package/antibody reagents can also be utilized in arrays. Certain arrays include a support and a plurality of polypeptides immobilized at different locations on the support, wherein there are at least $10^3$ locations/cm$^2$ on the support, each location having at least one of the plurality of polypeptides immobilized therein. The polypeptides in at least some of the locations differ in amino acid sequence and/or another property (e.g., post-translational modification) from polypeptides in other locations. In other arrays, the polypeptides differ in amino acid sequence and/or another property in each of the locations. The polypeptides in certain arrays are antibodies of the package/antibody reagents. The polypeptides in other arrays are proteins that have been captured by the antibody of package/antibody reagents that are immobilized on a support. Some arrays have a higher density of locations, such as $10^4$, $10^6$, $10^8$ or $10^{10}$ locations/cm$^2$, for example. The arrays can have tens, hundreds, thousands, tens of thousands or hundreds of thousands of different polypeptides immobilized to the support.

Other arrays include a support and a plurality of polypeptides immobilized to the support, at least some of the plurality of polypeptides complexed with a captured antibody of a package/antibody reagent. Each of the package/antibody reagents comprise a replicable genetic package that displays a polypeptide, which in turn is complexed to the captured antibody. In certain arrays of this type, the support is a gel or a replica of the gel, and the plurality of polypeptides are located within the gel or on the replica.

Arrays of the package/antibody reagents can be used to conduct a number of different types of analysis. Some methods involve providing an array comprising a support and a plurality of replicable genetic package/antibody reagents immobilized to the support, wherein the package/antibody reagents comprise a replicable genetic package that displays a polypeptide encoded by a segment of a nucleic acid of the package, and the polypeptide is complexed with a captured antibody having specific affinity for the polypeptide, the polypeptide and the multivalent captured antibody complexed with it varying between at least some of the package/antibody reagents. The array is then contacted with a sample containing a mixture of polypeptides, whereby package/antibody reagents bearing captured antibodies having specific affinity for a polypeptide in the mixture capture the polypeptide from the mixture to form a complex. At least one of the complexes is detected. The sequence of the segment of the nucleic acid of the package/antibody reagent within the at least one complex and the corresponding amino acid sequence provides an indication of an amino acid sequence of an epitope on the captured polypeptide.

Methods of preparing various types of arrays are also provided. Certain of these methods involve immobilizing replicable genetic packages displaying a polypeptide to a support. The displayed polypeptides are subsequently contacted with a population of antibodies under conditions such that the antibodies form complexes with displayed polypeptides for which the antibodies have specific binding affinity, whereby the array of polypeptides is formed. When the replicable genetic packages are phage, in some instances the phage are immobilized by plating the phage on a layer of cells to form bacterial microcolonies or an array of microplaques. The microcolonies or micro-plaques are then replicated onto the support, whereby phage displaying polypeptides become immobilized to the support. Other methods involve an additional step in which the array is contacted with a sample containing a plurality of proteins under conditions such that proteins in the sample and antibodies on the array that have specific binding affinity for one another form complexes, thereby forming an array of captured proteins. In some instances, the plurality of proteins in the sample are functional proteins.

BRIEF DESCRIPTION OF THE DRAWINGS

FIG. 3 depicts the deduced protein sequences (SEQ ID NOS: 2–7) displayed by T7 hTNFR cDNA fragment phage clones selected for binding to the goat anti-hTNFR polyclonal antibody. The sequences are aligned with the protein sequence of the hTNFR-1 extracellular domain (SEQ ID NO:1).

FIGS. 7A and 7B show the detection of rhTNFR in a complex mixture of proteins on a Western blot probed with an anti-hTNFR T7 phage-displayed antibody.

FIG. 9 depicts the deduced protein sequences (SEQ ID NOS:8–17) displayed by fd hTNFR cDNA fragment phage clones selected for binding to the goat anti-hTNFR polyclonal antibody. The sequences are aligned with the protein sequence of the hTNFR-1 extracellular domain (SEQ ID NO:1).

FIG. 15A illustrates an array in which a polypeptide is immobilized to a support and is complexed with a captured antibody of a detection reagent that includes a replicable genetic package displaying a display polypeptide that is complexed with the captured antibody. An epitope shared by the immobilized polypeptide and the displayed polypeptide can be determined from a segment of a heterologous sequence in the replicable genetic package that encodes for the displayed polypeptide. FIG. 15B shows an array in which package/antibody reagents (each comprising a replicable genetic package displaying a polypeptide that is complexed with a captured antibody) are immobilized to a support. An epitope of a polypeptide that binds to the captured antibody can be determined from a segment of the heterologous nucleic acid of the replicable genetic package that encodes for the displayed polypeptide. FIG. 15C depicts an array similar to that in FIG. 15B, but the complex immobilized to the support also includes a polypeptide captured by the antibody of the package/antibody reagent. The captured polypeptides in these arrays can be assayed for activity and/or utilized in studies of protein/protein interactions. The identity of an epitope of the captured polypeptide can be determined as described with respect to FIG. 15B.

DESCRIPTION

I. Definitions

Figure 1:
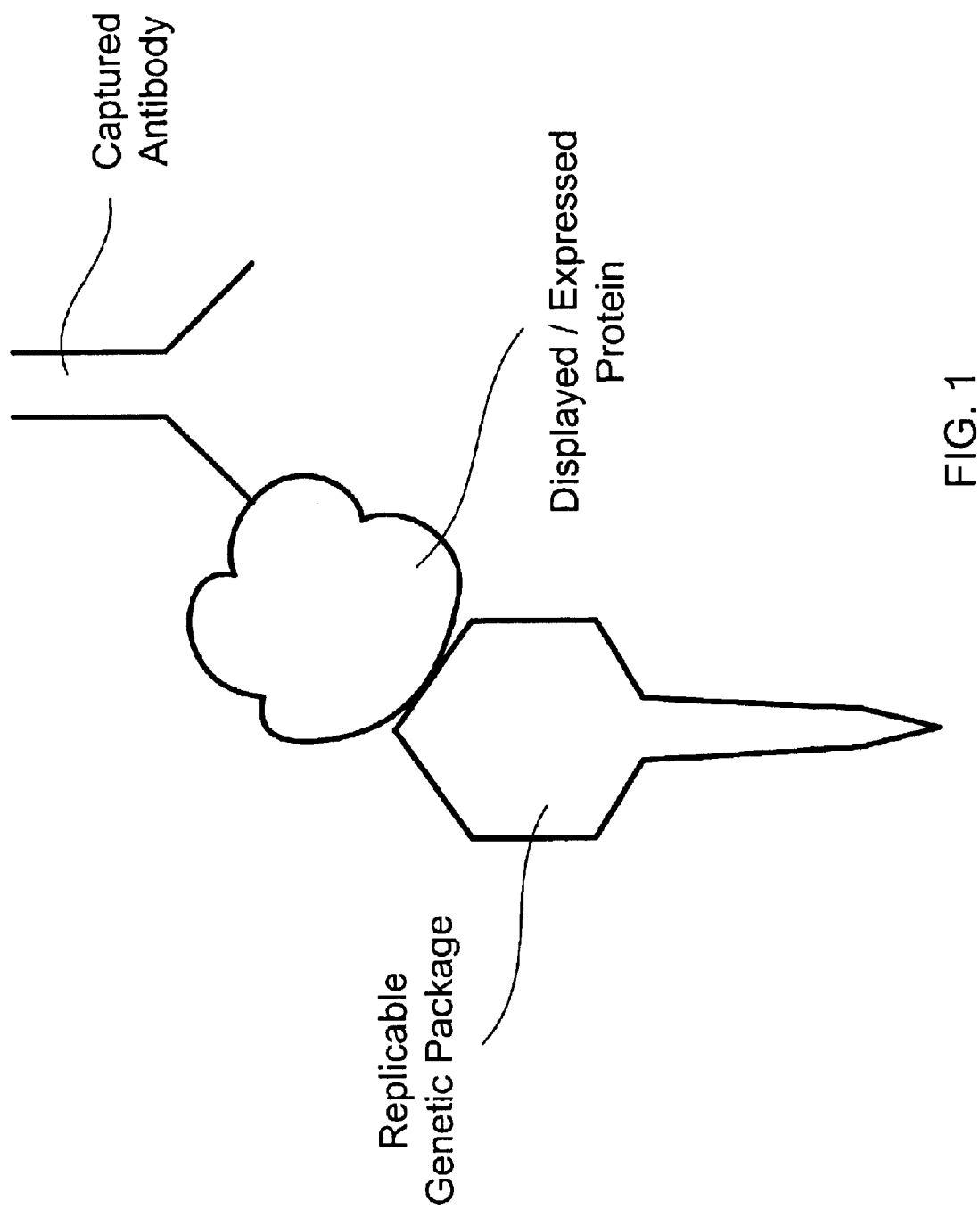
FIG. 1 is a schematic representation of the primary components of certain replicable genetic package/antibody reagents.

The terms "nucleic acid," "polynucleotide," and "oligonucleotide" are used interchangeably and refer to a deoxyribonucleotide or ribonucleotide polymer in either single-, double, or triple-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T. The terms additionally encompass nucleic acids containing known nucleotide analogs or modified backbone residues or linkages, that are synthetic, naturally occurring, and non-naturally occurring and that have similar binding properties as the reference nucleic acid. Examples of such analogs include, without limitation, phosphorothioates, phosphoramidates, methyl phosphonates, chiral-methyl phosphonates, 2-O-methyl ribonucleotides, and peptide-nucleic acids (PNAs).

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. The label attached to the probe can include any of a variety of different labels known in the art that can be detected by chemical or physical means, for example. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. A "target protein" refers to a protein in a sample whose presence is to be detected.

"Conservatively modified variations" or simply "conservative variations" and other similar terms when used to refer to a particular amino acid sequence refer to substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well-known in the art. See, e.g., Creighton (1984) *Proteins*, W. H. Freeman and Company. The terms also refer to individual substitutions, deletions or additions which alter, add or delete a single amino acid or a small percentage of amino acids in an encoded sequence.

An "exogenous molecule" is a molecule that is not normally present in a cell, but can be introduced into a cell by one or more genetic, biochemical or other methods.

Normal presence in the cell is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251.

An exogenous molecule can be the same type of molecule as an endogenous molecule, e.g., protein or nucleic acid (i.e., an exogenous gene), providing it has a sequence that is different from an endogenous molecule. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions.

A "heterologous sequence" or a "heterologous nucleic acid," is one that originates from a source foreign to the particular replicable genetic package, or, if from the same source, is modified from its original form. Thus, a heterologous gene in a prokaryotic replicable genetic package includes a gene that, although being endogenous to the particular host replicable genetic package, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

The term "recombinant" when used with reference to a cell indicates that the cell replicates a heterologous (exogenous) nucleic acid, or expresses a peptide or protein encoded by a heterologous (exogenous) nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "fusion molecule" is a molecule in which two or more subunit molecules are linked, generally covalently. The subunit molecules can be the same chemical type of molecule, or can be different chemical types of molecules. Examples of the first type of fusion molecule include, but are not limited to, fusion polypeptides and fusion nucleic acids.

The term "antibody" as used herein includes antibodies of any multivalent form, including multiple copy display of monovalent antibodies, such as found in replicable genetic packages (e.g., phage) that display scFv fragments. A "multivalent" antibody refers to an antibody that is capable of binding multiple copies of a single antigen or that is capable of binding to two or more different antigens that share an epitope. The antibodies can be obtained from both polyclonal and monoclonal preparations. An antibody consists of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments can be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv") polypeptide is a covalently linked VH::VL heterodimer which can be expressed from a nucleic acid including VH- and VL-encoding sequences either joined directly or joined by a peptide-encoding linker.

Huston, et al. Proc. Nat. Acad. Sci. USA, 85:5879–5883 (1988). A number of strategies for converting the naturally aggregated—but chemically separated light and heavy polypeptide chains from an antibody V region into an scFv molecule that will fold into a three dimensional structure substantially similar to the structure of an antigen-binding site, have been reported. See, e.g. U.S. Pat. Nos. 5,091,513 and 5,132,405 and 4,956,778. Antibodies can also be diabodies, tribodies and tetrabodies.

An "antigen-binding site" or "binding portion" refers to the part of an immunoglobulin molecule that participates in antigen binding. The antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

The term "epitope" refers to the portion of an antigen that interacts with an antibody. More specifically, the term epitope includes any protein determinant capable of specific binding to an immunoglobulin or T-cell receptor. The phrase "shared epitope" and other related phrases means that two or more polypeptides present an epitope that is specifically recognized by the same antibody. In some instances the amino acid sequence of the epitope of such polypeptides is identical; in other instances, however, the amino acid sequence of the epitope presented by the polypeptides varies slightly, in some instances by only one or two amino acids. The phrase can also refer to continuous or discontinuous epitopes in which the primary sequence (i.e., the amino acid sequence) is not similar but nonetheless the epitopes are still recognized by the same antibody.

The phrases "specifically binds," "specific binding affinity" (or simply "specific affinity"), "specifically recognize," and other related terms when used to refer to binding between a protein and an antibody, refers to a binding reaction that is determinative of the presence of the protein in the presence of a heterogeneous population of proteins and other biologics. Thus, under designated conditions, a specified antibody binds preferentially to a particular protein and does not bind in a significant amount to other proteins present in the sample. An antibody that specifically binds to a protein has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

Reference to a polypeptide being "displayed" on a replicable genetic package means that the polypeptide is attached to a group (e.g., an amino acid residue) located at an exterior surface of the replicable genetic package.

An "array" broadly refers to an arrangement of agents (e.g., proteins, antibodies, replicable genetic packages) in positionally distinct locations on a substrate. In some instances the agents on the array are spatially encoded such that the identity of an agent can be determined from its location on the array. A "microarray" generally refers to an array in which detection requires the use of microscopic detection to detect complexes formed with agents on the substrate. A "location" on an array refers to a localized area on the array surface that includes agents, each defined so that it can be distinguished from adjacent locations (e.g., being positioned on the overall array, or having some detectable characteristic, that allows the location to be distinguished from other locations). Typically, each location includes a single type of agent but this is not required. The location can have any convenient shape (e.g., circular, rectangular, elliptical or wedge-shaped). The size or area of a location can vary significantly. In some instances, the area of a location is greater than 1 $cm^2$, such as 2–20 $cm^2$, including any area within this range. More typically, the area of the location is less than 1 $cm^2$, in other instances less than 1 $mm^2$, in still other instances less than $0.5^2$ mm, in yet still other instances less than 10,000 $\mu m^2$, or less than 100 $\mu m$.

An "electrophoretic separation matrix" refers to any matrix in which components of a sample are electrophoretically separated. Typically, components include a plurality of polypeptides in a polypeptide sample which is being analyzed. Such matrices can include various types of solutions and gels. Examples of such matrices include, but are not limited to, polyacrylamide, agarose and cellulose.

A "tissue" refers to an aggregation of cells united in performance of a particular function. The tissue can be part of a living organism, a section excised from a living organism, or can be artificial. An artificial tissue is one in which the aggregation of cells are grown to function similar to a tissue in a living organism. The aggregated cells, however, are not obtained from a host (i.e., a living organism). Artificial tissues can be grown in vivo or in vitro.

A "label" refers to an agent that can be detected by using physical, chemical, optical, electromagnetic and/or other methods. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

II. Overview

Described herein are methods and reagents that can be utilized to analyze the composition of complex protein mixtures, including detecting the presence of one or more particular proteins in a mixture of proteins. More specifically, the reagents include a replicable genetic package (or simply package) having a heterologous nucleic acid that encodes a polypeptide that is displayed on an exterior surface of the replicable genetic package. The displayed polypeptide is complexed to an antibody (or plurality of antibodies) that has specific binding affinity for the displayed polypeptide. Thus, the general overall structure of the reagent is package (carrying the heterologous nucleic acid segment)/expressed protein/captured antibody (see FIG. 1).

The antibody or antibodies complexed to the replicable genetic package are able to bind a plurality of polypeptides. Thus, while some of the binding sites of the multivalent antibody are bound to the expressed polypeptide, the other site(s) on the antibody (antibodies) is (are) available to bind to a polypeptide (the target polypeptide) that shares an epitope with the expressed polypeptide. In many instances, the expressed polypeptide and the polypeptide bound by the complexed antibody are the same (i.e., have the same primary sequence). In other instances, the epitope on the expressed polypeptide and the polypeptide bound by the antibody have slightly different amino acid sequences. Such differences often involve variation in only one or two amino acids. In some instances, the differences involve conservative variations.

Hence, a population of such reagents constitutes a library of antibodies displayed on replicable genetic packages. The significance of such a library is that each replicable genetic package of the library carries a heterologous nucleic acid segment that encodes an amino acid sequence that correlates with the epitope recognized by the antibody displayed on the package. Said differently, each package in such a library is a ligand of the protein encoded by the heterologous nucleic acid carried by the package. As just described, this is the case because the open binding site(s) on the displayed antibody (antibodies) can bind to one or more additional copies of a protein having a epitope that is shared with the protein expressed on the replicable genetic package, and often binds to a protein having the same primary sequence. A library of reagents having this arrangement can be considered an "anti-proteome," because the reagents within the library can specifically bind to all or a portion of the proteins within a cell or tissue of interest. The power of such an arrangement is that it permits the immediate identification (by primary sequence) of target proteins in a wide variety of sample types, including, but not limited to, gels, cells, tissues and protein arrays.

Such reagents are distinctly different from the complexes in conventional recombinant antibody display libraries. With the present reagents, the heterologous nucleic acid segment carried by the package encodes the target protein; in contrast, with conventional display libraries, the segment encodes the displayed antibody rather than the protein complexed to the antibody. Consequently, the individual reagents and libraries disclosed herein can be utilized as a general reagent in a wide variety of methods for determining the identity of polypeptides, even in complex mixtures. As such, the reagents have broad applicability to protein biochemistry and cell biology, as well as functional genomics and proteomics.

For example, the reagents can be utilized to determine the primary sequence of any, and in some instances all, of the proteins in samples obtained from tissues, cells or subcellular compartments. The reagents can also be utilized to identify proteins in one- and two-dimensional separation matrices, thereby significantly expanding the utility of such established analytical techniques. The reagents can also be used in preparing and subsequently utilizing a wide variety of protein arrays, including arrays having unknown proteins and arrays having known proteins in unknown locations.

Additionally, the ability to utilize the reagents to obtain qualitative and quantitative information means that the methods are amenable to a variety of screening, comparative and diagnostic studies. For example, the methods can be utilized to develop comparative protein expression data. Such comparative studies can be utilized to identify markers of specific diseases, potential targets for pharmaceuticals and/or drug candidates. Once markers that are selectively expressed in certain disease states, for example, are identified, the methods and reagents can be utilized to conduct diagnostic applications. Additionally, the methods and reagents can be used to develop protein databases that include, for example, identity and relative abundance information for proteins in different cells, tissues or cellular states. Thus, the methods and reagents can be utilized in differential expression analyses. The methods and reagents also find utility in studies on structure/activity relationships and in metabolic engineering investigations in which one genetically modifies a certain gene and then determines what effects such a modification has on cellular protein expression. The reagents can additionally be used to prepare microarrays, that in turn can be utilized in both qualitative and quantitative analyses.

III. Reagent Preparation and Use

A. Reagent Composition

As illustrated in FIG. 1, the replicable genetic package/antibody reagents (or simply "package/antibody reagents or reagents) in general include: (i) a replicable genetic package, (ii) a polypeptide displayed/expressed by the replicable genetic package, (iii) a heterologous nucleic acid that includes a segment that encodes the displayed polypeptide, and (iv) one or more antibodies ("captured antibodies") having specific affinity for, and complexed to, the displayed polypeptide. The replicable genetic packages often are utilized as libraries in which members of the library differ with respect to the displayed polypeptide and the antibody (or antibodies) that are complexed to the displayed polypeptide.

1. Replicable Genetic Packages

Replicable genetic packages (or simply packages) of various types can be utilized in the package/antibody reagents. In general, a replicable genetic package refers to a biological complex comprising a nucleic acid, and at least one peptide encoded by the nucleic acid. Examples of replicable genetic packages include cells, spores, bacteria, viruses, bacteriophage and polysomes. Replicable genetic packages are also capable of replication either by self-replication, in combination with a host and/or a helper virus, or by in vitro replication, transcription and expression. The replicable genetic package can be either prokaryotic or eukaryotic. Collections of package/antibody reagents can be selected from any one of the foregoing and include different combinations thereof.

Bacteriophage including phagemids are often utilized as the replicable genetic package, especially filamentous phage (e.g., M13, fd and fl) and phagemid vectors derived therefrom. See, e.g., Dower, WO 91/19818; Devlin, WO 91/18989; MacCafferty, WO 92/01047; Huse, WO 92/06204; and Kang, WO 92/18619. Other phage of *E. coli*, such as T7 phage, or phage of other bacterial species can also be used. Filamentous phage are generally 6 nm in diameter and up to one micron in length. Such phage have been used extensively in peptide phage display. The surface of such phage consists of five coat proteins, two of which, pIII and pVIII, have been used to display peptide libraries. pIII contains 406 amino acids and is present in three to five copies. The major coat protein, pVIII, which contains 50 amino acids, constitutes the bulk of the phage protein as it is present in approximately 2700 copies. The bacteriophage can also be a non-filamentous phage such as icosahedral phages T7 and lambda. The major coat protein of T7 phage is the gene 10 capsid protein, which contains 370 amino acids and is present in 415 copies.

In addition to phage, the replicable genetic package of the invention can include eukaryotic viruses, (e.g., the Moloney murine leukemia virus; see, e.g., Han, et al. (1995) Proc. Natl. Acad. Sci. USA 92:9747–9751) or spores (e.g., spores from *B. subtilis*; see, e.g., Donovan, et al. (1987) J. Mol. Biol. 196:1–10). A variety of different cells can also be used as replicable genetic packages in the present invention. Examples of suitable bacterial cells include, but are not limited to, *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli*.

Other replicable genetic packages are polysomes. A polysome is a combination of a segment of mRNA with ribosomes attached to the mRNA, the ribosomes also binding a segment of a nascent polypeptide extending from the ribosomes. Such complexes are similar to phage display particles in that a heterologous nucleic acid segment that encodes a polypeptide and the polypeptide encoded by the segment are attached to one another. Polysomes are discussed further, for example, in U.S. Pat. No. 5,922,545.

In some instances, replicable genetic packages are considered to be of different types when the packages are of different classes, such as a virus versus a spore, or a virus versus a cell. Replicable genetic packages can also be of different types even if from the same class but of a different subclass. For example, different filamentous bacteriophage can be considered to be different types (e.g., M13 versus Fd versus fl). Different Fd phage displaying different polypeptides, however, would not be considered different types of packages because in both instances the package is an Fd phage. Different types of replicable genetic packages can be selected such that the different types are not immunologically cross reactive (i.e., antibodies that specifically bind to one type of package do not also complex with packages of another type).

2. Displayed Polypeptide

The polypeptide expressed and displayed by the replicable genetic package can vary widely and can include any length capable of being displayed on a replicable genetic package, including both fragments and full length proteins, for example. The size of the displayed polypeptide depends in part on the number of different epitopes one wants displayed by the package. In general, the displayed polypeptide can include just enough amino acids to present a single epitope but can extend in size up to a full length expressed cDNA. Thus, for example, the displayed polypeptides can include as few as 4, 5 or 6 amino acid residues but extend up to hundreds or even thousands of amino acid residues. The displayed polypeptides in certain applications include at least 4, 5 or 6 amino acid residues, and less than 100 residues, but other sized polypeptides can be displayed. In some instances, the displayed polypeptides are 10, 20, 30, 40, 50, 60, 70, 80, 90 or 100 residues in length, or any integral number of amino acids within these ranges. Typically, the displayed polypeptide includes 6 to 20 amino acids. By utilizing libraries in which the expressed polypeptide is 6–10 amino acids in length, one can generate libraries having continuous epitopes (i.e., epitopes lacking significant secondary or conformational structure resulting from interactions between amino acids in the polypeptide). Libraries displaying larger polypeptides can be utilized to generate conformational or discontinuous epitopes that do have secondary structure.

Certain package/antibody reagents display random populations of peptides. Such libraries are typically designed to produce packages that display polypeptides in which some or all of the positions of the polypeptide are systematically varied for the different amino acids. Random peptide coding sequences can be formed by cloning and expression of randomly-generated mixtures of nucleic acids in the appropriate recombinant vectors (see, e.g., Oliphant et al. (1986) Gene 44:177–183). Other libraries are formed by producing variants from a starting framework polypeptide. In this approach, a starting polypeptide is utilized as a framework and selected residues are varied. Such polypeptides can be formed by mutagenizing the starting nucleic acid by insertion of mutagenic cassettes or error-prone PCR, for example (see, Lardner et al., WO 88/06630).

3. Antibody Complexed to Displayed Polypeptide ("Captured Antibody")

The antibody or antibodies complexed to the displayed polypeptide can be any multivalent form. As used herein, the term "multivalent" antibody means that the antibody or antibodies can form a complex with the polypeptide displayed on the replicable genetic package and one or more copies of a target protein. Thus, the antibody can be a single antibody with a plurality of binding sites. Alternatively, the captured antibody or antibodies can include monovalent antibodies, provided such antibodies are displayed in a multivalent format. One such example is a plurality of monovalent antibodies that are captured by a multivalent antibody. Thus, for example, multiple scFv antibodies can be captured on the prongs of another antibody (e.g., a scFv captured on an IgG antibody). Another example of multivalent display of a monovalent antibody is the display of scFvs on phage, as phage present multivalent display. The antibodies can also be diabodies, tribodies and tetrabodies.

The antibodies can be polyclonal populations of immunoglobulins from any convenient species, monoclonal antibodies (derived from mice for example) and recombinant antibody populations as produced in display systems such as phage display and diabodies.

B. Reagent Preparation

The replicable genetic package/antibody complexes can be formed according to a number of different protocols depending upon the starting components utilized. The following steps, however, illustrate one approach for preparing the package/antibody reagents beginning with replicable genetic packages that do not yet contain a heterologous sequence. In general, the process involves: (i) producing a cDNA display library by preparing a population of replicable genetic packages that each display different polypeptides; (ii) preparing an antibody population; and (iii) and incubating the antibody population with the cDNA display library under conditions such that antibodies that have specific binding affinity for a displayed protein form a complex.

1. Preparation of cDNA Display Library

One of the initial steps involves preparing cDNA molecules from a cell or tissue of interest and subsequently cloning these cDNA molecules or fragments thereof into the genome of a replicable genetic package to produce a library of displayed polypeptides that is at least partially, if not completely, representative of the expressed polypeptide population of the starting cells or tissue. In particular, expression of the resulting nucleic acid fusion generates a fusion protein composed of the polypeptide encoded by the heterologous segment and an endogenous protein which, upon its transport and assembly at an outer surface of the package, results in the display of an exogenous polypeptide from an exterior surface of the package.

Thus, for example, nucleic acid libraries frequently are cloned into the genes for pIII or pVIII using standard cloning techniques to form a fusion gene. Expression of the resulting construct produces a fusion protein that includes the display protein, the pIII or pVIII protein or fragment thereof, and a signal sequence (typically from a secreted protein). Often the heterologous sequences are inserted into or near the N-terminus of the gene encoding pIII or pVIII, but this is not required and other sites can be utilized. The heterologous nucleic acids, including optional flanking spacers, are inserted into the genome utilizing established recombinant techniques (see, e.g., Sambrook et al. (1989) Molecular Cloning: A Laboratory Manual, 2nd Ed., Cold Spring Harbor Laboratory Press, Cold Spring Laboratory, N.Y.) and according to the methods disclosed in the other references listed supra in this section.

Certain filamentous phage vectors can be designed to produce multiple copies of either the gene for pIII or pVIII. With such vectors, heterologous nucleic acids are inserted into only one of the copies; expression of the other copy dilutes the proportion of fusion protein incorporated into the phage and can be useful in reducing selection against polypeptides that reduce phage growth. Another technique involves cloning the heterologous sequences into phagemid vectors that encode phage coat proteins and include packaging sequences but which are incapable of self-replication. Such phagemids can be transfected into cells that are also infected with helper phage that package the phagemids (see, e.g., Garrard, WO 92/09690). In certain other instances, a T7 vector is utilized to display 10–20 copies of the polypeptide expressed by the inserted nucleic acid (i.e., cDNA), which corresponds to approximately one copy of the displayed polypeptide on each face of the icosahedral phage particle.

The cDNA molecules or expressed sequence tags (ESTs) cloned into the genome of the replicable genetic packages can be prepared by most conventional means. The present methods do not require full length cDNA because function is not required, only that each fragment be sufficiently long to contain at least one epitope (see size considerations listed supra). Often it is desired that most of the cDNAs are large; however, in other instances, a library of smaller cDNA fragments, each containing relatively fewer epitopes per clone, is useful.

In general, cDNA preparation methods that do not systematically favor the isolation of any particular region of the cDNA (randomly-primed reverse transcription, for example) are preferred. This increases the diversity of epitopes available in the library. In some instances, normalizing the cDNA population (see infra) to decrease the difference in the representation of the most and least abundant mRNAs is desired, although usually not required. In addition, cDNA segments can be constructed by oligonucleotide synthesis, from expressed sequence tags listed in publicly or privately available sequence databases. A universal human EST library can be constructed to create a universal human anti-proteome. Libraries of random peptides can also be used as the antibody capture reagent (see the following section).

2. Antibody Preparation

Numerous formats are available to prepare the antibodies that are complexed to the displayed protein(s) expressed on the exterior surface of the replicable genetic packages. In general, one prepares a collection of polypeptides and utilizes the collection as the immunogens to produce the desired antibodies. In some instances, the protein collection is used to immunize an animal (e.g., a rabbit) to produce a polyclonal antibody collection. Alternatively, the protein collection can be used in conjunction with established hybridoma technology to generate a population of monoclonal antibodies. Still another option is to prepare the antibodies as part of recombinant display libraries.

Methods for preparing antibodies are discussed, for example, in Kohler, G. et al. (1975) Nature 256:495–496; Clausen H. et al. (1985) Biochem. 24:6190–6194; Harlow and Lane (1988) Antibodies: A Laboratory Manual. Cold Spring Harbor Laboratory, New York; and Goding, J. W. (1983) "Monoclonal Antibodies: Principles and Practice, Production and Application of Monoclonal Antibodies," in Cell Biology, Biochemistry and Immunology, Academic Press Inc., Victoria, pp. 56–86).

The population of proteins utilized as the immunogen can be of a variety of different types. One option is to obtain a protein fraction from the same cells or tissue utilized to generate the cDNA molecules used to prepare the cDNA display library. This protein fraction can contain all of the proteins expressed in the cells or tissues, or some subset thereof. Using such a collection of proteins, one obtains a population of antibodies that are reactive with all or most of the proteins within the cells or tissue of interest.

Another option is to utilize a display library such as the cDNA display library just described supra as the immunogen in any of the antibody producing formats that are available. Thus, the display library used to immunize an animal displays the same or many of the polypeptides displayed by the cDNA library. In some instances, the replicable genetic packages of the display library utilized as the immunogen are of the same type as in the cDNA library. More typically, however, the replicable genetic packages of the display library are of a different type then those of the cDNA library. The use of different types of replicable genetic packages (e.g., different types of phage) minimizes the potential problem of generating antibodies against the replicable genetic packages which could subsequently complex to the replicable genetic package in the cDNA library rather than the polypeptide displayed on the package.

Thus, for example, a display library in which the polypeptides are displayed on filamentous phage can be used as the immunogen to produce an antibody population reactive with the polypeptides displayed on the filamentous phage. This antibody population can then be incubated with a cDNA display library in which the same display polypeptides are expressed on T7 phage under conditions such that the displayed proteins on the T7 phage capture the antibodies generated using the filamentous phage display library as the immunogen.

The immunizing library can also be expressed as part of a fusion library, such as part of a fusion library to glutathione-S-transferase (GST), for example (see Example 7 infra). For instance, the cDNA used to generate the cDNA display library can additionally be inserted into a vector such that the cDNA is expressed as part of a fusion to GST. The resulting fusion proteins can be isolated on a glutathione column and then eluted. The eluted fusion proteins can then be utilized as immunogens. Alternatively, the fusion proteins can be complexed with beads that bear glutathione and the resulting beads bearing the fusion proteins utilized as an immunogen, as such bead-borne immunogens have sometimes been found to be more immunogenic.

Other methods involve cloning random peptide coding sequences into appropriate vectors to form a random population of peptides (see, e.g., Oliphant et al. (1986) Gene 44:177–183). The displayed polypeptides in certain of these random libraries are 6–10 residues in length but can be up to 20 to 50 or more residues in length. Such a library can be considered an "universal immunogen." Antibodies produced from such a display library can then be captured by polypeptides that are displayed as part of a cDNA library prepared from a cell type or tissue of interest, with the replicable genetic packages of the cDNA library typically differing in type from those used to create the random display library. As noted supra, however, the replicable genetic packages of the immunogen and the cDNA display library can in some instances be the same type.

3. Combining cDNA Display Library and Antibodies

By mixing the cDNA display library with the population of antibodies, a library of replicable genetic package/antibody reagents is formed. Conditions for this step are chosen to encourage the formation of complexes between the antibodies and the replicable genetic packages. Generally the density of the displayed polypeptides is low (e.g., approximately 1 copy per 1000 nm² of package surface). Consequently, even though the antibodies are multivalent (see supra), typically each antibody only binds to a single copy of the polypeptide displayed on the exterior surface of the package. This leaves the other binding site(s) on the antibody free to bind to a target polypeptide in a sample that shares an epitope with the polypeptide displayed on the surface. Thus, for example, in the case of libraries in which the packages are T7, each captured antibody typically has at least one free binding site.

Icosahedral phage vectors are chosen to display approximately 1 copy of the expressed polypeptide per phage particle, or 10 to 20 copies per phage particle (approximately 1 copy of the expressed polypeptide per face of the icosahedron), hence there are approximately 1, or from 10 to 20, respectively, free antibody binding sites (per phage) that are available for binding to target polypeptides in solution. Mixing of the T7 cDNA library with the antibody population generates a library of T7 phage that each display a polypeptide (i.e., display polypeptides) and an antibody or antibodies that have specific binding affinity to various epitopes on each of the displayed polypeptides.

The antibodies borne by any particular package can sometimes be a population of different antibodies. For example, the antibodies complexed to a package can be a collection of different antibodies to any single epitope. Moreover, in some instances, a package may bear a plurality of antibodies recognizing several different epitopes displayed by the expressed polypeptide. The diversity of the antibodies can be controlled to some extent by the size, and therefore the number of potential epitopes encoded, of the displayed polypeptides.

With other applications, such as applications requiring the highest of antibody specificities, a single polypeptide rather than a plurality of polypeptides is displayed on the surface of the replicable genetic package (a monovalent display format; this format in which a single polypeptide is displayed on a package should not be confused with a monovalent antibody which is an antibody that has a single binding site). Examples of monovalent formats that can be utilized include, but are not limited to, fd phagemid pIII vectors, T7 low level expression vector, and some polysome/ribosome display formats. cDNA products displayed in a monovalent format favor the capture of the highest affinity (and typically more specific) antibodies. Such reagents place the highest stringency on binding of the captured antibodies to the immobilized target proteins; increased stringency also disfavors cross-reactivity of displayed antibodies with polypeptide sequences that differ only slightly from the principle antigenic epitopes.

Under certain conditions, an antibody or antibodies on one package can become specifically cross-linked to polypeptides displaying the same epitope(s) on other packages, thereby forming epitope-specific aggregates. Such aggregates can be useful in some applications, such as applications requiring higher antibody valency. Aggregation is usually favored by extending the incubation time to allow like complexes to specifically cross-react.

As indicated above, the antibodies of the reagent typically are multivalent but can be monovalent if displayed in a multivalent format. One example of how a library of such reagents can be prepared is as follows. Initially, a population of proteins is used to immunize an animal (e.g., a mouse) to generate a population of antibodies as described above. The spleen of the animal is then removed, mRNA is extracted, reverse transcription and amplification of heavy and light antibody chain cDNAs is performed. The resulting heavy and light chain fragments are cloned into the appropriate antibody display vectors to express single chain Fv or Fab forms on the phage coat proteins, thereby creating a library of many Ab specificities. These two libraries can be mixed to form a library in which monovalent scFv antibodies are displayed in a multivalent format. A separate cDNA library of the expression products of a tissue of interest is also prepared; and the two libraries are mixed to form the epitope-captured antibody display library. Typically, the phage in the antibody library differ in type from those of the target tissue cDNA library (e.g., filamentous phage versus T7 phage). In this format, recovery of the bound complex provides clones of the target cDNA and of the target-specific antibodies; thus allowing the identification of the sequences of both the cDNA and the antibodies.

The size of the library in terms of number of members can vary significantly. In fact, the reagents can be utilized individually. For example, individual reagents can be prepared according to the foregoing methods that have specific binding affinity for any particular polypeptide of interest, provided at least some portion of the primary sequence of the polypeptide is known. Many applications, however, utilize libraries or panels of reagents, each member being specific for one of the many individual polypeptides in a tissue, cell or other complex mixture of polypeptides, even if some or all of the polypeptides are of unknown primary sequence. Smaller libraries designed to detect the presence of a limited number of target polypeptides often have 5–10 members, and sometimes more, such as 20, 30, 40 or 50 members, or any integral number therebetween. Larger libraries that are utilized to probe complex protein samples can include a very large number of members, such as $10^2$, $10^3$, $10^4$, $10^5$, $10^6$, $10^7$, $10^8$, $10^9$ or $10^{10}$ or any integral number therebetween. Even larger libraries can be produced, especially where small cDNA fragments containing a few epitopes each are prepared, including up to $10^{11}$ to $10^{12}$ members in phage and $10^{12}$ to $10^{15}$ members in polysomes, or any integral number therebetween.

C. Detection and Target Protein Identification

1. Labeled Target Proteins

One option is to label the proteins in the sample before the protein sample is contacted with the package/antibody reagents. Reagents that are complexed to target proteins can then be detected from the signal generated by the labeled target protein.

2. Separation of Bound and Unbound Reagents

Certain analyses are conducted by contacting a sample potentially containing target proteins with a population of package/antibody reagents under conditions such that reagents specifically bind to target proteins having an epitope that is recognized by the captured antibody of the reagent. Unbound reagents are then selectively separated from target protein/reagent complexes. Reagents that have formed complexes with the target can then be collected, nucleic acids removed from the packages, and the nucleic acid segments sequenced to determine the identity of an epitope one of the target polypeptides. Often such separations are performed by attaching proteins within the sample to a support, contacting the immobilized sample with the reagents and then washing away unbound reagents.

3. Detection Reagents

Other detection approaches utilize various labeled detection reagents that have specific affinity for a particular target protein. For instance, labeled antibodies that specifically bind to certain target proteins can be utilized to detect proteins bound to package/antibody reagents. In a modified version of this approach, unlabeled antibodies that specifically bind to target proteins are used and detection is accomplished using labeled antibodies that specifically bind to the unlabeled antibodies that have formed a complex with a target protein. A potential problem associated with either of these two approaches is cross-reactivity of the detection reagent with the polypeptide displayed by the package of the package/antibody reagent. However, the antibodies are expected to preferentially bind to the captured polypeptide rather than the displayed polypeptide because of the relative inaccessibility of the displayed polypeptide (sandwiched between a package and capture antibody) as compared to the captured polypeptide (bound only to the capture antibody).

Alternatively, the detection reagent can be composed of a replicable genetic package that displays a polypeptide at its surface, a detection antibody that specifically binds to the display polypeptide, and a label. The package of a detection reagent displays one of the same polypeptides as displayed by one of the packages of the package/antibody reagents brought into contact with the protein sample. Thus, the package of the detection reagent includes a copy of the same heterologous nucleic acid segment as one of the package/antibody reagents (i.e., the segment that encodes the polypeptide displayed by the two types of reagents). Thus, package/antibody reagents and detection reagents sharing this feature, bear captured antibodies and detection antibodies, respectively, that have specific binding affinity for the same target polypeptide. A component of the detection reagent is labeled to facilitate detection. Typically, the package is labeled to minimize the possibility that the label interferes with the ability of the detection antibody to bind to a target protein. The problem of cross-reactivity described supra is lessened with this type of detection reagent because the bulk of these reagents impede their ability to gain access to the polypeptide displayed by one of the package/antibody reagents. Consequently, these reagents offer better selectivity than the foregoing detection reagents.

In use, a detection reagent bearing a detection antibody that recognizes an epitope on a target protein captured by one of the package/antibody reagents, forms a complex that contains: (i) the package/antibody reagent, (ii) the captured protein, and (iii) the detection reagent. Because the package of the package/antibody reagent and the detection reagent both include the same nucleic acid segment, the sequence of the segment from either package can be sequenced to determine an amino acid sequence that includes an epitope on the target polypeptide.

The second phage complex (i.e., the complex of the detection reagent) can be a different phage. Alternatively, detection can be accomplished with a "fusion protein captured" antibody display reagent. An example is a GST-cDNA expression product fusion, mixed with an antibody collection to capture one binding site of an antibody. This reagent, while not a replicable genetic package useful for identifying the target, can serve as a detection reagent for locating the target in an array, for example.

Given the similarity in composition, the preparation of such detection reagents closely parallels the preparation of the package/antibody reagents. For example, one typically prepares detection reagents of this type by initially preparing a cDNA display library and a population of antibodies according to the methods described in sections III.B.1 and 2. Then, usually prior to contacting members of the display library with the antibody population, members of the display library are labeled. In certain instances, this is accomplished by labeling the packages of the display library either by covalent attachment or using labeled antibody that binds to the package (i.e., labeled anti-package antibody). A fluorescent label is often utilized but other detectable labels can be used as well (see the detection section infra). The members of the labeled display library are then incubated with the antibody population to form a collection of detection reagents. The resulting detection reagents are essentially identical to the package/antibody reagents described above, except that the detection reagents bear a label whereas the package/antibody reagents do not.

However, as noted above, a fusion protein captured antibody display reagent can also be utilized as a detection reagent. Thus, a GST-cDNA expression product fusion mixed with an antibody collection to capture one binding site of an antibody is one specific example. Such reagents can be useful in locating a target in an array for example.

Even though the capture antibody of the package/antibody reagent and the detection antibody of the detection reagent recognize the same target protein, both the package/antibody reagent and the detection reagent can bind to the same copy of the target protein because the two types of antibodies recognize different epitopes on the same protein. Nonetheless, as noted above, package/antibody reagents and detection reagents that bind to the same target protein share a common nucleic acid segment (namely, the segment that encodes for the same polypeptide displayed on both types of reagents). Consequently, the amino acid sequence of an epitope of the target can be determined by sequencing the nucleic acid segment from either the package/antibody reagent or the detection reagent.

4. Identification

Once package/antibody reagents that have formed complexes with a target protein have been detected, the captured target protein can be identified. Generally, this involves removing the nucleic acid, or at least the segment encoding the displayed polypeptide, from the package of a package/antibody reagent. The nucleic acid or segment is then usually amplified using known techniques and then sequenced, typically with commercial sequencing instruments.

D. Applications

The individual package/antibody reagents or libraries of package/antibody reagents can be utilized to detect the presence of a relatively small number or very large number of target proteins in diverse sample types. The reagents can be used to probe protein-containing solutions or other types of matrices that include proteins. As indicated in the Background section, a common practice in proteomics applications is to at least partially resolve complex protein mixtures into component proteins by gel electrophoresis, especially multiple dimensional electrophoresis (e.g., two-dimensional electrophoresis). The package/antibody libraries disclosed herein can be utilized to detect and identify the proteins in the different locations on the gel.

For example, using the methods described above, one can prepare a library of package/antibody reagents that have specific binding affinity to the proteins within a cell or tissue under investigation. The cells or tissue used to prepare such a library are also processed to obtain a total protein fraction that includes all of the expressed proteins in the cell or tissue of interest (of course, a subset of such proteins such as from a particular subcellular compartment can also be probed).

The proteins in this fraction are applied to a gel and separated into many different spots (often thousands) that is typical of two-dimensional electrophoretic formats. Various electrophoretic methods can be used in combination to achieve separation. Examples of such methods include, but are not limited to, zone electrophoresis (separation of proteins on the basis of their intrinsic charge-to-mass ratio), isoelectric focusing electrophoresis (proteins separated according to their isoelectric points) and gel electrophoresis methods that separate on the basis of size. Such methods are discussed, for example, by Hochstrasser, D. F., et al. (1988) Anal. Biochem. 173:424; O'Farrell, P. H. (1975) J. Biol. Chem., 250:4007; and Anderson, N. G. and Anderson, N. L. (1996) Electrophoresis 17:443. In many applications, proteins are separated in one dimension and then the gel partially rotated to achieve further electrophoretic separation of the proteins. For example, certain protein separation procedures involve iso-electric focusing along a first dimension followed by SDS-PAGE electrophoresis along a second dimension. See, e.g., Hames et al, 1990, Gel Electrophoresis of Proteins: A Practical Approach, IRL Press, New York; Shevchenko et al., 1996, Proc. Natl. Acad. Sci. USA 93:1440–1445; Sagliocco et al., 1996, Yeast 12:1519–1533; Lander, 1996, Science 274:536–539.

The proteins in each spot can be rapidly detected and identified with the library of reagents prepared from the cells or tissue. One detection option involves excising individual spots (or a small number of spots) from the gel, eluting the proteins within the spot(s) from the excised section and subsequently transferring the eluted protein(s) onto some type of support. A variety of different supports can be utilized including, but not limited to, glass, cellulose sheets, and various membranes (e.g., nylon, and polyvinylidene difluoride (PVDF)). The immobilized protein is then "stained" by incubation with the package/antibody library, followed by washing to remove unbound and non-specifically-bound package/antibody reagents. Packages that remain bound to the support are recovered by elution with an appropriate solution. One suitable wash solution is one of low pH. Filamentous phage are stable to pH 2.2 (glycine buffer) for 10 minutes at room temperature. T7 phage are less stable to low pH so an elution buffer of 1%SDS in PBS is generally used. The nucleic acids of those replicable genetic packages eluted from the support are subsequently amplified and the nucleic acid (or segment thereof) that encodes the displayed polypeptide is sequenced. Translation of this nucleic acid sequence to an amino acid sequence provides a portion of the sequence of the immobilized protein, thus identifying the protein(s) present in the section of the gel that was removed.

Figure 15A:
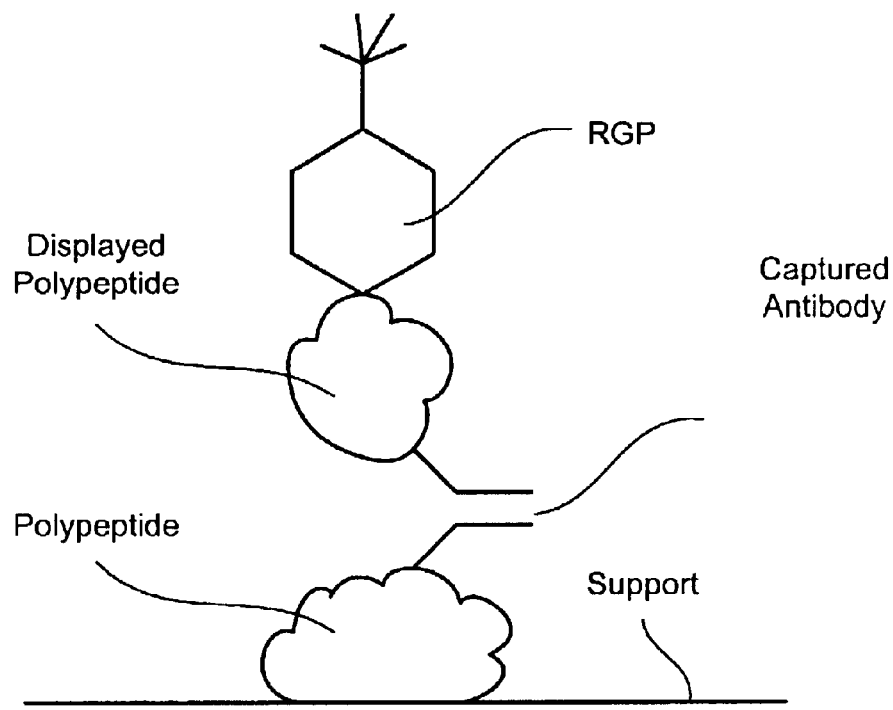
FIGS. 15A–15C illustrate the structures of exemplary arrays as provided herein.

Other analyses involve the in situ identification of many (or all) proteins in a two-dimensional gel. This is accomplished by incubating the gel or a replica blot thereof with the package/antibody library. Unbound and non-specifically bound package/antibody reagents are washed away, thus leaving an array of immobilized proteins complexed with package/antibody reagents (see FIG. 15A). Reagents that remain bound to the gel are picked (eluted) from different spots on the gel, amplified and then sequenced.

In certain gel analyses such as just described, several or many different reagents can be isolated from any given spot on the gel. This is a consequence of the fact that each package/antibody reagent can contain a different segment of the cognate full-length nucleic acid clone, each segment expressing one or a few (or in some longer clones, many) different epitopes. Thus, in certain instances (depending, for example, on the method of cDNA preparation) the entire full-length cDNA sequence can be deduced from the nested sequences of several of the recovered reagents. Such methods then become an additional tool for determining the sequence of a given expressed genome. In those cases where the proteins under analysis derive from organisms with fully sequenced genomes, even a short segment from a single package clone can serve to unambiguously identify the protein(s) in a spot from a 2-D gel.

Even though proteins have the same primary sequence they sometimes can appear at different locations on a gel because of differential processing that results in proteins being differentially modified. For example, proteins of the same sequence that are differentially phosphorylated or glycosylated may become separated from one another on the gel. The antibody/package reagents described herein can be utilized to detect the presence of such differentially modified proteins. More specifically, different spots on a gel that include the same proteins can be identified by determining which spots contain proteins that bind to the same package/antibody reagents.

Such analyses can be conducted without sequencing, thus allowing one to rapidly identify spots that have differentially modified proteins that have the same primary sequence. In general, this can be done by lysing the packages of the reagents that have formed a complex with proteins in the spots to expose the heterologous nucleic acid and then probing the gel with a labeled nucleic acid probe that is complementary to at least a segment of the heterologous nucleic acid under conditions such that the probe can hybridize with a complementary segment.

One approach for conducting such analyses that simplifies the hybridization step is to utilize isothermal tags. Isothermal tags refer to nucleic acid sequences that have the same base composition but which differ in the ordering of the bases. Because they have the same overall base composition, isothermal tags have the same melting temperature. Consequently, one can conduct hybridization and washing steps with multiple probes under a single set of conditions, thereby significantly simplifying the screening process. The isothermal tags are introduced by attaching the tag to the heterologous nucleic acid sequence that encodes the expressed polypeptide prior to incorporating the heterologous sequence into the replicable genetic package.

IV. Arrays of Package/Antibody Reagents and Methods of Use

A. General

The replicable genetic package/antibody reagents described in section III can also be utilized in a variety of array formats. Certain arrays include package/antibody reagents that are immobilized on a support, and thus constitute an array of immobilized antibodies that can capture a target protein for which the antibodies have specific binding affinity (see, e.g., FIG. 15B). With this type of array, the identity of a target protein that is complexed to a reagent on the array can be determined from the sequence of the segment of the heterologous nucleic acid of the reagent that has captured the target protein. As pointed out above, this is because the sequence of the segment encodes for an epitope that is shared by the polypeptide expressed by the reagent and the captured target protein.

Arrays of this type can be utilized in a number of different applications similar to the profiling applications conducted using nucleic acid arrays. Thus, the arrays can be utilized to detect qualitatively or quantitatively the presence of one or more proteins for cells or tissues under a particular set of conditions or stage of development. One can also conduct differential expression studies in which proteins expressed under one set of conditions are compared to proteins expressed under another set of conditions. Because the arrays disclosed herein monitor some or all of the proteins in a cell or tissue instead of mRNA levels as do nucleic acid arrays, the arrays provided herein can yield a more accurate view of the actual components that regulate biological process. Knowledge of the identity and/or amount of each protein enables one to gain a more complete understanding of biological processes.

Figure 15B:
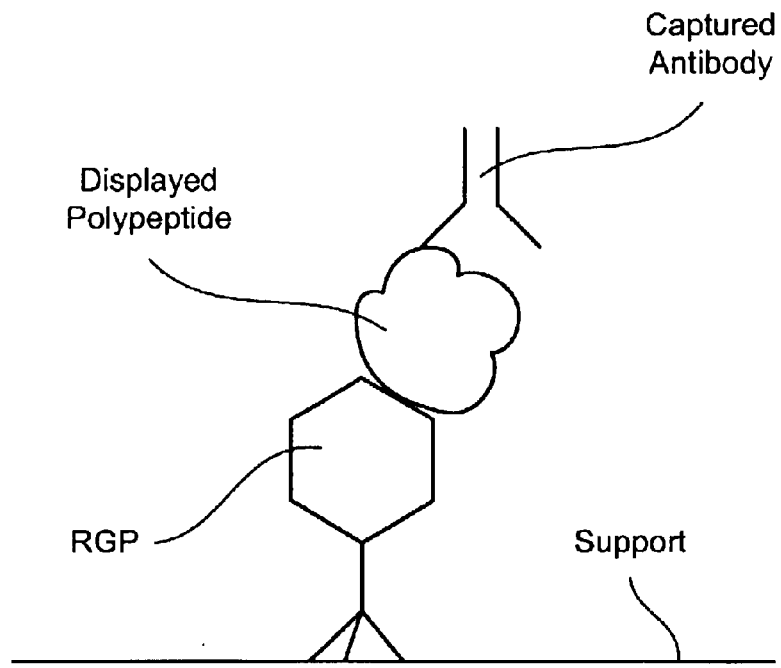
Figure 15C:
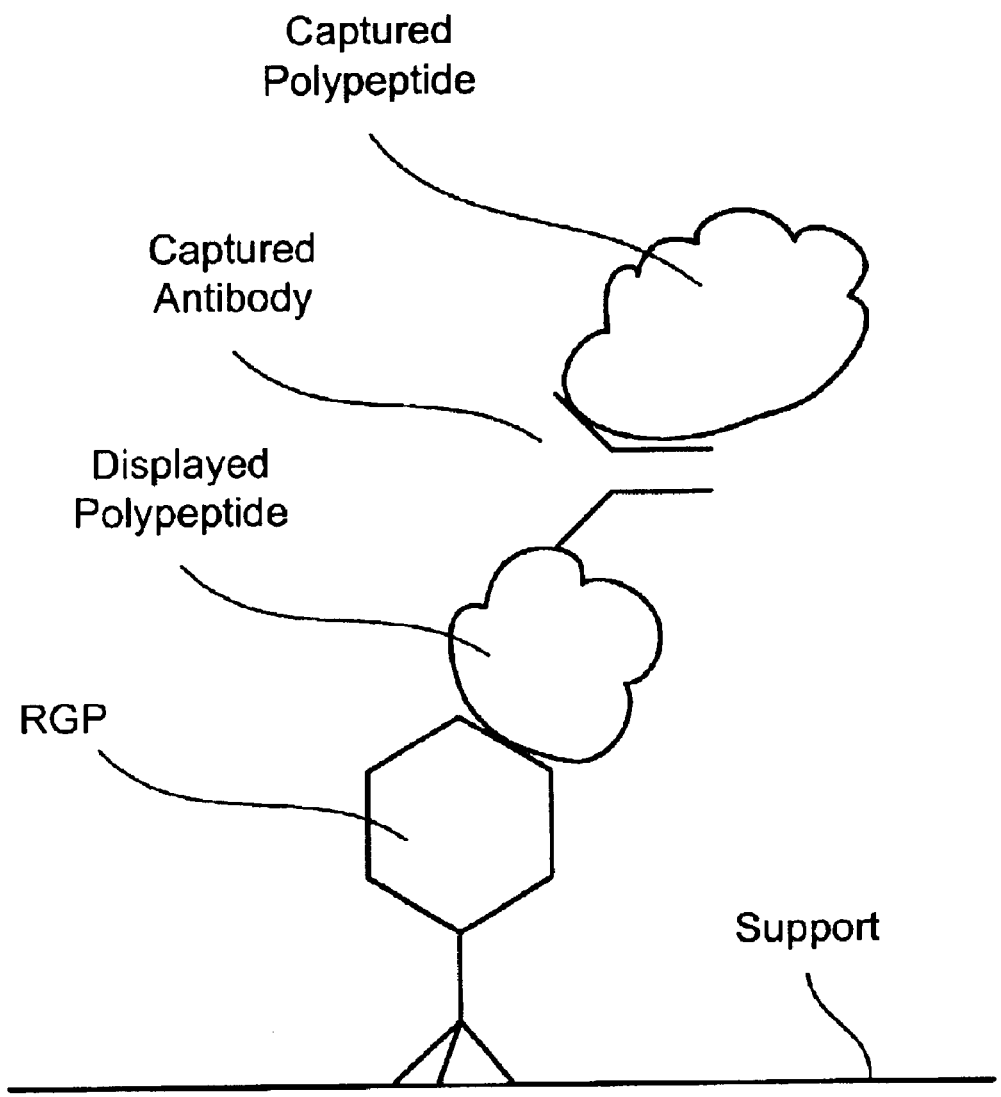

Other arrays that are related to those exemplified in FIG. 15B also include proteins captured by the antibodies (see, e.g., FIG. 15C). Arrays of this type can display functional polypeptides and can be utilized in a variety of studies on protein/protein interactions.

B. Array Preparation/Structure

1. Immobilization of Replicable Genetic Packages

The components of the package/antibody reagents that are immobilized on a support to form the array can be prepared according to the preparation methods described in section III. If not already available, the cDNA display library and the population of capture antibodies are prepared. Certain arrays are then formed by immobilizing members of the cDNA display library onto locations on a substrate. The cDNA display library can be immobilized in a number of ways. One technique is to spot aliquots of package clones in specific locations on the support such that different clones are spatially addressable. The aliquots can be spotted utilizing a variety of available techniques such as using modified ink jet printers, robotic spotters and capillary arrangements. Arrays of a variety of densities can be prepared utilizing such approaches. Certain arrays have densities of at least $10, 10^2, 10^3, 10^4, 10^5, 10^6, 10^7$ or $10^8$ locations/cm$^2$ or any integral number of locations therebetween.

Other methods can be utilized to immobilize reagents when the replicable genetic packages are filamentous and lytic phage. For instance, if fd phage are utilized, an array of polypeptide-displaying phage can be created by growing bacterial micro-colonies expressing display phage (i.e., bacteriophage with the display polypeptide on the surface). If lytic phage (e.g., T7) are used, then a lawn of micro-plaques is grown. The array of colonies/plaques is then replicated onto a support, followed by treatment to achieve stable attachment of the phage to the support surface using standard methods of colony and plaque lifts as described in Sambrook, et al. (1989) Molecular Cloning: A Laboratory Approach, 2nd ed., Cold Spring Harbor Laboratory Press. Such methods using colonies or plaques do not require a uniform array (i.e., deposition of package clones at particular locations), but can be conveniently prepared by simply plating or spreading the phage on a growth medium and permitting the phage to replicate prior to replication and immobilization of the colonies or plaques on the support. Thus, such approaches avoid the need for automated arraying equipment.

These methods of generating either micro-colonies or micro-plaques can be utilized to generate high density protein arrays that otherwise would be difficult to prepare utilizing standard deposition methods. High densities of proteins can be achieved by preparing arrays in this fashion because very small colonies or plaques (e.g., approximately 5 microns or less in size) can be formed. In general densities of at least $10^2$ to at least $10^8$ locations/cm$^2$ are obtained. Thus, utilizing such techniques arrays having at least $10^5, 10^6, 10^7$ or $10^8$ locations/cm$^2$ or any integral number therebetween can be prepared. In some instances, even higher density arrays having $10^9$ or $10^{10}$ locations/cm$^2$ or any integral number therebetween can be prepared.

Regardless of the particular method by which the display library is attached to the support, usually a replica of the resulting array is made and preserved to provide an archival collection of the package clones in which the location of the various clones are maintained. Thus, at this stage one has a high density array of package clones, each expressing a polypeptide (of fragment thereof) from the cells or tissue being studied. This array of displayed proteins can be utilized directly in various applications as described further infra.

2. Complexing Antibodies to Immobilized Packages

Once the array of display packages has been formed, it is contacted with an antibody collection, with antibodies forming complexes at those locations that contain immobilized reagents that display polypeptides to which the antibodies have specific binding affinity. As described in section III.B.3, because the density of the polypeptide displayed on package is designed to be relatively low, multivalent antibodies binding to a displayed protein typically have one or more additional sites that are available to bind with target protein in a sample. Consequently, free antibody recognition sites are displayed at each location of the array. The specificity of the antibodies within the location corresponds to the epitope of the polypeptide displayed by the package immobilized at that location. Hence, at this step of the process, the array is effectively an anti-target protein antibody array, and it can be utilized to evaluate the global protein complement (or some subset thereof) of the cells of interest.

One alternative to the foregoing methods is to generate the package/antibody reagents and then attach these to the support. The reagents can then be deposited using the modified ink jet printers, robotic spotters and capillary arrangements described supra, for example.

3. Array Structure

Hence, utilizing methods such as those just described, a wide variety of arrays in which polypeptides are immobilized at different locations on a substrate can be formed. The arrays can differ in a number of aspects, including for example, the type of polypeptide available for binding, the density of locations (and thus polypeptides) on the array, and the number of different polypeptides immobilized to the array.

For example, certain arrays contain immobilized package/antibody reagents, thus forming an array of displayed antibodies (see FIG. 15B). The antibodies displayed in these arrays can be of a number of different types. Suitable antibodies in such arrays include, but are not limited to, diabodies, tribodies, tetrabodies, IgG antibodies, and can also be the antibody from another package/antibody complex, provided the antibody of the complex is multivalent.

Other related arrays also include immobilized package/antibody reagents, but also include polypeptides that have been captured by the captured antibody of the immobilized package/antibody complexes (see, e.g., FIG. 15C). In such arrays, the protein captured by the antibody can be of a number of different types. The captured protein in certain arrays is a functional protein. In general, functional proteins refer to proteins that retain the activity or a substantial portion of the activity associated with the particular protein. Functional proteins can be obtained and isolated from a cell. These proteins typically include the post-translational modifications associated with the protein as obtained from a cell, are full-length or substantially full length, and properly folded such that the protein is functional.

The density of locations on the substrate can include any of the densities listed above. Typically, polypeptides within a location have are the same (e.g., have the same amino acid sequence) but this is not required. Similarly, at least some, and in other instances many, of the different locations on the support have different polypeptides immobilized therein. However, with some arrays at least some of the locations will have the same polypeptide immobilized therein. As used herein, "different" polypeptides refer to polypeptides that have different amino acid sequences and/or that differ in some other characteristic or property (i.e., proteins with a "differential modification"). The characteristic or property differentiating the polypeptides often is a difference in postranslational modification, such as glycosylation, acetylation or post translational processing resulting from protease activity, for example. Polypeptides referred to as being the same are those having the same amino acid sequence, and can also refer to polypeptides that additionally have the same postranslational modifications. The number of different polypeptides that are immobilized on the array can be less than 10, but more typically is at least 10, 20, 30, 40, 50, 60, 70, 80, 90 or 100 different polypeptides or any integral number therebetween. Certain arrays have even more immobilized polypeptides, such as at least $10^2$, $10^3$, $10^4$ or $10^5$ different polypeptides or any integral number therebetween.

The locations on the substrate to which members are immobilized can vary significantly in size and can be of different shapes. The substrate can be essentially any material to which the cDNA library can be attached and which is physically and chemically compatible with wash solutions that are used to remove unbound or non-specifically bound proteins from the array. Suitable supports include, but are not limited to, polymeric materials such as plastics, resins, cellulose, nylon, PVDF and polysaccharides, as well as silica or silica-based materials and inorganic glasses. The substrates can be in a variety of forms such as sheets, membranes, tubes and beads, for example.

C. Contacting Array with Protein Sample

When a protein-containing sample is applied to the array, proteins become complexed or captured at those sites that contain antibodies that recognize the various epitopes on the proteins. These sites are, in turn, the sites at which the cDNAs encoding the captured proteins also reside. Depending upon the distribution of the package/antibody complexes on the array, in some instances a particular protein can be captured at a number of different sites on the array. This feature, however, can be controlled and can be used to advantage as described infra. After proteins in solution have had sufficient time to form complexes with the immobilized package/antibody reagents, the array is optionally washed with a rinse solution to remove unbound and/or non-specifically bound protein.

D. Detection and Identification

A variety of different options for detecting which locations of the array have captured protein from the sample are available and-generally parallel those methods listed in section III C. In brief, one option is to label the proteins within the sample prior to applying the sample to the array. Once the labeled proteins have had an opportunity to form complexes with the immobilized reagents on the array, unbound or non-specifically bound labeled proteins can optionally be washed away during a washing step. Target proteins that remain bound to the array can subsequently be detected.

Alternatively, detection reagents such as those described in section III.C.3. can be washed over the array. Those detection reagents that specifically bind to target proteins captured on the array bind to the array to form a complex that includes: (i) immobilized reagent, (ii) captured target protein, and (iii) detection reagent. An optional washing step can be performed to remove unbound or non-specifically bound detection reagent prior to detecting complexes. Regardless of the detection reagent utilized, methods can be conducted in a manner such that the extent of binding of the labeled detection reagent to each location on the array is a reflection of the relative amount of protein bound to any particular spot. Thus, certain methods can be utilized in a quantitative fashion to obtain quantitative information on different proteins within a sample. The goal with other methods is to obtain qualitative information. For instance, one can use protein arrays of the type described herein to obtain a "fingerprint" of the protein content of a cell or tissue under particular growth conditions, at a particular stage of development or differentiation, or after exposure to a particular environmental stimulus.

In certain comparative methods, one is primarily interested in the protein expression pattern observed on the array and it is not necessary to determine the identity of each target protein that is bound to the array. For instance, the expression pattern can be used to track changes in cells at different periods (e.g., different developmental stages) or under different conditions. With the arrays provided herein, such generalized information can be obtained for some, many, or all of the proteins within a cell or tissue.

However, considerably more information can be obtained, information that is not readily obtainable using conventional antibody arrays. In particular, the methods disclosed herein can be used to rapidly identify the protein captured at every (or any) location on the array, even if the protein is completely novel. This capability is possible with the package/antibody arrays provided herein because each site of the array physically contains the cDNA sequence of the protein under evaluation at that site (i.e., of the protein captured at that site). To interrogate the actual sequence and thus identity of any particular captured protein, it is only necessary to establish the sequence of a segment of the nucleic acid of the package at the location at which the protein is captured. The sequence of the nucleic acid segment includes the sequence of a shared epitope on the captured polypeptide.

The sequence of the nucleic acid segment that corresponds to a shared epitope of a captured protein can be determined in various ways. One approach utilizes the replica of the array that preserves the location of the various package/antibody reagents on the array. In particular, a package from the archival replica is removed from the location on the replica that corresponds to the location on the array at which a target protein is bound. The nucleic acid from the removed package is extracted and sequenced to reveal the primary nucleic acid sequence; this sequence of course can be utilized to determine a primary amino acid sequence that includes the sequence of an epitope that is shared by the polypeptide displayed by the reagent and the captured protein. Thus, for example, if a set of sites on the array are seen to differ in their protein content, the DNA from packages from the replica (master archive) corresponding to those sites can be sequenced to obtain the primary amino acid sequence of at least a portion of the protein(s) bound at those sites.

The identification step can be accomplished without the use of an archival replica by using detection reagents (see section III.3.C.). Since the polypeptide displayed by the package of the display reagent that binds to the target protein is the same as the captured protein and the polypeptide displayed by the immobilized package/antibody complex, the segment of the nucleic acid that encodes the polypeptide of the detection reagent and on the immobilized reagent are the same. Thus, one can determine the sequence of the segment of an immobilized reagent that has captured a protein from the sequence of the nucleic acid of the detection reagent complexed to the captured protein.

The detection reagent bound to any site of interest can be removed using microdissection techniques and the segment of the heterologous nucleic acid of the detection reagent sequenced to determine the corresponding sequence in the immobilized reagent that captured the protein. Suitable microdissection instruments include a capture microdissection instrument. In some instances, these instruments are lasers such as those marketed by Arcturus Engineering of Mountain View, Calif. Once a package is removed, the nucleic acid is removed, typically amplified using established methods and then sequenced. Such techniques can be used for locations on the array that are as small as 10 microns in diameter.

E. Optional Normalization Techniques

As indicated above, some sites in the array may include package/antibody reagents that display the same polypeptide. Hence, such sites will capture the same specific antibodies, and thus capture the same proteins from the applied sample. This is especially true of proteins that are highly transcribed within the cells or tissues being studied. Normalization procedures known in the art can be utilized to address this issue when preparing the cDNA libraries for this application (see, e.g., Sambrook, et al. (1989) Molecular Cloning: A Laboratory Manual, 2nd Ed., Cold Spring Harbor Laboratory Press, Cold Spring Laboratory, N.Y.).

However, even with normalization, in some instances methods for arraying the members of the cDNA display library result in many of the expressed polypeptides being positioned at multiple sites. Such arrays, however, can be used to advantage. For example, when several sites express a similar segment of a particular cDNA (i.e., the displayed polypeptide fragment borne by packages contains the same epitopes and thus captures the same set of antibodies), the intensity of the signal from those sites will rise and fall in concert with changes in the level of protein binding to those sites. Thus, such sites can serve as internal controls in verifying the changes observed at other sites.

The presence on an array of multiple sites having reagents that display related proteins can also be used to good effect in distinguishing between modified and unmodified proteins. For example, reagents displaying polypeptides that contain different segments of the same protein (and therefore contain different sets of epitopes) may be present at several different locations on the array. In some instances, the polypeptide expressed by the immobilized reagent contains only a single epitope that can be modified by phosphorylation or glycosylation, for example. Such modification may allow or prevent the binding of the cognate antibodies, thereby allowing differentially modified proteins at the different locations to be distinguished. This feature can provide important insight into regulatory mechanisms, for example.

V. Target Protein Identification

A. Detection Options

As set forth above, depending on the nature of the detection technique utilized, labeled target protein or various labeled detection reagents (e.g., labeled antibodies or labeled packages) can be used to detect the formation of a complex between a target protein and package/antibody reagent. A variety of different labels can be utilized in these detection schemes. The proteins, antibodies or packages can be labeled with any of a variety of different types of labels, provided the label does not interfere with the formation of a complex between a package/antibody reagent and a target protein and can generates a detectable signal once such a complex is formed. Suitable labels include, but are not limited to, radiolabels, chromophores, fluorophores, electron dense agents, NMR spin labels, a chemical tag suitable for detection in a mass spectrometer, agents detectable by infrared spectroscopy or NMR spectroscopy, and enzyme substrates or cofactors for example. Radiolabels, particularly for spatially resolved proteins, can be detected using phosphor imagers and photochemical techniques.

Certain methods utilize fluorophores since various commercial detectors for detecting fluorescence from labeled proteins are available. A variety of fluorescent molecules can be used as labels including, for example, fluorescein and fluorescein derivatives, rhodamine and rhodamine derivatives, naphythylamine and naphthylamine derivatives, benzamidizoles, ethidiums, propidiums, anthracyclines, mithramycins, acridines, actinomycins, merocyanines, coumarins, pyrenes, chrysenes, stilbenes, anthracenes, naphthalenes, salicyclic acids, benz-2-oxa-1-diazoles (also called benzofurazans), fluorescamines and Bodipy dyes.

B. Sequence Determination

Once a complex has been detected, often the methods next involve determining the sequence of the nucleic acid of the package of a package/antibody reagent to which a target protein is bound. By translating the nucleic acid sequence, one can determine an amino acid sequence that includes the epitope of the target protein. In view of the detection options described supra for both array and non-array formats, it should be understood that the sequence of a segment of the heterologous nucleic acid of a reagent that complexes with target protein can be determined in a number of different ways. One option is simply to isolate the reagent, extract the nucleic acid segment and sequence it. The sequence can also be determined by extracting the segment and utilizing nucleic acid probes to detect the presence of complementary segments in nucleic acids that have been extracted from reagents that have captured target protein. Alternatively, the sequence can be deduced from the sequence of the heterologous nucleic acid of a detection reagent that complexes with the target protein captured by a reagent.

Generally, the nucleic acid is amplified before sequencing is commenced. Amplification is typically conducted using the polymerase chain reaction (PCR) according to known procedures. See generally, PCR Technology: Principles and Applications for DNA Amplification (H. A. Erlich, Ed.) Freeman Press, NY, N.Y. (1992); PCR Protocols: A Guide to Methods and Applications (Innis, et al., Eds.) Academic Press, San Diego, Calif. (1990); Mattila et al., Nucleic Acids Res. 19: 4967 (1991); Eckert et al., PCR Methods and Applications 1: 17 (1991); PCR (McPherson et al. Ed.), IRL Press, Oxford; and U.S. Pat. Nos. 4,683,202 and 4,683,195. Other suitable amplification methods include the ligase chain reaction (LCR) (see, e.g., Wu and Wallace, Genomics 4:560 (1989) and Landegren et al., Science 241:1077 (1988); transcription amplification (see, e.g., Kwoh et al., Proc. Natl. Acad. Sci. USA 86:1173 (1989)); self-sustained sequence replication (see, e.g., Guatelli et al., Proc. Natl. Acad. Sci. USA, 87:1874 (1990)); and nucleic acid based sequence amplification (NABSA) (see, e.g., Sooknanan, R. and Malek, L., Bio Technology 13: 563–65 (1995)).

Sequencing of the amplified sequence can be conducted with any of a number of different commercially-available nucleic acid sequencers.

VI. Samples

The methods disclosed herein can be used with a wide range of protein samples types, provided the protein sample can be brought into contact with the package/antibody reagents (or arrays containing such reagents) such that complexes between target proteins in the sample and the package/antibody reagents can form. The samples can contain a relatively small number of proteins or can contain a large number of proteins, such as all the proteins expressed within a cell or tissue sample, for example. Samples can also contain a subset of the proteins of a cell or tissue, such as the proteins within a particular cellular organelle or subcellular compartment.

Samples can be obtained from any organism or can be mixtures of synthetically prepared proteins or combinations thereof. Thus, suitable samples can be obtained, for example, from microorganisms (e.g., viruses, bacteria and fungi), animals (e.g., cows, pigs, horses, sheep, dogs and cats), hominoids (e.g., humans, chimpanzees, and monkeys) and plants. The term "subject" as used to define the source of a sample includes all of the foregoing sources, for example. The term "patient" refers to both human and veterinary subjects. The samples can come from tissues or tissue homogenates or fluids of an organism and cells or cell cultures. Thus, for example, samples can be obtained from whole blood, serum, semen, saliva, tears, urine, fecal material, sweat, buccal, skin, spinal fluid, tissue biopsy or necropsy and hair. Samples can also be derived from ex vivo cell cultures, including the growth medium, recombinant cells and cell components. In comparative studies to identify potential drug or drug targets (see infra), one sample can be obtained from diseased cells and another sample from non-diseased cells, for example.

If the sample contains cellular debris or other non-protein material that might interfere with the analysis, such materials can be removed using any of a variety of known separation techniques including, for example, forcibly exuding the sample through sieve material, filtration and centrifugation.

VII. Exemplary Utilities

A. General

The methods, reagents and arrays described herein can be utilized in a variety of proteomic applications. In general, the methods and compositions can be utilized to detect, characterize and/or identify many proteins (e.g., tens, hundreds or thousands of proteins in some instances). With such capabilities, the methods and compositions have utility in a wide range of applications including, but not limited to: (i) various analytical applications (e.g., monitoring certain protein levels as a function of external stimuli, or detecting specific proteins in complex compositions for identification purposes); (ii) clinical applications (e.g., detecting and/or monitoring compositions of normal and diseased cells and tissues, diagnosing or monitoring disease, testing drug candidates for therapeutic efficacy, and toxicity testing); and (iii) molecular biology and genetic research (e.g., characterizing or monitoring molecular expression levels of gene products and determining the effects of the addition, mutation, deletion or truncation of a particular gene).

More particularly, the methods and compositions can be utilized to identify the primary sequence of any, most, or all of the proteins in tissues, cells or subcellular compartments (e.g., such as at least 20%, 30%, 40%, 50%, 60%, 70%, 80% or 90% of the proteins in the tissue, cell or compartment). The methods and compositions can also be used for the same purpose in the analysis of complex protein mixtures that have been separated in one- or two-dimensional separation formats (e.g., one- or two-dimensional electrophoretic gels), or similar analyses conducted in array-based formats (including arrays that include unknown proteins and arrays in which known proteins are immobilized at unknown locations).

A. Screening

One use of the methods and compositions is to examine either qualitatively or quantitatively the proteins that are expressed in a particular tissue or cell. However, one can also screen a large number of samples to detect the presence of individual proteins or small subsets of proteins. The specific reagents or panels of reagents described herein make such analyses facile. Screens of this type find utility in a variety of medical applications as described further below. Such screening methods can also be utilized in various identification applications, such as identifying a particular cell type, species or even an individual of a species.

B. Reagents and Arrays for Specific Analyses

The reagents provided can be tailored to any of a number of particular applications. For example, individual package/antibody reagents that have specific binding affinity to any protein of interest can be created, provided at least some portion of the primary sequence of the protein is known, using the methods and compositions described herein. This is done by: (i) cloning the cDNA sequence of the target protein into a replicable genetic package to obtain a package displaying the protein of interest (or cloning a small population of fragments to obtain a small library of display packages); (ii) exposing the display package to an antibody collection to capture the specifically reactive antibodies; and (iii) recovering the resulting package/antibody reagent. The resulting reagent can be used in the detection of the protein of interest in a protein sample. Of course a collection of such reagents can be prepared to detect a particular group of proteins of interest.

Domain-specific or cell fraction-specific populations of antibodies can be readily produced in a related manner. Such methods generally involve: (i) creating a library of package/antibody reagent libraries that represent the total protein from a cell as described herein; (ii) enriching for those package/antibody reagents that are specific to the cell location or fraction of interest (e.g., by contacting the reagents to the apical domain of an epithelial cell to enrich for reagents that specifically bind to proteins in this particular location); and (iii) recovering and amplifying such packages for use as an immunogen in one of the antibody preparation formats described in section III.B.2. The resulting antibodies can be utilized in a variety of applications to detect proteins from the particular domain or cell fraction of interest.

Arrays of full-length functional proteins such as discussed above can be constructed by: (i) preparing a cDNA display library as described in section III.B.1.; (ii) arraying the members of the cDNA display library onto a support; (iii) exposing the array to an antibody preparation prepared using a corresponding display library as the immunogen as disclosed in section III.B.2. and washing away the unbound antibodies; and (iv) contacting the array with a protein preparation from a cell or tissue of interest, thereby capturing specific proteins in specific locations on the array (see FIG. 15C). Thus, arrays prepared according to steps (i)–(iii) can be utilized to capture functional proteins which can be assayed in situ for their activity (e.g., enzyme activity) and to detect other proteins in a mixture that interact with the functional proteins displayed in the array.

Hence, a variety of protein/protein interactions can be probed using reagents having the general structure: package/displayed protein/captured antibody/captured functional protein. By using labeled target proteins, for example, reagents of this type can be used to detect target proteins in a sample that interact with the functional protein. The sequence of the package that is complexed with a target protein identifies the functional protein that interacts with the target protein. The ability to conduct screens with functional proteins as compared to conventional phage display libraries means that one can conduct assays with full length proteins that have been modified as typically occurs within a cell and that are properly folded. The polypeptides in conventional polypeptide display libraries, in contrast, are often fragments, have not been modified and may not be properly folded.

C. Comparative Analyses

Diverse comparative studies can be performed with the methods and compositions provided herein. By comparing qualitatively and/or quantitatively the complement of proteins (or some subset thereof) expressed in cells or tissues from multiple different samples, one can identify a particular protein or group of proteins that are differentially expressed between the samples. A wide variety of such comparisons can be made. For example, one can conduct comparisons of protein expression in cells or tissues exposed to different conditions or at different stages of development or differentiation, for example. A protein whose expression level varies between the different samples can be considered a "marker" or a "fingerprint" protein. Thus, depending upon the nature of the comparison being conducted, one can identify individual markers or fingerprint proteins that correlate with a particular cellular state, stage of development or stage of differentiation, for example. As described more fully infra, marker or fingerprint proteins can be utilized in the development of a wide variety of different screening and diagnostic methods.

Expression levels for combinations of differentially expressed proteins can be used to develop a "fingerprint" or an "expression profile" that is characteristic of a particular cellular state, stage of development, stage of differentiation, or cell or tissue type, for example. Expression profiles or protein fingerprints contain a plurality of differentially expressed proteins, usually at least 2, 3, 4, 5, 6, 7, 8, or 9 proteins. Other profiles or finger prints include considerably more differentially expressed proteins such as 10, 20, 30, 40, or 50 or more proteins, or any integral number of proteins therebetween. Still other profiles can include several hundred proteins. Certain profiles include all of the proteins know to be correlated with a particular cellular state, stage of development or type of cell, for example. In some instances, the term "fingerprint" can be used in a general sense to refer to the particular pattern of expression observed on an array.

One example of a comparative analysis is an analysis in which one identifies a subset of proteins that are expressed in common by different cells or tissues. One approach for doing this involves preparing a library of package/antibody reagents from tissue A (see section III) and then using this library to probe a two-dimensional gel that contains separated proteins from tissue B (see FIG. 15A). Another option is to prepare a cDNA display library from nucleic acids isolated from tissue A. This cDNA library is then used to capture antibodies generated by immunizing an animal with proteins from tissue B to form a library of package/antibody reagents. The resulting reagent library can then be utilized to probe tissue A, B or any other tissue C.

As a more specific illustration of the utility of such comparative studies, the following examples demonstrate how the methods and compositions can be utilized to identify potential drug targets and/or candidates and in toxicological investigations. For example, the methods can be utilized to identify proteins that are differentially expressed in diseased cells as compared to normal cells. Such differentially expressed proteins can serve as targets for drugs or serve as a potential therapeutics. In a related fashion, the methods can be used in toxicology studies to identify proteins that are differentially expressed in response to particular toxicants. Such differentially expressed proteins can serve as potential targets or as potential antidotes for particular toxicants.

The comparative studies necessary to identify the differentially expressed proteins often are conducted on an array because of the ease of detection and drawing comparisons between the expression pattern observed on the different arrays. The comparisons can be conducted in various ways. One option is to separately apply different samples to different arrays such that the comparative analyses are conducted in parallel. Another option is to differentially label the different protein samples and then apply the samples to a single array. Proteins from one sample can be differentiated from those from another sample on the basis of the different labels. The ratio of the labels can be utilized to determine the ratio of the concentrations of the proteins from the samples.

D. Diagnostic Applications

The results of comparative studies are transferable to a variety of diagnostic applications. For example, "marker" or "fingerprint" proteins identified during comparative studies as being characteristic of a particular disease can be used to diagnosis individuals to determine if they have the disease correlated with the marker. These markers can also be used in medical screening tests.

Furthermore, as described supra, once marker or fingerprint proteins have been identified, one can rapidly generate package/antibody and/or antibody reagents that specifically recognize such proteins. These reagents can be used in the preparation of diagnostic kits and devices. For example, through comparative analyses such as those just described, one can identify diagnostic markers (e.g., cell surface antigens or serum proteins) for immunodiagnostic assays. Purified marker or display packages displaying the identified epitope can then be utilized to generate antibodies having specific binding affinity to the protein marker. Such antibodies can be used in immunological staining techniques to localize the protein in diseased cells or to rapidly screen patients for the presence of the protein.

E. Creating Databases

The methods described herein can also be used to generate information on proteins that is used to populate a database. An exemplary database might include, for example, the identity and quantity of protein present in cells or tissues under a particular set of conditions. Other entries in the database could include similar information for cells or tissues under a variety of other conditions. Information in the databases can be further cross referenced with a variety of information regarding the source and identity of the sample, method of sample preparation and the like.

F. Establishing Structure Activity Relationships and Metabolic Engineering

The methods provided herein have further utility in conducting structure activity studies. For instance, the methods can be used to determine the effect that certain chemical agents or combination of agents have on protein expression patterns. Alterations to the agent or combination can then be made and protein expression reassessed to determine what effect if any the alteration has on protein expression. Such studies can be useful, for example, in making derivatives of a lead compound identified during initial drug screening trials.

Metabolic engineering studies can also be performed utilizing the present methods and compositions. In such studies, for example, a gene can be modified using established genetic engineering techniques or the promoter for the gene is modified to increase or decrease the expression level of the gene. The methods described herein can then be used to determine what effect, if any, the genetically engineered changes have on proteins within a cell harboring the changes other than on the protein encoded by the genetically engineered gene.

G. Endocytosis and Transcytosis Assays

Active transport of compounds into or through cells can occur by varying mechanisms including endocytosis and transcytosis. Endocytosis is often initiated by the binding of a ligand to a cell surface receptor and results in the uptake of extracellular materials, including fluid, dissolved solutes, and particulate matter. All eukaryotic cells undergo a continuous process of vesicle formation at the cytoplasmic side of the plasma membrane. Following uptake, vesicles are directed to any of a number of cellular locations. The pathway and ultimate destination are directed by a variety of signal motifs present in the cytoplasmic, transmembrane and extracellular domains of the proteins located on the vesicles, and, in some cases, by the non-protein membrane components of the vesicles.

Transcytosis refers to a process in which the vesicles are transported from one side of a polarized cell (e.g., an epithelial cell or an endothelial cell) to the other side. The vesicle docks and fuses with the plasma membrane and the contents are emptied to the extracellular compartment. Polarized cells in which such transport occurs are present in many tissues. In all epithelial layers, the layers of cells separating the body from the outside world, the cells are polarized. Epithelial cell layers are characterized by the presence of tight junctions that form an effective seal between all the cells of the layer. It is this seal that divides the cells into an apical (outside) and a basal (inside) surface. The areas between the cells on the inside side are lateral; hence, the entire inside surface of the epithelial cell is known as the "baso-lateral" surface.

The reagents provided herein can be utilized to conduct screens of proteins to identify receptors that are involved in endocytosis and transcytosis pathways. The preparation of the reagents for use in such assays closely parallel the methods described supra. In general, a cDNA display library is prepared as set forth above from cells involved in endocytosis (essentially any cell) or transcytosis (polarized cells such as epithelial or endothelial cells). An antibody collection against all surface proteins or apical surface proteins is prepared using such proteins as immunogens. The cDNA library is subsequently incubated with the antibody collection to form a population of replicable genetic package/ antibody reagents; unbound antibodies are washed away.

These reagents can then be utilized to conduct a variety of in vitro or in vivo assays to identify reagents bearing an antibody capable of binding to a cell surface receptor and causing transport of the reagent into or through a cell. By determining the sequence of the heterologous sequence of such reagents, one can determine the identity of the receptor involved in transport.

For example, certain in vitro assays involve growing polarized cells (e.g., CaCo cells) as a monolayer on a semipermeable membrane that contains pores sufficiently large to allow the passage of reagents therethrough and which divides an apical compartment from a basal compartment. The replicable genetic package/antibody reagents are contacted with the apical side of the cells in the apical compartment. The reagents are allowed to remain in contact for a period of time sufficient to allow transport through the cells. Reagents that have been transported into the basal compartment are subsequently collected. Such reagents display antibodies capable of interacting with a cell surface receptor that causes transcytosis. By determining the sequence of the heterologous sequence of such reagents, one can determine the identity of the receptor involved in the transport.

A number of other in vitro and in vivo methods for assaying for endocytosis and transcytosis that can be utilized with the reagents provided herein are described in PCT publication WO 01/23619.

The following examples are provided to illustrate certain aspects of the methods, antibody/package reagents and arrays described herein and are not to be construed so as to limit the scope of the invention.

EXAMPLE 1

Capture and Display of Polyclonal Antibodies Against the hTNF Receptor on T7 Phage Displaying hTNF Receptor cDNA Fragments I. General A cDNA fragment library of the human type I TNF receptor (hTNFR-1) extracellular domain was cloned into the mid-copy expression T7 display vector T7Select10-3b (Novagen). This expression systems produces T7 phage particles displaying, on average approximately 5–15 copies/ phage of the protein encoded by the cloned cDNA sequence fused to the T7 capsid protein (gene 10). A goat polyclonal antibody against rhTNFR-1 was obtained from R&D Systems, as was a preparation of soluble rhTNFR-1 extracellular domain protein.

An anti-rhTNFR-1 phage-displayed antibody reagent was created by mixing a T7-displayed rhTNFR-1 cDNA epitope fragment with the polyclonal antibody for use in a series of feasibility experiments demonstrating: (a) free anti-rhTNFR-1 binding sites are carried by the phage, (b) the binding sites are available for binding to proteins external to the phage, (c) phage displaying the antibodies can be captured on an immobilized form of the target protein and detected with several phage-specific and target specific reagents, (d) the extent to which the rhTNFR-antibody displayed phage react with other proteins in a complex cellular preparation of proteins, and (e) the ability to detect the specific target protein in a mixture of non-target proteins.

II. Preparation of the T7 hTNFR cDNA Fragment Library

A cDNA encoding the extracellular domain of the human type I TNF receptor was cloned from human liver cDNA (obtained from Clontech) by PCR using gene specific primers. The TNFR cDNA was amplified and then digested with DNaseI in the presence of $MnCl_2$ to produce random double-stranded breaks in the DNA. Fragments of 100 to 300 base pairs in length were gel purified and treated with Klenow fragment of DNA polymerase I to create blunt ends. The cDNA fragments were then ligated to prepared vector arms of the T7Select10-3b display vector (Novagen) to obtain a library of inserts, approximately $⅙^{th}$ of which are in the correct orientation and same translational reading frame as the 10B capsid protein. The resulting DNA was incubated with a T7 in vitro packaging extract, and the phage products were amplified by infecting a culture of BLT5615 host cells. The culture was incubated with shaking at 37° C. for 1–3 hours until lysis was observed, followed by centrifugation at 8,000×g for 10 minutes to clarify the lysate of residual bacterial cells and debris.

T7 phage particles were further purified from the cleared supernatant by precipitation with polyethylene glycol (PEG 8000) and banding in a CsCl step gradient. Briefly, phage were precipitated from the supernatant by adding PEG 8000 to a final concentration of 10% (w/v), incubating on ice for 1 hour, followed by centrifugation at 8,000×g for 15 minutes. Phage were extracted from the PEG pellet in 1M NaCl, 10 mM Tris-HCl, pH 8.0, 1 mM EDTA, and the concentrated phage solution was layered atop four steps of different density CsCl solutions in a clear ultracentrifuge tube. The four CsCl layers were made by mixing a stock solution of 62.5% CsCl in water with TE buffer (10 mM Tris-HCl, pH 8.0, 1 mM EDTA) in the following ratios: 1:2, 1:1, 2:1, 1:0 CsCl:TE. Successively denser solutions were underlayed in the tube and the concentrated phage solution was layered on top of the CsCl steps. The tubes were centrifuged at room temperature for 60 minutes at 35,000 rpm in a Beckman SW41 rotor. Following centrifugation, the turbid band of phage particles above the 2:1 layer was removed by piercing the side of the tube with a syringe needle. Recovered phage particles were then dialyzed in PBS and stored at 4° C. or at −80° C. following the addition of 8% glycerol.

III. Screening T7 hTNFR cDNA Fragment Library Against the Goat Polyclonal anti-rhTNFR Antibody To isolate T7 phage clones displaying hTNFR epitope fragments reactive with the goat polyclonal antibody against hTNFR (BAF225), the fragment library was first selected on immobilized antibody. Briefly, six wells of a 96-well microtiter plate were coated with 5 ug NeutrAvidin biotin binding protein and then blocked with PBS/1% BSA. 1 ug of biotinylated polyclonal goat anti-hTNFR antibody was added to each well and incubated at 4° C. for 1 h, followed by washing with PBS. An aliquot of the T7 hTNFR cDNA fragment library was added to each antibody coated well (approximately $10^9$ TU/well) and incubated at 4° C. for 1 h. The wells were washed extensively with PBS to remove unbound phage, and phage bound to the antibody were recovered by adding PBS/1% SDS to each well. The eluates were then combined and titered on a lawn of BLT5615 cells.

Goat anti-hTNFR reactive phage clones were isolated from the recovered phage population by performing plaque lift analysis as follows. Nitrocellulose membranes were placed on plaque-containing LB/Amp plates for approximately 1 min. The filters were removed and blocked for 1 h at room temperature with PBS/1% BSA, washed several times with PBS, and incubated for 1 h at 4° C. with the biotinylated goat anti-hTNFR antibody diluted to 1 ug/ml in PBS/0.05% Tween 20/0.1% BSA (PBST/0.1% BSA). Filters were then washed with PBS and incubated with horseradish peroxidase-conjugated streptavidin (1 ug/ml in PBST/0.1% BSA) for 1 h at 4° C. Phage plaques stained with the biotinylated antibody and HRP-streptavidin were detected using the colorometric horseradish peroxidase substrate 3,3' 5,5'-tetramethylbenzidine (TMB). Six positive plaques were picked and amplified by infecting cultures of BLT5615 cells; bacterial debris was removed from the lysates by centrifugation and the phage containing supernatants were further characterized in a phage ELISA.

Figure 2:
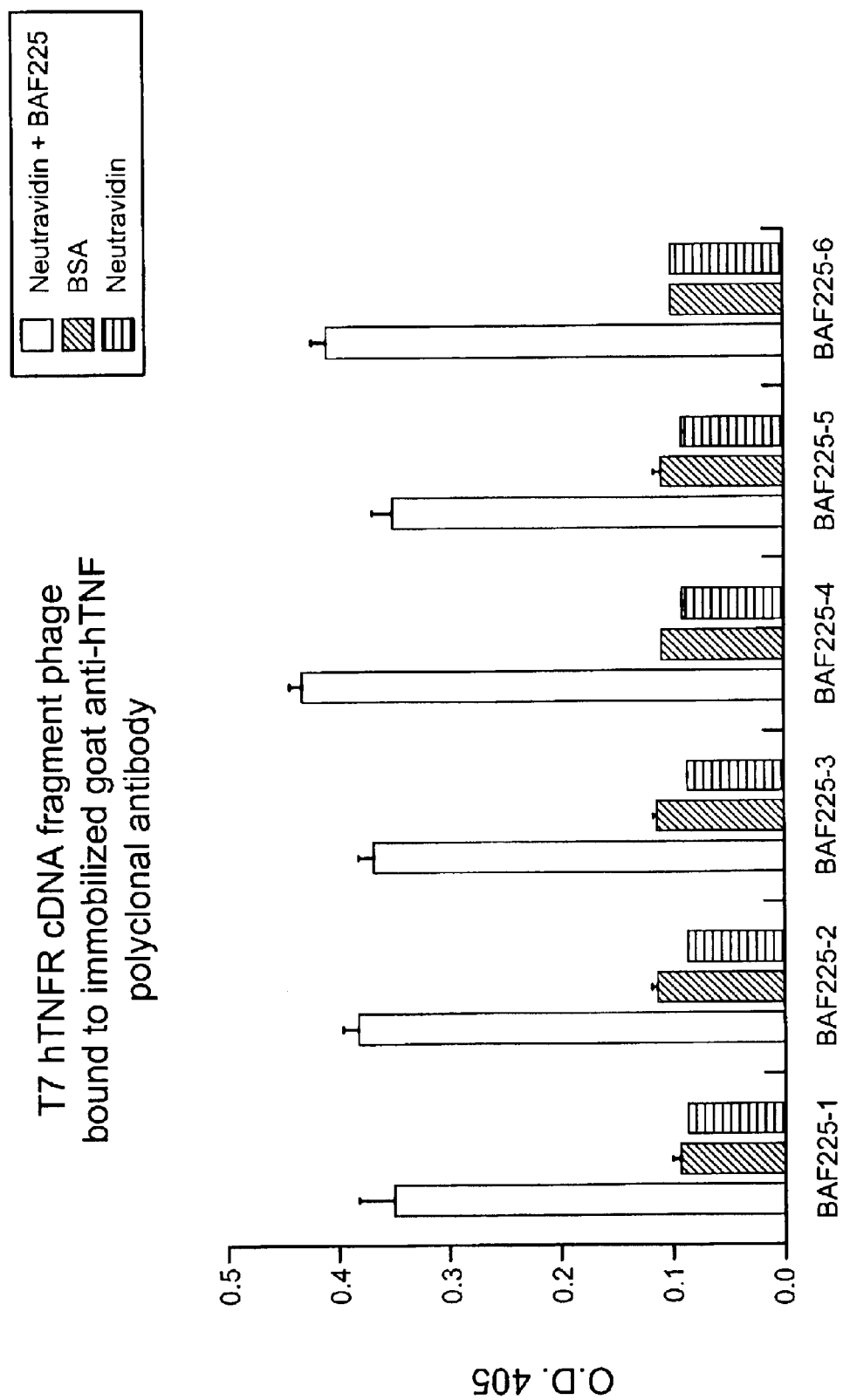
FIG. 2 shows the results of an ELISA of T7 phage displaying hTNFR cDNA fragments captured by immobilized goat anti-hTNFR polyclonal antibody.

For each clone, duplicate wells of a 96-well plate were coated with NeutrAvidin and BAF225 as described above, as well as negative control wells that contained only NeutrAvidin or were blocked with PBS/1% BSA. 50 ul of phage supernatant was added to each well and incubated for 1 h at 4° C. The wells were washed with PBS and bound phage were detected by adding 50 ul of rabbit anti-T7 phage antisera diluted 1:5000 in PBS/0.1% BSA. The anti-phage antibody was detected using a horseradish peroxidase conjugated goat anti-rabbit IgG antibody, followed by addition of ABTS development buffer. The amount of horseradish peroxidase activity in each well was then measured by reading the absorbance at 405 nm with a microtiter plate reader. Phage displaying epitopes reactive with BAF225 were specifically captured on the antibody coated wells (FIG. 2). Sequencing the TNFR cDNA fragments displayed by the positive clones revealed that multiple epitopes in the extracellular domain of TNFR are recognized by the polyclonal antibodies (FIG. 3).

IV. Capture of hTNFR Epitope T7 Phage on Immobilized rhTNFR with a Polyclonal Anti-TNFR Antibody 1 ug of an anti-hTNFR monoclonal antibody (MAb 625) was added to wells of a microtiter plate and incubated for 1 h at 37° C. The wells were washed several times with PBS and blocked by adding 300 ul of PBS containing 1% BSA. The plate was washed and 0.1 ng of soluble rhTNFR-1 diluted in PBS/0.1% BSA was added to each well and incubated for 1 h at 4° C. Following a wash with PBS either 100, 10, or 1 ng of the polyclonal goat anti-hTNFR antibody (AF225) was added to the wells and incubated for 1 h at 4° C. The plate was again washed with PBS and $10^9$ pfu of BAF225-3 phage which display an epitope that binds to the goat polyclonal anti-hTNFR antibody were added to the wells and incubated for 1 h at 4° C. Control wild type T710-3b phage that do not display an anti-TNFR epitope were added to other wells to serve as a negative control. The plate was washed several times with PBS and bound phage were detected by adding a polyclonal anti-T7 rabbit antisera followed by an anti-rabbit IgG HRP conjugate to each well. Bound antibody was detected by the addition of ABTS substrate solution and the absorbance was measured using a microtiter plate reader.

Figure 4:
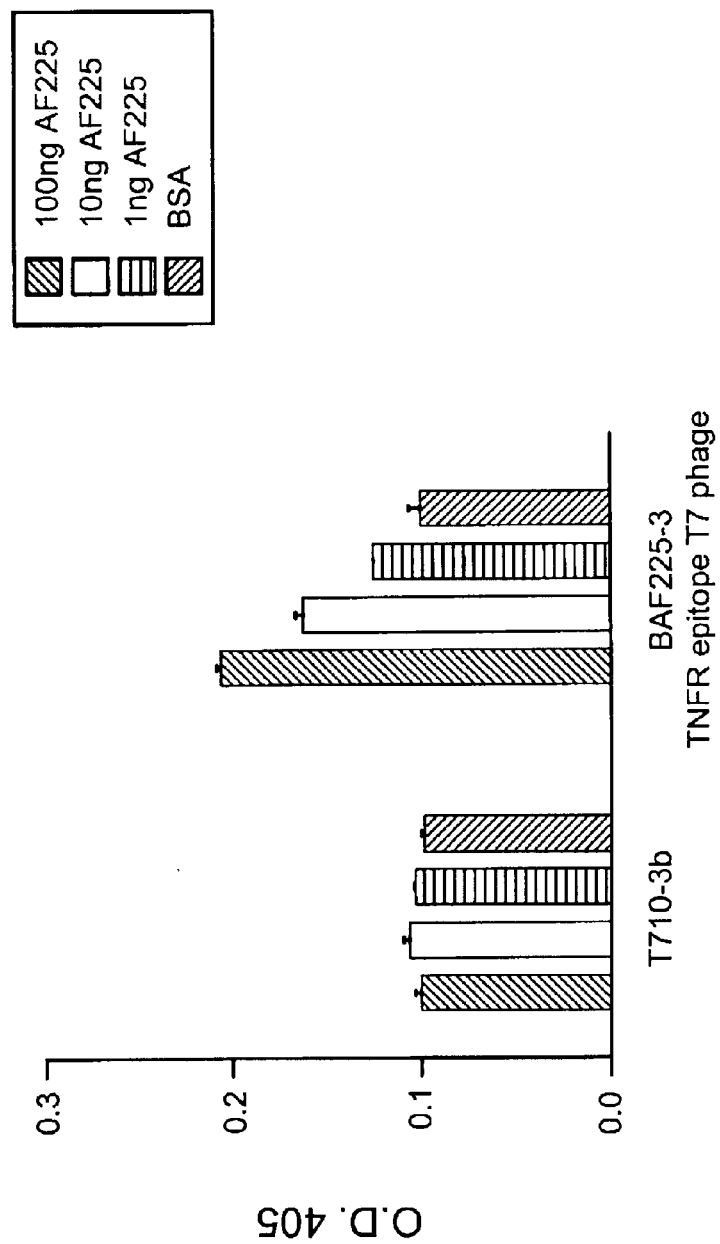
FIG. 4 shows the results of an ELISA of a T7 hTNFR cDNA fragment phage clone captured with the polyclonal anti-TNFR antibody to immobilized hTNFR.

The TNFR epitope phage clone BAF225-3 was specifically captured by the polyclonal anti-hTNFR antibody only in the wells containing immobilized hTNFR, thereby demonstrating the formation of a complex between epitope phage, antibody and target protein (FIG. 4).

EXAMPLE 2

Detection of Anti-hTNFR T7 Phage-Displayed Antibody on a Western Blot of hTNRF 1 ug of soluble human TNFR was loaded on a 4–12% NuPAGE gel (Invitrogen) and electrophoresed for 45 min at 200V, followed by transfer of the protein to a nitrocellulose membrane. The filter was blocked by incubating for 1 h at 4° C. in TBS/5% milk/1% goat serum/0.1% Tween 20. The anti-hTNFR antibody-phage complex was formed by combining $10^{10}$ pfu of purified BAF225-3 phage with 10 ug of the goat anti-hTNFR polyclonal antibody (AF225) and incubating for 1 h at 4° C. The preformed antibody-phage complex was then diluted in 10 ml of TBS/1% milk/0.2% goat serum/0.1% Tween 20 and added to the TNFR blot. Following an overnight incubation at 4° C., the blot was washed several times with PBS/0.1% Tween 20 and then incubated with a polyclonal anti-T7 rabbit antisera followed by an anti-rabbit IgG HRP conjugate. Bound antibody was detected by incubating the blot in TMB substrate solution, which produces a colored precipitate on the blot where enzyme activity is located (see FIG. 5A).

Figures 5A, 5B:
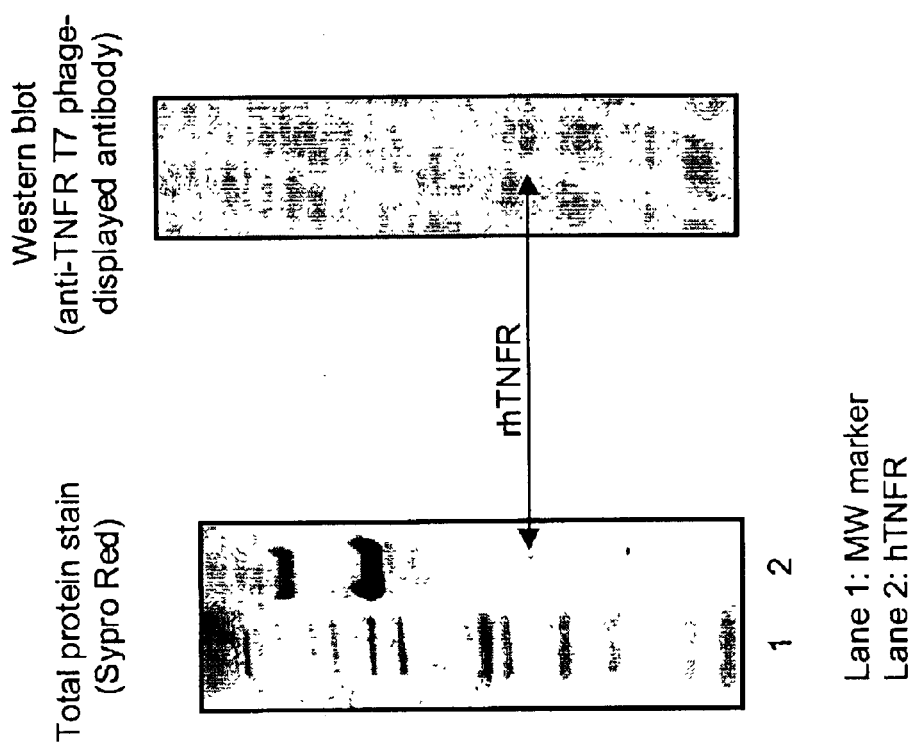
FIGS. 5A and 5B show the detection of rhTNFR on a Western blot probed with an anti-hTNFR T7 phage-displayed antibody.

The approximately 21-kD soluble TNFR protein band was clearly detected with the anti-T7 phage antibody, indicating that the anti-TNFR phage displayed antibody complex was bound to the target protein (FIG. 5B). The large amount of BSA present in the preparation of soluble TNFR, which served as a negative control for non-specific binding, showed no staining.

EXAMPLE 3

Figure 6B:
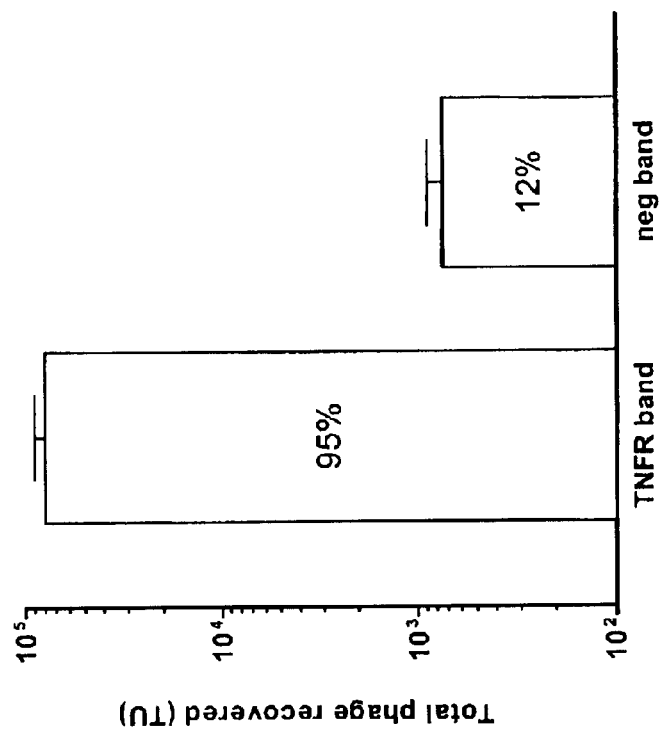
FIGS. 6A and B illustrate the recovery and enrichment of infective target phage particles from anti-hTNFR T7 phage-displayed antibody complexes bound to rhTNFR on a Western blot.
Figure 6A:
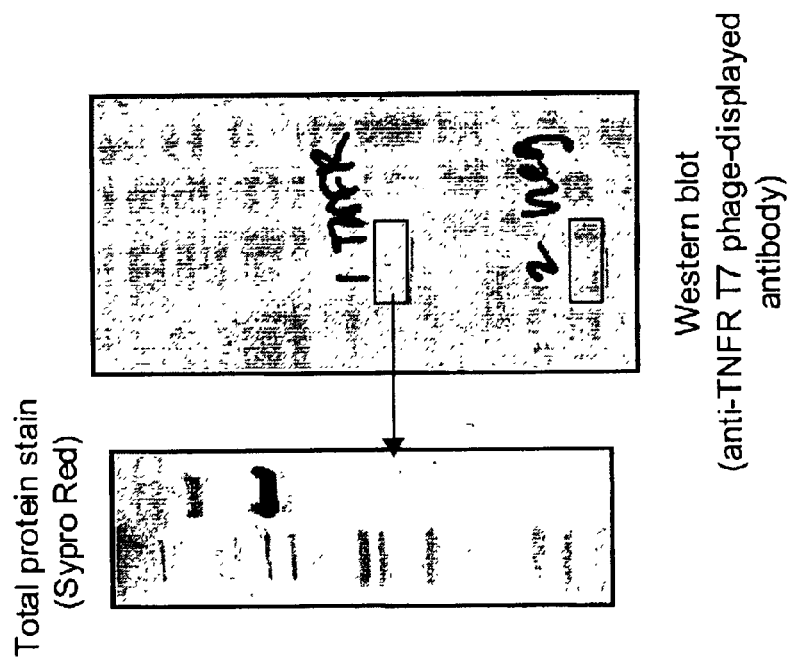

Capture and Recovery of Anti-hTNFR T7 Phage-Displayed Antibody on Western Blot of hTNFR A western blot of soluble hTNFR was prepared as described in the Example 2 to determine if infective phage particles bound to the target protein could be recovered from the blot (see FIG. 6A). To prepare the anti-hTNFR phage antibody complex, a 1:10 mixture of epitope phage (BAF225-3) and wild type T7 10-3b phage was incubated with 10 ug of the goat anti-hTNFR polyclonal antibody (AF225) for 1 h at 4° C. The preformed antibody-phage complex was then diluted in 10 ml of TBS/1% milk/0.2% goat serum/0.1% Tween 20 and added to the TNFR blot. Following an overnight incubation at 4° C. the blot was washed extensively with PBS/0.1% Tween 20. Two regions of the blot, one corresponding to the location of the soluble TNFR protein band and another that served as a negative control, were excised and placed into PBS containing 1% SDS to elute the bound phage. To determine the number of phage recovered from each sample, the eluates were titered by infecting BLT 5615 cells and plating on LB/AMP plates.

Approximately 100-fold more phage were recovered from the TNFR band as from the negative control (FIG. 6B). To determine what proportion of these phage displayed the target epitope, a plaque lift with the anti-epitope antibody (AF225) was performed. 95% of the phage from the TNFR band were target phage, representing an enrichment of 190-fold relative to negative phage, while in the negative control band approximately 10% were target phage, identical to the fraction in the input population. The results indicate that specific phage-antibody complexes form and persist, and retain free epitope-binding sites capable of forming stable interactions with the cognate target protein.

EXAMPLE 4

Detection of hTNFR in a Complex Mixture of Proteins Using T7 Phage-Displayed Anti-hTNFR Antibody 50 ng of soluble hTNFR was combined with 2 ug of MDCK cell total protein extract and electrophoresed on a 4–12% NuPAGE gel as described in Example 2. The separated proteins were transferred to a nitrocellulose filter and the blot was blocked overnight at 4° C. in TBS/5% milk/1% goat serum/0.1% Tween 20. The anti-hTNFR antibody-phage complex was formed by combining $10^{10}$ pfu of purified BAF225-3 phage with 10 ug of the goat anti-hTNFR polyclonal antibody (AF225) and incubating for 1 h at 4° C. The preformed antibody-phage complex was then diluted in 10 ml of TBS/1% milk/0.2% goat serum/0.1% Tween 20 and added to the protein blot. Following an overnight incubation at 4° C., the blot was washed several times with PBS/0.1% Tween 20 and then incubated with a polyclonal anti-T7 rabbit antisera followed by an anti-rabbit IgG HRP conjugate. The blot was then developed in TMB substrate solution to determine the location of immunoreactive protein bands (see FIG. 7A).

The approximately 21-kD soluble TNFR protein band was clearly detected with the anti-T7 phage antibody, indicating that the anti-TNFR phage displayed antibody complex was bound to the target protein (FIG. 7B). No bands were detected on control replica blots probed without epitope phage or the polyclonal anti-TNFR antibody.

EXAMPLE 5

Capture and Display of Antibodies Against the hTNF Receptor on fd Phage Displaying hTNF Receptor cDNA Fragments I. General A cDNA fragment library of the human type I TNF receptor (hTNFR-1) extracellular domain was cloned into a pVIII phagemid expression vector. Depending on the induction conditions used during phage growth, this system produces filamentous phage particles displaying approximately 10 to several hundred copies of the protein encoded by the cloned cDNA sequence fused to the major coat protein pVIII. An anti-rhTNFR-1 phage-displayed antibody reagent was created by mixing a fd-displayed rhTNFR-1 cDNA epitope fragment with a polyclonal antibody for use in a series of feasibility experiments demonstrating: (a) free anti-rhTNFR-1 binding sites are carried by the phage, (b) the binding sites are available for binding to proteins external to the phage, (c) phage displaying the antibodies can be captured on an immobilized form of target protein and detected with several phage-specific and target specific reagents.

II. Preparation of the fd hTNFR cDNA Fragment Library

A cDNA encoding the extracellular domain of the human type I TNF receptor was cloned from human liver cDNA by PCR using gene specific primers. The amplified cDNA was digested with DNaseI in the presence of $MnCl_2$ to produce random double-stranded breaks in the DNA. Fragments of 100 to 300 base pairs in length were gel purified and treated with Klenow fragment of DNA polymerase I to create blunt ends. The cDNA fragments were then ligated to the pVIII phagemid vector (p8cDNA) to obtain a library of inserts of which some are in the correct orientation and same translational reading frame as the major (pVIII) coat protein. The resulting DNA was electroporated into *E. coli* MC1061 F' cells, and the cells were grown without selection at 37° C. for 1 h. The cells were then added to a larger culture of medium containing ampicillin to select for the presence of phagemid, and glucose to repress the expression of the fusion protein. The cells were grown for three to four hours and were then infected with the helper phage M13KO7. Kanamycin was added to the culture to select for the presence of the helper phage and arabinose was added to induce the expression of the recombinant fusion protein. Following overnight incubation at 37° C., the culture was centrifuged at 12,000×g for 15 minutes to pellet the bacterial cells, and the phage containing supernatant was transferred to a new bottle. Fd phage particles were purified from the supernatant by precipitation with polyethylene glycol (PEG 8000) followed by centrifugation at 12,000×g for 15 minutes. The supernatant was removed and the phage pellet was resuspended in PBS.

III. Screening fd hTNFR cDNA Fragment Library Against the Goat Polyclonal anti-rhTNFR Antibody To isolate fd phage clones displaying hTNFR epitope fragments reactive with the goat polyclonal antibody against hTNFR (BAF225), the fragment library was first selected on the immobilized antibody. Six wells of a 96-well microtiter plate were coated with 5 ug NeutrAvidin biotin binding protein and then blocked with PBS/1% BSA. 1 ug of biotinylated polyclonal goat anti-human hTNFR antibody was added to each well and incubated at 4° C. for 1 h, followed by washing with PBS. An aliquot of the fd hTNFR cDNA fragment library was added to each antibody coated well (approximately $10^9$ TU/well) and incubated at 4° C. for 1 h. The wells were washed extensively with PBS to remove unbound phage, and phage bound to the antibody were recovered by adding an acid elution buffer (0.1 M HCl, pH 2.2 with glycine, 0.1% BSA), followed by neutralization with an equal volume of 2M Tris base (pH unadjusted). The eluates were combined and titered on K91 recA cells.

Figure 8:
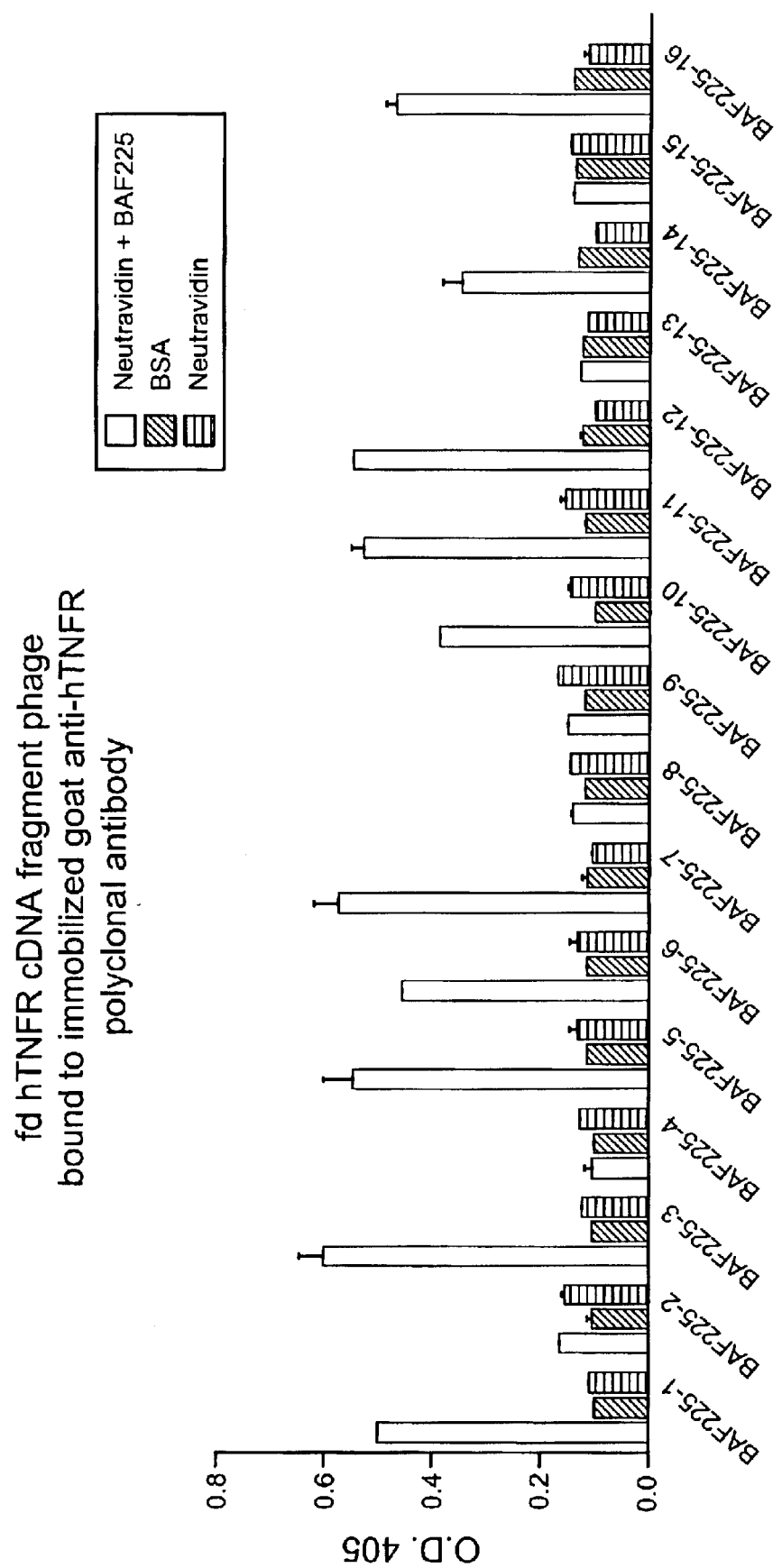
FIG. 8 shows the results of an ELISA of fd phage displaying hTNFR cDNA fragments captured by immobilized goat anti-hTNFR polyclonal antibody.

Random clones from the eluate were grown and tested individually in a phage ELISA against the immobilized polyclonal antibody. For each clone duplicate wells of a 96-well plate were coated with NeutrAvidin and BAF225 as described above, as well as negative control wells that contained only NeutrAvidin or were blocked with PBS/1% BSA. 50 ul of phage supernatant was added to each well and incubated for 1 h at 4° C. The wells were washed with PBS and bound phage were detected by adding 50 ul of an anti-fd antibody conjugated to HRP diluted 1:5000 in PBS/0.1% BSA. The anti-phage antibody was detected by addition of ABTS development buffer. The amount of horseradish peroxidase activity in each well was then measured by reading the absorbance at 405 nm with a microtiter plate reader. Phage displaying epitopes reactive with BAF225 were specifically captured on the antibody coated wells (FIG. 8). Sequencing the TNFR cDNA fragments displayed by the positive clones revealed that multiple epitopes in the extracellular domain of TNFR are recognized by the polyclonal antibodies (FIG. 9).

IV. Capture of hTNFR Epitope fd Phage on Immobilized rhTNFR with a Polyclonal anti-TNFR Antibody 1 ug of an anti-hTNFR monoclonal antibody (MAb 625) was added to wells of a microtiter plate and incubated for 1 h at 37° C. The wells were washed several times with PBS and blocked by adding 300 ul of PBS containing 1% BSA. The plate was washed and 0.1 ng of soluble rhTNFR-1 diluted in PBS/0.1% BSA was added to each well and incubated for 1 h at 4C. Following additional washes with PBS, either 100, 10, or 1 ng of a polyclonal goat anti-hTNFR antibody (AF225) was added to the wells and incubated for 1 h at 4° C. The plate was again washed with PBS and $10^9$ TU of BAF225-10 phage which display an epitope that binds to the goat polyclonal anti-hTNFR antibody were added to the wells and incubated for 1 h at 4° C. Control wild type p8 phage that do not display an anti-TNFR epitope were added to other wells to serve as a negative control. The plate was washed several times with PBS and bound phage were detected by adding an anti-fd antibody conjugated to HRP that was diluted 1:5000 in PBS/0.1% BSA. Bound antibody was detected by the addition of ABTS substrate solution and the absorbance was measured using a microtiter plate reader.

Figure 10A:
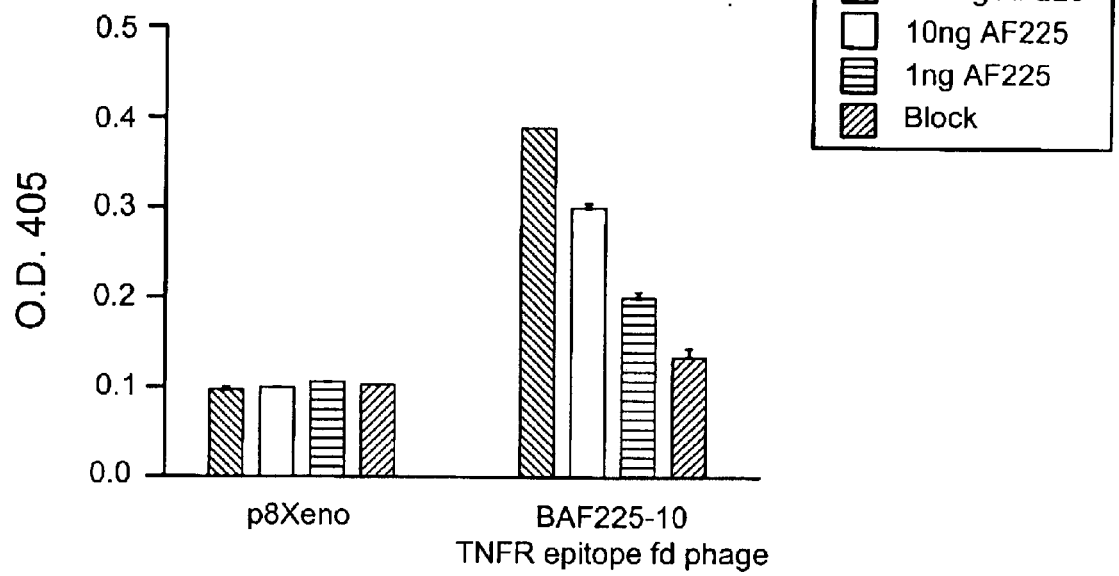
FIGS. 10A and 10B show the results of an ELISA of a T7 hTNFR cDNA fragment phage clone captured with the polyclonal anti-TNFR antibody to immobilized hTNFR.
Figure 10B:
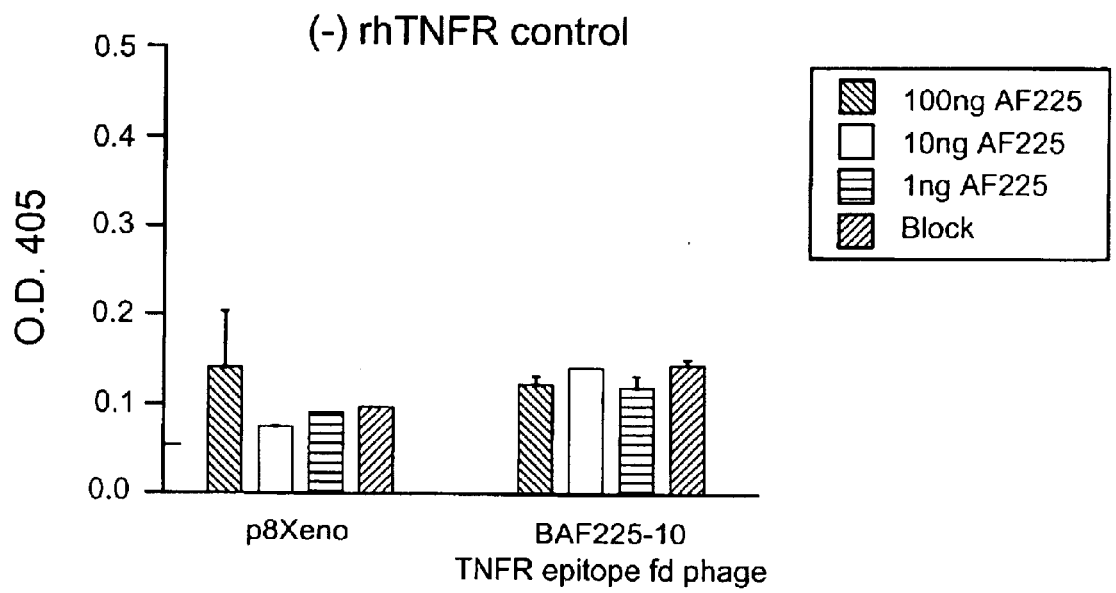

The TNFR epitope fd phage clone BAF225-10 was specifically captured by the polyclonal anti-hTNFR antibody only in the wells containing immobilized hTNFR, thereby demonstrating the formation of a complex between epitope phage, antibody and target protein (FIGS. 10A and 10B).

EXAMPLE 6

Detection of anti-hTNFR fd Phage-Displayed Antibody on Western Blot of hTNRF 1 ug of soluble human TNFR was loaded on a 4–12% NuPAGE gel (Invitrogen) and electrophoresed for 45 min at 200V, followed by transfer of the protein to nitrocellulose. The filter was blocked by incubating for 1 h at 4° C. in PBS containing 1% BSA. The anti-hTNFR antibody-phage complex was formed by combining $10^{10}$ TU of purified BAF225-10 phage with 10 ug of the goat anti-hTNFR polyclonal antibody (AF225) and incubating for 1 h at 4° C. The preformed antibody-phage complex was then diluted in 10 ml of PBS/0.1% BSA and added to the TNFR blot. Following an overnight incubation at 4° C., the blot was washed several times with PBS and then incubated with an anti-fd antibody HRP conjugate. Bound antibody was detected by incubating the blot in TMB substrate solution, which produces a colored precipitate on the blot where enzyme activity is located (see FIG. 11A).

Figures 11A, 11B:
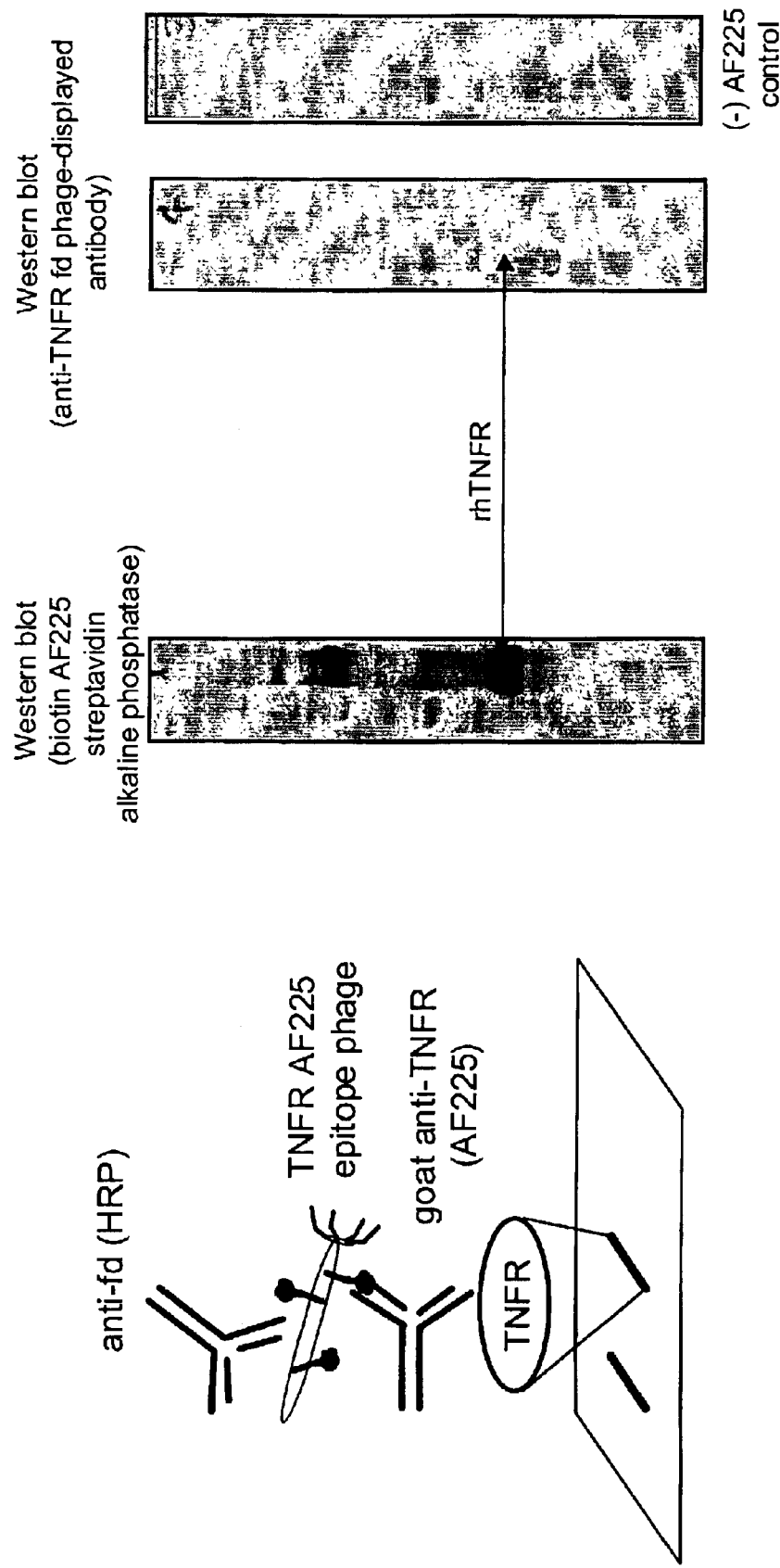
FIGS. 11A and B show the detection of rhTNFR on a Western blot probed with an anti-hTNFR fd phage-displayed antibody.

The approximately 21-kD soluble TNFR protein band was clearly detected with the anti-fd phage antibody, indicating that the anti-TNFR phage displayed antibody complex was bound to the target protein (FIG. 11B). No bands were detected on a second blot that was incubated with epitope phage minus the polyclonal anti-hTNFR antibody. The large amount of BSA present in the preparation of soluble TNFR, which served as a negative control for non-specific binding, also showed no staining.

EXAMPLE 7

Identification of Proteins Separated by 2-D electrophoresis

I. Overview

A polyclonal antibody population is produced against the protein complement of MDCK cells by immunization of rabbits with a mixture of proteins prepared from 5 day differentiated MDCK cell cultures. cDNA is prepared from 2, 3, and 4 day differentiated MDCK cells and cloned into the T7 low and mid-copy expression vectors and fd pIII and pVIII phagemid expression vectors to produce a cDNA display library of the proteins expressed by MDCK cells. The library and the polyclonal Ig preparation are mixed to produce the captured anti-MDCK antibody display library to be used in the following set of experiments.

II. Experimental

A. Isolation of Protein from MDCK Cells

1) Growth of MDCK Cells:

Low passage number MDCK cells are grown in DMEM supplemented with 10% FBS and antibiotics (Kanamycin 100 ug/ml; Penicillin 0.5 units/ml; Streptomycin 0.5 ug/ml) to approximately 80% confluence.

Cells are removed from the dishes with trypsin/EDTA.

Cells are seeded at confluent density (approximately $5 \times 10^5$ cells/cm$^2$) onto tissue culture plates or 0.4 um permeable supports (transwells: 24 mm and 75 mm diameter).

Figure 12A:
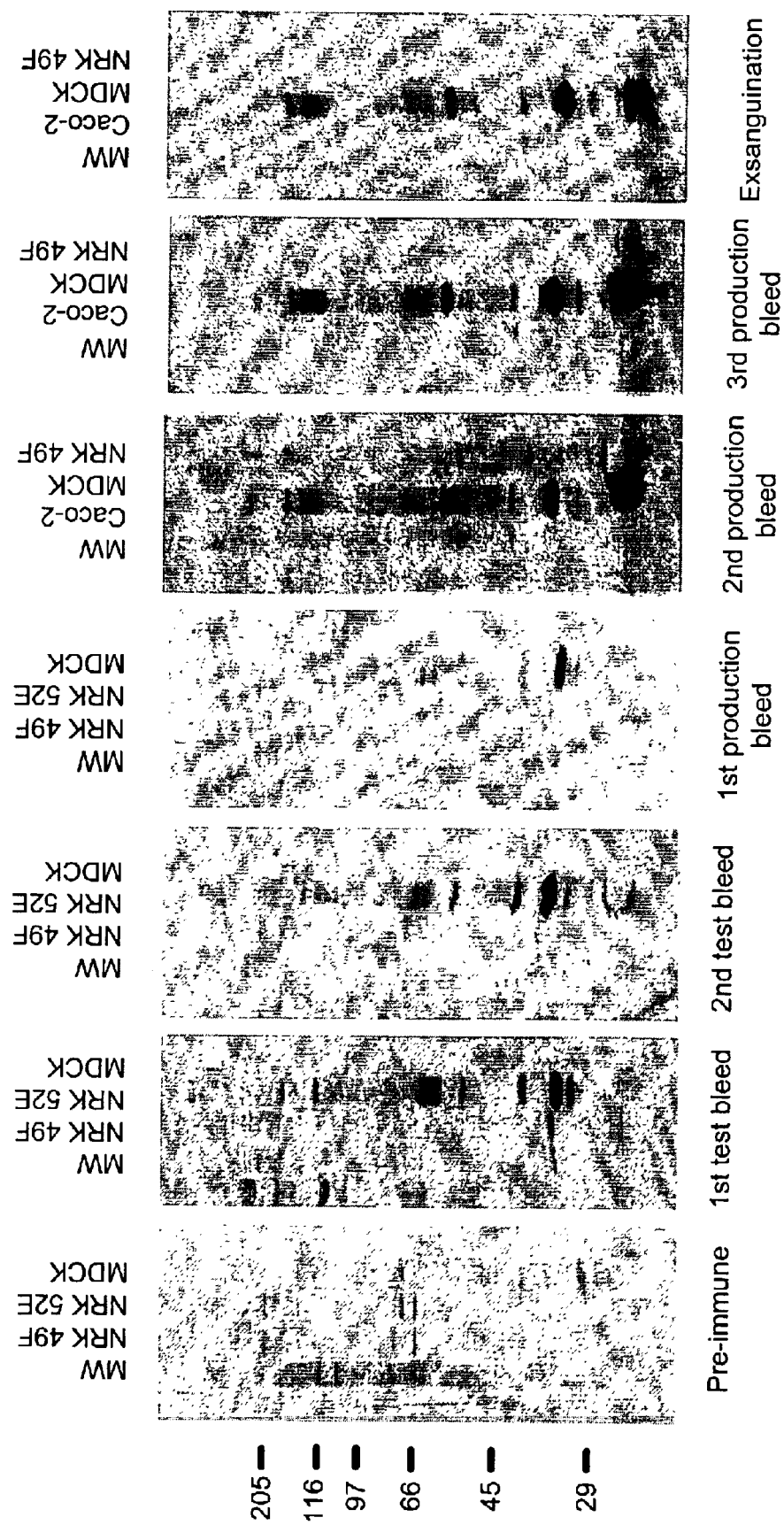
FIGS. 12A and 12B show Western blots of lysates from MDCK, NRK 49F, NRK 52E, and Caco-2 cells separated by SDS-PAGE and probed with various bleeds from 1 of three rabbits inoculated with "live MDCK cell prep" (FIG. 12A) or bleeds from 1 of three rabbits inoculated with "fixed MDCK cell prep" (FIG. 12B) and visualized using $^{125}$I-labeled goat anti-rabbit secondary Ab.
Figure 12B:
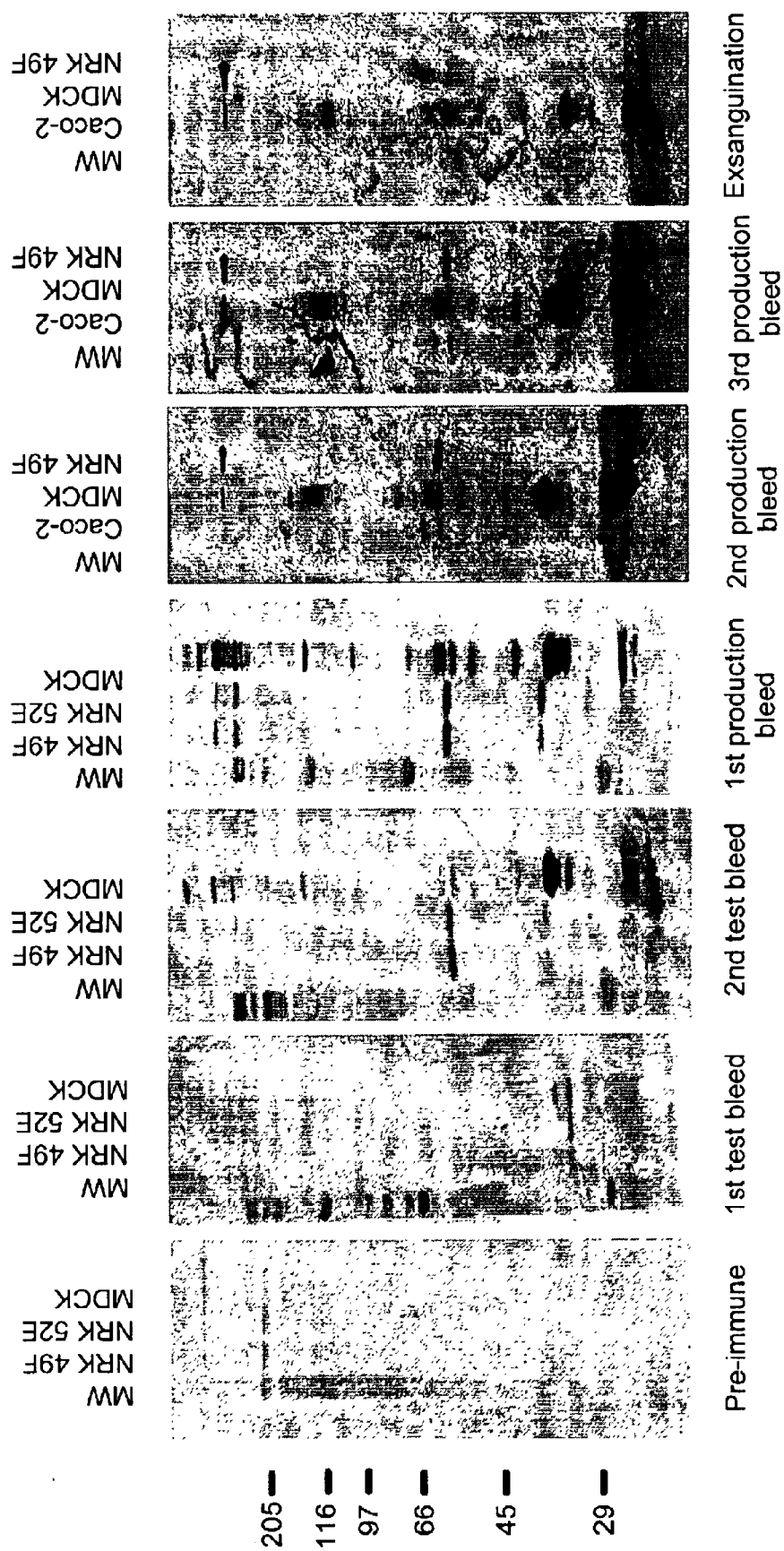
Figure 13B:
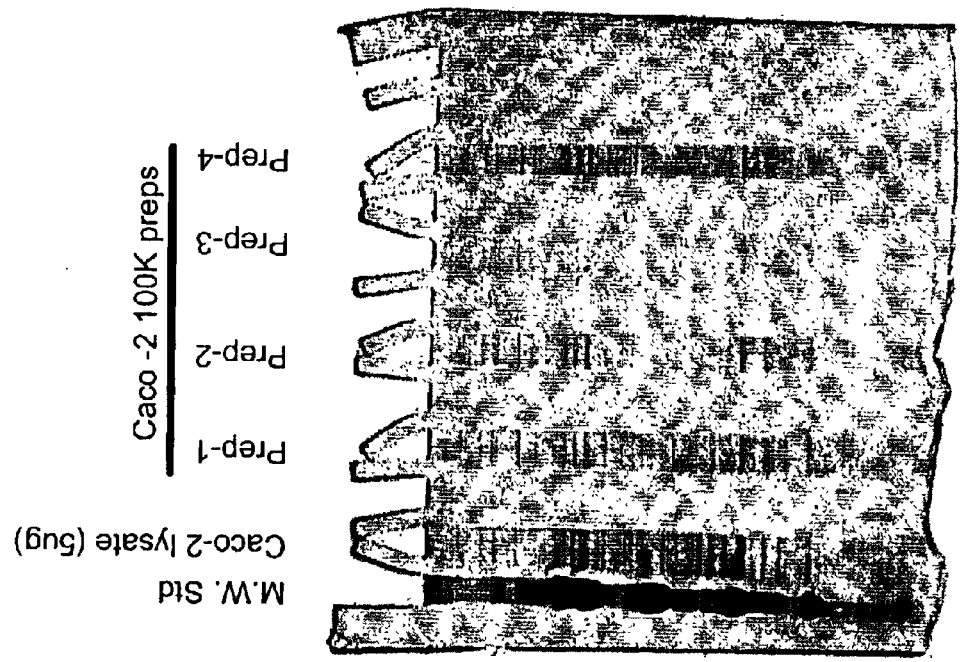
FIGS. 13A and 13B show samples of 100K membrane preparations from differentiated MDCK cells (FIG. 13A) and Caco-2 cells (FIG. 13B) separated by SDS-PAGE and visualized by staining the proteins with SyproRuby.
Figure 13A:
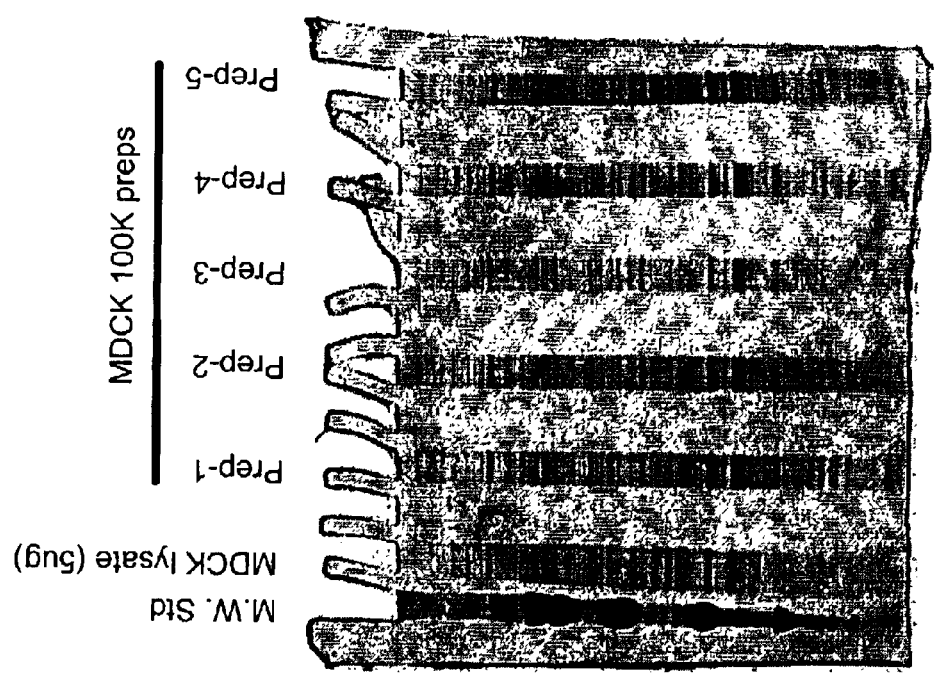
Figure 14A:
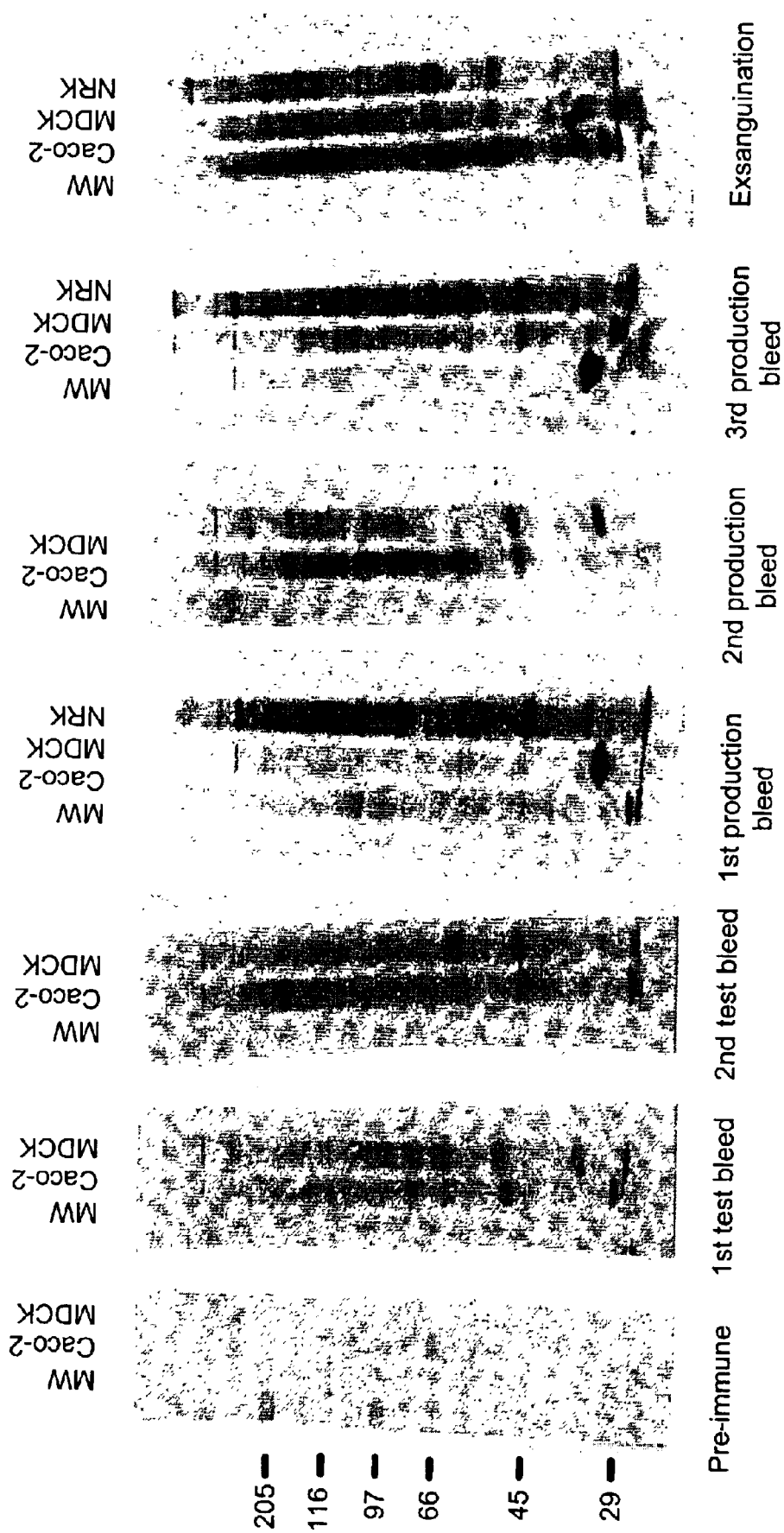
FIGS. 14A and 14B show Western blots of lysates from MDCK, NRK 49F, NRK 52E, and Caco-2 cells separated by SDS-PAGE and probed with various bleeds from 1 of three rabbits inoculated with "MDCK 100k mem prep" (FIG. 14A) or bleeds from 1 of three rabbits inoculated with "Caco-2 100k mem prep" (FIG. 14B) and visualized using $^{125}$I-labeled goat anti-rabbit secondary Ab.
Figure 14B:
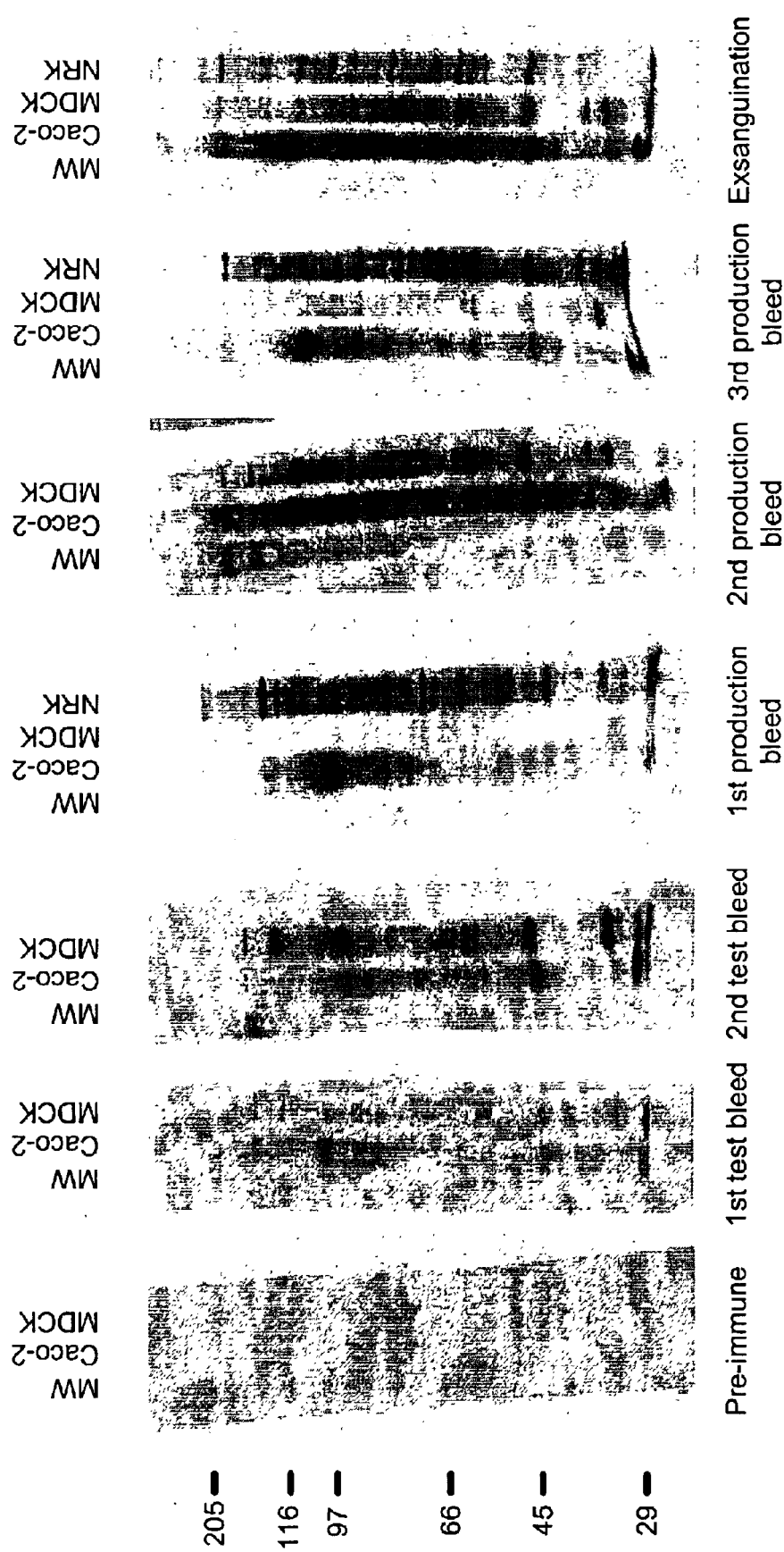

Cells are returned to the incubator for 5 days, changing medium every other day, to establish differentiated monolayers 2) Preparation of Whole Cells and Protein Fractions for Use as Immunogens As described supra, proteins used as immunogens can be of a variety of different types (including, but not limited to, protein fractions isolated from cells or tissues, proteins expressed from a cDNA display library, and random populations of peptides). These proteins can be used as immunogens to prepare antibodies using a number of different formats as described above. Furthermore, a number of approaches can be used to generate a distinct population of proteins from whole cells to use as immunogens for the preparation antibodies. This means focused antibody populations can be prepared from a number of different sources including, but not limited to, whole cells, cell surface proteins, proteins associated with various membrane fractions (e.g., proteins from the endoplasmic reticulum, Golgi, endosome, plasma membrane, and soluble proteins).

a) Isolation of Total Protein from Cells Grown on Plastic or Permeable Support:

Cells are grown on either a plastic or a permeable support (e.g., Costar Transwell Filters) for an appropriate period of time (e.g., 5 days past confluence for differentiated MDCK cells, 14–21 days for polarized Caco-2 cells, or to confluence for non-polarized cells). Filters/plates are placed on ice and washed 3× with ice-cold Ringer's saline (10 mM HEPES, pH 7.4, 150 mM NaCl, 7.2 mM KCl, 1.8 mM $CaCl_2$). The cells are then extracted by adding extraction buffer [0.5% Triton X-100, 300 mM Sucrose, 10 mM PIPES, pH 6.8, 50 mM NaCl, 3 mM $MgCl_2$ and 1×protease inhibitors (antipain (10 μg/ml); leupeptin (10 μg/ml); and pepstatin A (10 μg/ml) plus 1 mM pefablock)] to both apical and basal chambers and rocking gently for 30 min at 4° C. The lysates are then transferred to a clean tube (combining multiple samples if necessary). The filters/plates are scraped and the material collected is combined with the lysates. The samples are vortexed and placed on ice for 10 min. The samples are then transferred to a microfuge tube and centrifuged at 20,000×g for 10 min. The supernatant is then transferred to a new tube. The protein concentration of the sample is measured and adjusted to 1 mg/ml. Note: alternative detergents can be used for extraction (for example 1% SDS; 2% CHAPS; 0.5% TX-100 and 1% Dexoycholate and 0.1% SDS), but must be dialyzed against an isotonic salt solution with minimal detergent present to maintain solubility of integral membrane proteins.

b) Isolation of Domain Specific Plasma Membrane Protein Fractions from Cells Grown on Permeable Supports:

Cells are grown on a permeable support (e.g., Costar Transwell Filters) for an appropriate period of time (e.g., 5 days past confluence for differentiated MDCK cells, 14–21 days for polarized Caco-2 cells). Filters are placed on ice and washed 3× with ice-cold Ringer's saline (10 mM HEPES, pH 7.4, 150 mM NaCl, 7.2 mM KCl, and 1.8 mM $CaCl_2$). Cells are then treated with a membrane impermeant biotinylation reagent (for example EZ-Link sulfo-NHS-S-S-Biotin, EZ-Link sulfo-NHS-LC-LC-Biotin). Biotinylation reagent (made up as 400×stock in DMSO) diluted to 750 uM in Ringer's saline (10 mM HEPES, pH 7.4, 150 mM NaCl, 7.2 mM KCl, 1.8 mM $CaCl_2$) is then applied. Apply 1 ml/4 ml biotin solution apical or 2 ml/6 ml basal for 24 mm/75 mm transwells, respectively, and rocked at 4° C. for 20 min. Ringer's saline is applied to the opposite chamber (1 ml/4 ml apical or 2 ml/6 ml basal for 24 mm/75 mm transwells, respectively) if doing domain specific cell surface labeling. After 20 min, aspirate and then repeat the treatment with fresh biotin solution, as above. Cells are extracted in 1 ml (24 mm)/10 ml (75 mm) extraction buffer [0.5% Triton X-100, 300 mM Sucrose, 10 mM PIPES, pH 6.8, 50 mM NaCl, 3 mM $MgCl_2$ and 1×protease inhibitors (antipain (10 μg/ml), leupeptin (10 μg/ml) plus 1 mM pefablock)] to both apical and basal-lateral sides and rocked gently for 30 min at 4° C. An equal volume of extraction buffer is applied to both apical and basal-lateral sides and rocked gently for 30 min at 4° C. The lysates are then transferred to a clean tube (combine multiple samples if necessary). The filters are scraped and the material collected is combined with the lysates. The samples are vortexed and placed on ice for 10 min. Lysates are transferred into 1.5 ml tubes (1 ml/tube) and 50 ul Pansorbin added to each and mixed 30 min at 4° C. to pre-clear (pansorbin pre-washed 2× and resuspended in extraction buffer and 1×P.I. and 1 mM pefablock). The samples are then centrifuged at 20,000×g for 10 min. The supernatant is then transferred to a new tube. 100 ul of neutravidin agarose is added to each tube and incubated overnight at 4° C. on rotator (neutravidin agarose pre-washed 2× and resuspended in extraction buffer and 1×P.I. and 1 mM pefablock). Samples are centrifuged at 2000×g for 1 min. Beads are washed 2× with High Stringency buffer (0.1% SDS, 1% deoxycholate, 0.5% Triton X-100, 20 mM Tris pH 7.5, 120 mM NaCl, 25 mM KCl, 5 mM EDTA and 5 mM EGTA), 2× with High Salt buffer (0.1% SDS, 1% deoxycholate, 0.5% Triton X-100, 20 mM Tris pH 7.5, 120 mM NaCl, 25 mM KCl, 5 mM EDTA, 5 mM EGTA and 1 M NaCl), and 2× with Low Salt buffer (2 mM EDTA, 10 mM Tris pH 7.5). Beads are then resuspended in an isotonic buffer and proteins left on beads are used directly as immunogens in the case of non-reducible biotinylation reagents. If necessary, when using a reducible biotinylation reagent (for example EZ-Link sulfo-NHS-S-S-Biotin), proteins can be eluted from beads by addition of 200 ul/tube of Homogenization Buffer (20 mM HEPES/KOH, pH 7.2, 90 mM KOAc, 2 mM $Mg(OAC)_2$, 250 mM Sucrose), 5% BME, 1×protease inhibitors, and 1 mM pefablock for 1 h at room temperature.

c) Preparation of Whole Cells (Live and Fixed) for Use as Immunogens:

The protocol used for MDCK cells but can be adapted to other cell types as well. Cells were harvested and plated at sufficient density to reach approximately 70% confluence 2 days after plating (sufficient time for the full compliment of cell surface proteins to be expressed properly, but brief enough to allow removal of cells from flask). After two days, cells were washed 3× with PBS and released from the flasks with versene to ensure that cell surface proteins were not compromised. The cells were then pelleted by low speed centrifugation and either: 1) resuspended in freezing medium (50% DMEM, 40% FBS and 10% DMSO) and slowly frozen and stored in liquid nitrogen to maintain cell viability or 2) washed 4× with PBS, fixed in 4% paraformaldehyde for 30 min on ice, then washed 4× with TBS (10 mM Tris pH 7.4, 120 mM NaCl) plus 50 mM $NH_4Cl$. In both cases, cells were resuspended $1\times10^7$ cells/vial for each inoculation of rabbits or $1\times10^6$ cells/vial for each inoculation of mice. FIGS. 12A and 12B show lysates from MDCK, NRK 49F, NRK 52E, and Caco-2 cells separated by SDS-PAGE and probed with various bleeds from 1 of three rabbits inoculated with "live MDCK cell prep" (FIG. 12A) or bleeds from 1 of three rabbits inoculated with "fixed MDCK cell prep" (FIG. 12B).

d) Preparation of Plasma Membrane Enriched Fraction for Use as Immunogens:

The protocol used for differentiated MDCK (5 days past confluence) and Caco-2 cells (grown for 19–21 days past confluence) grown on 75 mM Transwells can be adapted to other cell types grown on plastic or permeable supports. Cells were placed on ice and washed 3× with ice-cold Ringer's saline (10 mM HEPES, pH 7.4, 150 mM NaCl, 7.2 mM KCl, 1.8 mM $CaCl_2$) and 1× with homogenization buffer (20 mM HEPES/KOH pH 7.2, 90 mM KOAc, 2 mM $Mg(OAc)_2$, 250 mM sucrose). Cells were scraped from the filter in homogenization buffer containing protease inhibitors (antipain (10 μg/ml), leupeptin (10 μg/ml) plus 1 mM pefablock). Cells were combined in a 50 ml conical tube and centrifuged at 2000×g for 10 min at 4° C. Cells were then resuspended in a minimal volume of homogenization buffer containing protease inhibitors. The cells were gently fragmented by passing the sample through a ball bearing homogenizer multiple times (minimal clearance between the bore of the chamber and the ball bearing ensure that the cell are fragmented without disrupting organelles). The homogenate was transferred to microfuge tubes and centrifuged at 2000×g for 10 min. The supernatant was transferred to a new microfuge tube. The pellet was resuspended in a minimal volume and re-homogenized as above. The second homogenate was transferred to microfuge tubes and centrifuged at 2000×g for 10 min to pellet any remaining unbroken cells and nuclei. The supernatant from the second homogenate was combined with the supernatant from the first homogenization. The sample was then centrifuged at 10,000×g for 10 min to remove large membrane components (for example mitochondria and endoplasmic reticulum). The supernatant was then centrifuged at 100,000×g for 45 min to produce an enriched plasma membrane fraction. The supernatant was discarded and the pellet resuspended in homogenization buffer containing protease inhibitors. A protein assay was preformed to determine the protein concentration in each sample. Based on the results from the protein assay, the samples were examined by SDS-PAGE (FIGS. 13A and 13B). The results from the SDS-PAGE analysis were used to estimate the actual protein concentration in each sample prior to its use as an inoculum. FIGS. 14A and 14B show lysates from MDCK, NRK 49F, NRK 52E, and Caco-2 cells separated by SDS-PAGE and probed with various bleeds from 1 of three rabbits inoculated with "MDCK 100k mem prep" (FIG. 14A) or bleeds from 1 of three rabbits inoculated with "Caco-2 100K membrane prep" (FIG. 14B).

B. Preparation of Rabbit Antibody Against Total MDCK Protein Preparation

2–3 rabbits are used for each antigen pre-immune bleeds are collected from each rabbit and screened against the antigen preparation rabbit polyclonal antibodies are raised against protein preparations isolated as outlined above using a standard 94 day protocol (Covance):

500 ug of antigen is used for the initial immunization and 250 ug of antigen for each subsequent boost each rabbit is given four boosts based on a three-week cycle of boost, in which a 50 ml sample of blood is collected 10 days after each boost following the fourth boost rabbits are exsanguinated serum is collected from each bleed and titered against the antigen serum from each production sample is then screened by western blot against the antigen.

immunoreactive serum samples are affinity purified by isolation on protein-A Sepharose and salt elution C. Preparation of cDNA from MDCK Cells 1) Growth of cells: as above.

2) Isolation of mRNA: MDCK cells are removed from the Transwell filter by scraping and the cell suspension is transferred to a centrifuge tube. The cells are pelleted by centrifugation at 300×g for 10 minutes. Total mRNA is isolated by disrupting the cells in the presence of guanidine isothiocyanate followed by the addition of ethanol to provide the appropriate conditions for binding RNA to the silica-based membrane in the spin column (according to manufacturers protocols for RNeasy kit obtained from Qiagen). The column is washed several times and purified RNA is eluted with water. mRNA is isolated by mixing the total RNA preparation with an equal volume of 20 mM Tris-Cl, pH 7.5, 1M NaCl, 2 mM EDTA, 0.2% SDS, followed by incubating the sample for 3 min at 70° C. The sample is then incubated at room temperature with $dC_{10}T_{30}$ oligonucleotides that are covalently attached to the surface of polystyrene-latex particles (Oligotex columns obtained from Qiagen). The column is washed several times and poly A+ mRNA is eluted in 5 mM Tris-HCl, pH 7.5.

3) Synthesis of cDNA: Poly A+ RNA is primed with oligo (dT) or HindIII random hexamer primers $d(N_6TT)$ in the appropriate buffer and first strand synthesis is initiated by the addition of dNTPs and MMLV reverse transcriptase. RNAse H and DNA polymerase I are used for second strand synthesis, followed by treatment with T4 polymerase to blunt the ends of the cDNA. First and second strand synthesis reactions are carried out in the presence of 5-methyl dCTP, which protects any internal EcoRI and HindIII restriction sites from digestion in subsequent steps. EcoRI/HindIII directional linkers d(GCTTGAATTCAAGC; SEQ ID NO:18) are ligated to the cDNA. The ligase is heat inactivated by incubating at 70° C. for 10 minutes and the sample is cooled slowly to room temperature. The cDNA directional linkers d(GCTTGAATTCAAGC; SEQ ID NO:18) are ligated to the cDNA. The ligase is heat inactivated by incubating at 70° C. for 10 minutes and the sample is cooled slowly to room temperature. The cDNA is then digested with EcoRI and HindIII and passed through a small gel filtration column to remove excess linkers and small cDNA products (<300 bp).

4) Preparation of cDNA fragments: Poly A+ RNA is primed with oligo (dT) or random hexamer primers $d(N_6)$ in the appropriate buffer and first strand synthesis is initiated by the addition of dNTPs and MMLV reverse transcriptase. RNaseH and DNA polymerase I are used for second strand synthesis. The cDNA is then digested with DNaseI in the presence of $MnCl_2$ to produce random double-stranded breaks in the DNA. Fragments of 100–300 base pairs in length are gel purified and treated with Klenow fragment of DNA polymerase I to create blunt ends.

D. Preparation of cDNA Library in T7

1) Preparation of T7 vector DNA: CsCl purified T7 phage (described above) are dialyzed in 0.1 M NaCl, 0.1 M Tris-HCl, pH 8.0. The phage solution is then extracted three times with an equal volume of phenol equilibrated with 0.1 M Tris (pH 7.5), followed by two extractions with an equal volume of chloroform:isoamyl alcohol (24:1 v/v). The final aqueous phase is dialyzed in TE buffer overnight at 4° C. 100 ug of vector DNA is digested with EcoRI and HindIII in the appropriate buffer overnight at 37° C. to clone the full-length cDNAs or EcoRV to clone the blunt ended cDNA fragments. The restriction enzymes are heat inactivated by incubating the sample at 65° C. for 20 minutes. The vector arms are dephosphorylated by the adding 50 units of calf intestine alkaline phosphatase to the DNA in the appropriate buffer and incubating at 37° C. for 1 hour. The sample is then extracted one time with an equal volume of phenol:chloroform (1:1) and passed through a small gel filtration column.

Ligation and purification: 2 ug of prepared vector arms are mixed with a 2-fold molar excess of cDNA and ligated with T4 DNA ligase overnight at 16° C. The ligation mixture is incubated with an in vitro packaging extract, and the phage products are used to infect a suitable bacterial host. Large amounts of phage can be prepared by infecting a culture of bacterial cells grown in M9TB to an $OD_{600}$ of 0.6–0.8 with the packaging reaction. The culture is incubated with shaking at 37° C. for 1–3 hours until lysis is observed. The lysate is clarified by centrifugation at 8,000×g for 10 minutes. T7 phage are purified from the cleared supernatant by precipitation with polyethylene glycol (PEG 8000) followed by banding in a CsCl step gradient.

E. Preparation of cDNA Library in fd pIII and pVIII Phagemid Expression Vectors

Double-stranded Phagemid Vector DNA is isolated using Qiagen Plasmid Maxi columns. 100 ug of each vector is digested with EcoRI and Hind III in the appropriate buffer overnight at 37° C. The restriction enzymes are heat inactivated by incubating the sample at 65° C. for 20 minutes. To clone cDNA fragments the digested vectors are treated with Klenow fragment in the presence of all four dNTPs to create blunt ends. The vectors are dephosphorylated by adding 50 units of calf intestine alkaline phosphatase to the DNA in the appropriate buffer and incubating at 37° C. for 1 hour. The samples are extracted one time with an equal volume of phenol:chloroform (1:1) and passed through a small gel filtration column.

10 ug of each vector is mixed with a 2-fold molar excess of cDNA and ligated with T4 DNA ligase overnight at 16° C. Each ligation mix is electroporated into $E.\ coli$ MC1061 F' cells, and the cells are grown without selection at 37° C. for 1 hour. The cells are then added to larger cultures of medium containing ampicillin to select for the presence of phagemid, and glucose to repress the expression of the fusion protein. The cells are grown for three to four hours (approximately 10-doublings) and are then infected with helper phage. Kanamycin is added to cultures to select for the presence of helper phage and arabinose is added to induce the expression of the recombinant fusion protein. Following an overnight incubation at 37° C., the cultures are centrifuged at 12,000×g for 15 minutes to pellet the bacterial cells, and the phage containing supernatants are transferred to new bottles. Fd phage are purified from each supernatant by precipitation with polyethylene glycol (PEG 8000) followed by centrifugation at 12,000×g for 15 minutes. The supernatant is removed and the phage pellet is resuspended in PBS.

F. Preparation of cDNA Expression Library Fused to GST for Immunization 1) cDNA prepared as described above is digested with the EcoRI and HindIII and inserted into an expression vector that places the cDNA in the same translational reading frame as the gene for glutathione-S-transferase (GST) (pET vectors obtained from Novagen). The plasmid construct is transformed into $E.\ coli$ BL21 (DE3) to allow controlled expression of the GST fusion protein.

2) Bacterial cells harboring the GST fusion vector are typically grown at 37° C. to an OD600 of ~0.8 and IPTG is added to a final concentration of 1 mM to induce expression of the fusion protein. The cells are grown for an additional 2.5 hours at 37° C. and pelleted by centrifugation at 3000×x g for 10 minutes. Proteins are extracted from the cells using B-Per Reagent (Pierce) according to the manufacturer's directions. GST-cDNA fusion protein is purified from the total protein preparation by incubating the extract with immobilized glutathione. Bound fusion protein is released by the addition of elution buffer containing reduced glutathione. The purified protein is dialyzed in PBS overnight at 4° C.

G. Use of GST-fused cDNA for Immunizing Rabbits

1) Preparation of rabbit antibody against total GST-cDNA expression library protein mixture 2–3 rabbits are used for each antigen preparation pre-immune bleeds are collected from each rabbit and screened against the antigen preparation rabbit polyclonal antibodies are raised against protein preparations isolated as outlined above using a standard 94 day protocol (Covance):

500 ug of antigen is used for the initial immunization and 250 ug of antigen for each subsequent boost each rabbit is given four boosts based on a three-week cycle of boost, in which a 50 ml sample of blood is collected 10 days after each boost following the fourth boost rabbits are exsanguinated serum is collected from each bleed and titered against the antigen serum from each production sample is then screened by western blot against the antigen immunoreactive serum samples are affinity purified by isolation on protein-A Sepharose and salt elution H. Capture of Antibodies on cDNA Library products Displayed on Phage Phage particles from the MDCK cDNA display library are grown and purified as described to produce approximately $10^{13}$ phage particles (or about $10^7$ library equivalents from a library of $10^6$ independent recombinants). Ig fraction from the anti-MDCK polyclonal is concentrated to less than or equal to 1 mg/ml protein, and 1–10 ml is mixed with $10^{13}$ pfu of the library, incubated overnight at 4° C. Immediately before use, phage particles and free antibody are separated by pelleting the phage at 300,000×g for 30 min and resuspending in 10 ml (or less) PBS.

I. Separation and Blotting of Total Protein from MDCK Cells on SDS-PAGE and 2-D IEF/SDS-PAGE 1. 1-D SDS-PAGE pour 7.5% SDS-PAGE gels add equal volume of SDS-PAGE sample buffer containing 200 mM DTT and 2% β-mercaptoethanol to each sample and mix heat samples at 100° C. for 10 min load samples on gel run gels at 8 mA per gel overnight Electrophoretic Protein Transfer to Immobilon PVDF pre-wet membranes in 100% methanol transfer proteins for 4 hr at 250 mA (->1 Amp-hr)

block blots in Tris buffered saline (TBS) (10 mM Tris-HCL, pH 7.4, 120 mM)+5% milk+1% goat serum+0.1% $NaN_3$ overnight at 4° C.

rinse blots once, then wash 1×5 min in TBS+0.1% Tween-20 wash 1×5 min in HBS

Staining Blots with a Library of Phage-cDNA/Ab Complexes probe blots with phage-displayed cDNA library/antibody reagent at $10^{10}$–$10^{12}$ phage particles in TBS+1% milk+0.2% goat serum for 1 hour at room temp on belly dancer rinse blots 2×, then wash 4×10 min with TBS+0.1% Tween-20 wash 1×5 min with TBS incubate blots with biotinylated anti-phage antibody (1 ug/ml) diluted in TBS+1% milk+0.2% goat serum for 1 hour at room temp on belly dancer rinse blots 2×, then wash 4×10 min with TBS+0.1 % % Tween-20 wash 2×5 min with TBS incubate blots with fluorescein conjugated neutavidin diluted to 1 ug/ml in TBS+1% milk+0.2% goat serum for 1 hour at room temp on belly dancer rinse blots 2×, then wash 4×10 min with TBS+0.1 % % Tween-20 wash 2×5 min with TBS expose to Typhoon fluorescence array detector (Molecular Dynamics, Sunnyvale, Calif.) as required 2. 2-D Gels Pour Isoelectric-focusing Gel prepare acrylamide gel solution in side-arm flask. For 40 ml:

21.86 g urea (9.1 M final)

8 ml 10% (v/v) Triton X-100 (2% v/v final)

3.6 ml water 10 ml acrylamide/bis stock solution (30:0.8%)

1.6 ml ampholytes pH 5–7 (Pharmacia, ampholynes) (40% stock->1.6% final)

0.4 ml ampholytes pH 3–10 (Pharmacia, pharmolytes) (36% stock ->0.36% final)

de-gas solution add 80 µl of 10% APS and 40 µl TEMED and mix pour tube gels

Run Isoelectric-focusing Gel prepare sample thaw lysate add dry urea to 9 M final concentration volume increased 1.6-fold (to 373 µl)

want composition of sample following addition of lysis buffer to be:
        9.1 M urea
        2% Triton X-100
        5% β-mercaptoethanol
        1.6% ampholytes pH 5–7
        0.36% ampholytes pH 3–10 add equal volume of "2X" lysis buffer containing:
        2.73 g urea (9.1 M in "2×")
        2 ml 10% Triton X-100
        0.5 ml β-mercaptoethanol (10% in "2×")
        0.4 ml ampholytes pH 5–7 (3.2% in "2×")
        0.1 ml ampholytes pH 3–10 (0.72% in "2×")
        water, to 5 ml final volume centrifuge sample 5 min at room temperature, 20,000×g to pellet insoluble aggregates load sample onto tube gel apply overlay solution 1.9 g urea (3 M final)

0.67 ml 10% Triton X-100 (0.67% final)

167 µl β-mercaptoethanol (1.67% final)

133 µl ampholytes pH 5–7 (0.53% final)

33 µl ampholytes pH 3–10 (0.12% final)

add a few grains of bromophenol blue water, to 10 ml final volume gently overlay the overlay with de-gassed 20 mM NaOH, being careful not to disturb sample fill lower buffer chamber (anode) with 20 mM $H_3PO_4$ place gel in tank and fill upper chamber (cathode) with de-gassed 20 mM NaOH connect power supply and apply voltage, using a constant power setting of 3 watts, limit voltage to 600 V Measure pH of IEF Gel for Extra 1-D Gel set up 24 tubes, each containing 1 ml high purity, de-gassed water briefly rinse IEF gel in water place gel on glass plate and dissect into 24×0.5 cm pieces place gel pieces, in order, into tubes soak in water on shaker for 2–3 hr read pH of each tube Stain IEF Gels with Coomassie or Silver stain one gel with Coomassie Blue overnight; destain fix other gel in 30% ethanol/10% acetic acid for silver staining silver stain: follow protocol in Molecular Cloning Lab Manual (Sambrook et al. (1989) Molecular Cloning: A Laboratory Manual, 2nd Ed., Cold Spring Harbor Laboratory Press, Cold Spring Laboratory, N.Y.).

Run Second Dimension Laemmli gels pour 7.5% Laemmli gels, using 3 mm spacers and comb to generate one long well (~13 cm)

equilibrate each tube gel in 15 ml equilibration buffer for 5–7 min

3% (w/v) SDS 0.4 mM EDTA

10% (v/v) glycerol 20 mM TrisHCl, pH 6.8

1.7% 2-mercaptoethanol bromophenol blue fill Laemmli gel well with SDS-PAGE running buffer place IEF gel in well of Laemmli gel (acidic end to the left/basic end to the right)

drain buffer from well and carefully overlay IEF strip with agarose/equilibration buffer mixture make 2% (w/v) L.M.P. agarose, melt and keep at 40° C.

mix 1:1 with equilibration buffer also mix 50 µl MW standards with 50 µl agarose/equilibration buffer and load into MW lanes after agarose has set, assemble electrophoresis tank, overlay gels with SDS-PAGE tank buffer and run at constant current (15 mA/gel) for 5 hr turn down to 8 mA/gel overnight (16 hr)

turn up to 30 mA/gel for final 6 hr

Electrophoretic Protein Transfer (One 2-D Gel)

pre-wet immobilon PVDF membrane in 100% methanol transfer proteins 20 hr @ 100 mA (~2 Amp-hr) in 1×Towbin+5% Methanol at 4° C.

block blots in HBS+5% milk+1% goat serum+0.1% $NaN_3$ at room temp for 1 hr

Stain Blot with Phage-cDNA Library/Ab Reagent as Above for 1-D Gels

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

What is claimed is:

1. A method of analyzing an amino acid sequence of polypeptides by determining whether they share an epitope, the method comprising:
   (a) providing a population of replicable genetic package/antibody reagents, each replicable genetic package/antibody reagent (package/antibody reagent) comprising (i) a replicable genetic package having a heterologous nucleic acid segment that encodes a first polypeptide displayed on the replicable genetic package and (ii) a captured antibody having a plurality of binding sites, each site having specific affinity for the first polypeptide, with at least one of the sites available for binding, the first polypeptide and the captured antibody complexed with it varying between at least some of the package/antibody reagents;
   (b) contacting the population of package/antibody reagents with a second polypeptide, whereby package/antibody reagents bearing captured antibodies having specific affinity for the second polypeptide bind to the second polypeptide;
   (c) identifying at least one package/antibody reagent that binds to the second polypeptide; and
   (d) determining the nucleotide sequence of the nucleic acid segment of the at least one package/antibody reagent, whereby the amino acid sequence corresponding to the nucleotide sequence can be deduced and is an indication of the amino acid sequence of an epitope shared by the first and second polypeptide.

2. The method of claim 1, wherein the providing step (a) comprises
   (i) cloning cDNA molecules prepared from a cell or tissue into a vector to create the replicable genetic packages; and
   (ii) incubating a population of antibodies with the replicable genetic packages to form the population of package/antibody reagents.

3. The method of claim 2, wherein the preparing step (a) further comprises preparing a population of immunogens and generating the population of antibodies with the population of immunogens.

4. The method of claim 3, wherein the population of immunogens comprise some or all of the proteins expressed in the cell or tissue.

5. The method of claim 4, wherein the at least some of the proteins are part of a fusion protein.

6. The method of claim 5, wherein the fusion protein includes glutathione-S-transferase (GST).

7. The method of claim 3, wherein the population of immunogens comprises a display library, the members of the display library comprising a replicable genetic package that displays one of the first polypeptides displayed by the package/antibody reagents.

8. The method of claim 7, wherein the polypeptides displayed on members of the display library are peptides having random amino acid sequences.

9. The method of claim 8, wherein the replicable genetic packages which display the peptides differ in type from the replicable genetic packages of the package/antibody reagents.

10. The method of claim 8, wherein the peptides displayed on members of the display library are up to 100 amino acids in length.

11. The method of claim 10, wherein the peptides displayed on members of the display library are 6 to 20 amino acids in length.

12. The method of claim 11, wherein the peptides displayed on members of the display library are 6 to 10 amino acids in length.

13. The method of claim 1, wherein
   (i) the second polypeptide is one of multiple different polypeptides within a sample;
   (ii) the contacting step (b) comprises contacting the population of package/antibody reagents with the sample; and (iii) the identifying step (c) comprises identifying package/antibody reagents that have formed complexes with the different polypeptides.

14. The method of claim 1, wherein the second polypeptide is within an electrophoretic separation matrix, and the contacting step (b) comprises excising a section from the separation matrix that contains the second polypeptide, eluting the second polypeptide from the excised section and contacting the eluted second polypeptide with the package/antibody reagents.

15. The method of claim 1, wherein
   (i) the second polypeptide is a polypeptide located within an electrophoretic separation matrix;
   (ii) the contacting step (b) comprises contacting the separation matrix or a replica thereof with the package/antibody reagents; and
   (iii) the identifying step (c) comprises isolating the at least one package/antibody reagent from the separation matrix or the replica thereof.

16. The method of claim 1, wherein
   (i) the second polypeptide is one of a plurality of polypeptides at different locations within a two-dimensional electrophoretic separation matrix;
   (ii) the contacting step (b) comprises contacting the two-dimensional electrophoretic separation matrix or a replica thereof with the package/antibody reagents;
   (iii) the identifying step (c) comprises isolating package/antibody reagents that have formed complexes with the different polypeptides; and
   (iv) the determining step (d) comprises determining the sequence of the segment of the nucleic acid of each of the isolated package/antibody reagents.

17. The method of claim 16, wherein
   (i) the plurality of polypeptides within the separation matrix comprise a plurality of polypeptides that have different primary sequences and a plurality of polypeptides that have the same primary sequence but which are differentially modified; and
   (ii) the determining step (d) comprises determining which of the plurality of proteins within the separation matrix have the same primary sequence but are differentially modified.

18. The method of claim 1, wherein the second polypeptide is obtained from or contained in a tissue sample.

19. The method of claim 18, wherein the tissue sample is a slice from a tissue.

20. The method of claim 1, wherein the second polypeptide is obtained from or contained in a subcellular compartment.

21. The method of claim 1, wherein the replicable genetic package of the package/antibody complex is selected from the group consisting of a virus, a bacteriophage, a bacterium, a polysome and a spore.

22. The method of claim 1, wherein the replicable genetic package is a bacteriophage.

23. The method of claim 1, wherein the captured antibodies comprise monovalent antibodies displayed in a multivalent format.

24. The method of claim 23, wherein the monovalent antibodies are scFv polypeptides.

25. The method of claim 24, wherein the scFv polypeptides are displayed in a multivalent format on phage.

26. The method of claim 1, wherein the captured antibody is a diabody, a tribody or a tetrabody.

27. The method of claim 1, wherein at least some of the members of the population display a single copy of the first polypeptide which is complexed with a single copy of the captured antibody.

28. The method of claim 1, wherein the first polypeptide is complexed with a plurality of copies of the same captured antibody.

29. The method of claim 1, wherein the first polypeptide is complexed with multiple different antibodies.

30. The method of claim 1, wherein at least some of the members of the population display multiple copies of the first polypeptide, each copy of the first polypeptide complexed with one or more captured antibodies having specific affinity for the first polypeptide, whereby such members display a plurality of antibodies.

31. The method of claim 30, wherein at least some of the plurality of antibodies have different protein sequences but specific affinity for the same epitope.

32. The method of claim 30, wherein at least some of the plurality of antibodies have different protein sequences and have specific affinity for different epitopes.

33. The method of claim 1, wherein at least some members of the population form an aggregate, comprising a plurality of members linked via the captured antibody that is complexed to the first polypeptide on each of the plurality of members.

34. The method of claim 1, wherein
   (i) the second polypeptide with which the population of package/antibody complexes is contacted is a receptor expressed on a surface of a cell, whereby the at least one package/antibody complex binds to the receptor and is subsequently transported into and/or through the cell; and
   (ii) the identifying step comprises detecting the transport of the at least one package/antibody reagent into and/or through the cell.

35. The method of claim 34, wherein the cell is a polarized cell and the identifying step comprises detecting transport through the cell.

36. The method of claim 34, wherein the cell is a non-polarized cell and the identifying step comprises detecting transport into the cell.

* * * * *